us011287416B2

(12) United States Patent
Greenfield et al.

(10) Patent No.: US 11,287,416 B2
(45) Date of Patent: Mar. 29, 2022

(54) CANCER

(71) Applicant: NEURO-BIO LTD, Abingdon (GB)

(72) Inventors: Susan Adele Greenfield, Abingdon (GB); Henry Tu, Abingdon (GB); Paul Morrill, Abingdon (GB); Sara Garcia-Rates, Abingdon (GB); Chris Pepper, Cardiff (GB); Chris Fegan, Cardiff (GB)

(73) Assignee: NEURO-BIO LTD, Abingdon (GB)

( * ) Notice: Subject to any disclaimer, the term of this patent is extended or adjusted under 35 U.S.C. 154(b) by 481 days.

(21) Appl. No.: 16/073,121

(22) PCT Filed: Jan. 30, 2017

(86) PCT No.: PCT/GB2017/050227
§ 371 (c)(1),
(2) Date: Jul. 26, 2018

(87) PCT Pub. No.: WO2017/130003
PCT Pub. Date: Aug. 3, 2017

(65) Prior Publication Data
US 2019/0025289 A1    Jan. 24, 2019

(30) Foreign Application Priority Data

Jan. 28, 2016 (GB) .................................... 1601585

(51) Int. Cl.
| | | |
|---|---|---|
| *G01N 31/00* | (2006.01) | |
| *G01N 33/53* | (2006.01) | |
| *G01N 33/50* | (2006.01) | |
| *C12N 9/18* | (2006.01) | |
| *C07K 16/40* | (2006.01) | |
| *A61P 35/00* | (2006.01) | |
| *C12Q 1/6886* | (2018.01) | |
| *A61P 35/04* | (2006.01) | |
| *A61K 31/165* | (2006.01) | |
| *A61K 31/4045* | (2006.01) | |
| *G01N 33/574* | (2006.01) | |
| *A61K 39/00* | (2006.01) | |

(52) U.S. Cl.
CPC ....... *G01N 33/5017* (2013.01); *A61K 31/165* (2013.01); *A61K 31/4045* (2013.01); *A61P 35/00* (2018.01); *A61P 35/04* (2018.01); *C07K 16/40* (2013.01); *C12N 9/18* (2013.01); *C12Q 1/6886* (2013.01); *C12Y 301/01007* (2013.01); *G01N 33/574* (2013.01); *A61K 2039/505* (2013.01); *C07K 2317/34* (2013.01); *C07K 2317/73* (2013.01); *C07K 2317/76* (2013.01); *C12Q 2600/106* (2013.01)

(58) Field of Classification Search
None
See application file for complete search history.

(56) References Cited

FOREIGN PATENT DOCUMENTS

| WO | WO 97/35962 A1 | 10/1997 | |
|---|---|---|---|
| WO | WO-9735962 A1 * | 10/1997 | ............ C07K 16/40 |
| WO | WO 01/73446 A1 | 10/2001 | |
| WO | WO 02/42778 A2 | 5/2002 | |

OTHER PUBLICATIONS

Onganer et al. (Biochimica et Biophysica Acta, vol. 1760, 2006, pp. 415-420) (Year: 2006).*
Francisco et al. (Breast Cancer Research and treatment, vol. 80, pp. 105-114, 2003) (Year: 2003).*
Ruiz-Espejo et al. (Breast Cancer Research and Treatment, vol. 80, pp. 105-114) (Year: 2003).*
International Search Report and the Written Opinion of PCT/GB2017/050227 dated Jul. 21, 2017, 20 pages.
Cottingham et al., "The Intact Human Acetylcholinesterase C-Terminal Oligomerization Domain is α-Helical in Situ and in Isolation, but a Shorter Fragment Forms βSheet-Rich Amyloid Fibrils and Protofibrillar Oligomers", Biochemistry, American Chemical Society, Sep. 16, 2003, vol. 42, No. 36, pp. 10863-10873, XP002497353.
Onganer et al., "An Acetylcholinesterase-Derived Peptide Inhibits Endocytic Membrane Activity in a Human Metastatic Breast Cancer Cell Line", Biochimica et Biophysica Acta (BBA)—General Subjects, Elsevier, Amsterdam, NL, Mar. 1, 2006, vol. 1760, No. 3, pp. 415-420, XP025014834.

* cited by examiner

*Primary Examiner* — Lisa V Cook
(74) *Attorney, Agent, or Firm* — Squire Patton Boggs (US) LLP

(57) ABSTRACT

The invention relates to cancer, and in particular to novel pharmaceutical compositions, therapies and methods for treating, preventing or ameliorating cancer, and especially metastatic disease. The invention also relates to diagnostic and prognostic methods for cancer and metastatic disease, and biomarkers for these conditions.

15 Claims, 37 Drawing Sheets

Specification includes a Sequence Listing.

Fig. 24

| Mean = | 47.76995 |
|---|---|
| STD = S = | 15.02168 |
| S/2 = | 7.510838 |

| Relative Values (%) | | | | | | |
|---|---|---|---|---|---|---|
| Serum Sample | | Average | Standard Deviation | Number of repeated measures | Average - Mean | T14 Group |
| Neuro-Bio | Chris Pepper | | | | | |
| CPS 21 | BO935 | 14.667 | 3.173 | 6 | -33.103 | LOW |
| CPS 19 | BO903 | 18.550 | 6.027 | 6 | -29.220 | LOW |
| CPS 38 | BO702 | 20.215 | 5.075 | 6 | -27.555 | LOW |
| CPS 86 | BO865 | 23.170 | 2.285 | 6 | -24.600 | LOW |
| CPS 23 | BO742 | 25.813 | 3.482 | 6 | -21.957 | LOW |
| CPS 29 | BO824 | 26.237 | 8.684 | 6 | -21.533 | LOW |
| CPS 89 | BO993 | 27.730 | 12.495 | 6 | -20.040 | LOW |
| CPS 03 | BO837 | 28.062 | 2.351 | 6 | -19.707 | LOW |
| CPS 08 | BO764 | 28.637 | 9.814 | 6 | -19.133 | LOW |
| CPS 62 | BO875 | 30.594 | 8.730 | 6 | -17.176 | LOW |
| CPS 37 | BO997 | 31.008 | 3.257 | 6 | -16.762 | LOW |
| CPS 33 | BO707 | 31.391 | 3.278 | 6 | -16.379 | LOW |
| CPS 100 | BO799 | 32.017 | 3.723 | 6 | -15.753 | LOW |
| CPS 58 | BO866 | 33.066 | 11.533 | 6 | -14.704 | LOW |
| CPS 79 | BO751 | 34.599 | 3.878 | 6 | -13.171 | LOW |
| CPS 96 | BO724 | 35.355 | 1.877 | 6 | -12.414 | LOW |
| CPS 01 | BO990 | 37.887 | 10.976 | 6 | -9.883 | LOW |
| CPS 70 | BO711 | 37.958 | 2.685 | 6 | -9.812 | LOW |
| CPS 06 | BO750 | 38.180 | 2.189 | 6 | -9.590 | LOW |
| CPS 05 | BO864 | 38.714 | 5.437 | 6 | -9.055 | LOW |
| CPS 73 | BO783 | 38.815 | 7.109 | 6 | -8.955 | LOW |
| CPS 50 | BO929 | 38.886 | 7.025 | 6 | -8.884 | LOW |
| CPS 51 | BO982 | 39.199 | 4.527 | 6 | -8.571 | LOW |
| CPS 46 | BO992 | 39.310 | 6.169 | 6 | -8.460 | LOW |
| CPS 74 | BO934 | 40.167 | 2.486 | 6 | -7.603 | LOW |
| CPS 31 | BO772 | 40.359 | 1.347 | 6 | -7.411 | MED-LOW |
| CPS 15 | BO859 | 40.480 | 1.958 | 6 | -7.290 | MED-LOW |
| CPS 90 | BO831 | 40.772 | 1.698 | 6 | -6.998 | MED-LOW |
| CPS 09 | BO940 | 40.782 | 8.022 | 6 | -6.988 | MED-LOW |
| CPS 59 | BO714 | 40.924 | 9.717 | 6 | -6.846 | MED-LOW |

| | | | | | | | |
|---|---|---|---|---|---|---|---|
| CPS 52 | BO853 | 40.984 | 3.262 | 6 | -6.786 | | |
| CPS 67 | BO966 | 41.105 | 3.371 | 6 | -6.665 | | |
| CPS 54 | BO920 | 41.156 | 2.391 | 6 | -6.614 | | |
| CPS 95 | BO948 | 42.033 | 1.809 | 6 | -5.737 | | |
| CPS 56 | BO801 | 42.225 | 8.136 | 6 | -5.545 | | |
| CPS 34 | BO839 | 42.346 | 3.406 | 6 | -5.424 | | |
| CPS 91 | BO945 | 42.386 | 6.098 | 6 | -5.384 | | |
| CPS 55 | BO732 | 42.951 | 2.325 | 6 | -4.819 | | |
| CPS 65 | BO752 | 43.657 | 4.838 | 6 | -4.113 | | |
| CPS 68 | BO926 | 43.718 | 7.851 | 6 | -4.052 | | |
| CPS 11 | BO961 | 44.252 | 2.974 | 6 | -3.518 | | |
| CPS 98 | BO769 | 44.262 | 12.278 | 6 | -3.508 | | |
| CPS 92 | BO954 | 44.545 | 3.485 | 6 | -3.225 | | |
| CPS 84 | BO880 | 45.291 | 3.549 | 6 | -2.479 | | |
| CPS 63 | BO939 | 45.574 | 6.914 | 6 | -2.196 | | |
| CPS 71 | BO775 | 45.604 | 2.293 | 6 | -2.166 | | |
| CPS 69 | BO863 | 45.735 | 6.720 | 6 | -2.035 | | |
| CPS 47 | BO745 | 45.907 | 4.961 | 6 | -1.863 | | |
| CPS 60 | BO844 | 45.907 | 6.143 | 6 | -1.863 | | |
| CPS 64 | BO986 | 46.381 | 3.536 | 6 | -1.389 | | |
| CPS 72 | BO840 | 46.835 | 2.963 | 6 | -0.935 | | Mean |
| CPS 25 | BO825 | 48.005 | 1.486 | 6 | 0.235 | | |
| CPS 61 | BO734 | 48.287 | 4.727 | 6 | 0.517 | | |
| CPS 88 | BO757 | 48.913 | 13.751 | 6 | 1.143 | | |
| CPS 43 | BO758 | 50.042 | 3.485 | 6 | 2.272 | | |
| CPS 97 | BO962 | 50.224 | 5.593 | 6 | 2.454 | | |
| CPS 10 | BO739 | 50.436 | 5.457 | 6 | 2.666 | | |
| CPS 85 | BO976 | 50.617 | 2.498 | 6 | 2.847 | | |
| CPS 13 | BO776 | 50.769 | 2.990 | 6 | 2.999 | | |
| CPS 42 | BO944 | 52.019 | 3.275 | 6 | 4.249 | MED-HIGH | |
| CPS 57 | BO991 | 52.675 | 5.210 | 6 | 4.905 | | |
| CPS 07 | BO950 | 53.422 | 8.776 | 6 | 5.652 | | |
| CPS 02 | BO761 | 53.724 | 2.204 | 6 | 5.954 | | |
| CPS 40 | BO868 | 53.875 | 2.789 | 6 | 6.106 | | |
| CPS 99 | BO867 | 53.997 | 10.182 | 6 | 6.227 | | |
| CPS 44 | BO737 | 54.168 | 4.421 | 6 | 6.398 | | |
| CPS 93 | BO829 | 54.531 | 4.390 | 6 | 6.761 | | |
| CPS 12 | BO904 | 54.672 | 7.481 | 6 | 6.902 | | |
| CPS 80 | BO715 | 55.207 | 3.507 | 6 | 7.437 | | +1/2*S |
| CPS 66 | BO971 | 55.318 | 2.840 | 6 | 7.548 | HIGH | |
| CPS 14 | BO796 | 55.439 | 1.741 | 6 | 7.669 | | |

Fig. 24 (cont.)

| CPS 26 | BO756 | 55.752 | 2.871 | 6 | 7.082 |
|---|---|---|---|---|---|
| CPS 78 | BO979 | 55.873 | 9.611 | 6 | 5.103 |
| CPS 30 | BO716 | 56.296 | 8.265 | 6 | 8.526 |
| CPS 48 | BO973 | 56.387 | 9.690 | 6 | 5.617 |
| CPS 76 | BO738 | 57.174 | 6.071 | 6 | 9.404 |
| CPS 35 | BO740 | 57.265 | 2.005 | 6 | 9.495 |
| CPS 20 | BO792 | 58.556 | 4.094 | 6 | 10.786 |
| CPS 53 | BO763 | 59.343 | 3.076 | 6 | 11.573 |
| CPS 82 | BO790 | 59.716 | 8.480 | 6 | 11.946 |
| CPS 24 | BO743 | 60.503 | 1.482 | 6 | 12.733 |
| CPS 87 | BO765 | 61.098 | 5.339 | 6 | 13.328 |
| CPS 18 | BO721 | 61.491 | 8.139 | 6 | 13.721 |
| CPS 77 | BO780 | 61.612 | 2.694 | 6 | 13.842 |
| CPS 04 | BO771 | 62.238 | 2.342 | 6 | 14.468 |
| CPS 22 | BO712 | 63.176 | 4.773 | 6 | 15.406 |
| CPS 16 | BO953 | 63.287 | 7.890 | 6 | 15.517 |
| CPS 45 | BO967 | 65.092 | 3.600 | 6 | 17.322 |
| CPS 49 | BO797 | 65.123 | 17.909 | 6 | 17.353 |
| CPS 81 | BO810 | 65.435 | 5.612 | 6 | 17.665 |
| CPS 28 | BO729 | 66.414 | 10.677 | 6 | 18.644 |
| CPS 39 | BO722 | 67.715 | 10.186 | 6 | 19.945 |
| CPS 36 | BO709 | 68.462 | 3.173 | 6 | 20.692 |
| CPS 75 | BO988 | 74.524 | 8.145 | 6 | 26.754 |
| CPS 94 | BO747 | 75.220 | 1.838 | 6 | 27.450 |
| CPS 27 | BO731 | 75.240 | 7.081 | 6 | 27.470 |
| CPS 17 | BO704 | 97.956 | 10.974 | 6 | 50.186 |

Fig. 27

Table 1 T14 50KDa/TP raw values from 100 serum samples from leukaemia patients detected by WB, separated groups below and above the median

| Light grey group < Median | | | Dark grey group > Median | | |
| --- | --- | --- | --- | --- | --- |
| NB Reference | Tube Reference | T14 50 kDa/TP | NB Reference | Tube Reference | T14 50 kDa/TP |
| CPS01 | BO990 | 0.161699061 | CPS40 | BO868 | 0.875507073 |
| CPS89 | BO993 | 0.174602077 | CPS10 | BO739 | 0.905317237 |
| CPS21 | BO935 | 0.188430854 | CPS13 | BO776 | 0.912010868 |
| CPS51 | BO982 | 0.218839404 | CPS45 | BO967 | 0.912777387 |
| CPS95 | BO948 | 0.236814882 | CPS23 | BO742 | 0.950061693 |
| CPS06 | BO750 | 0.25045659 | CPS76 | BO738 | 0.960638794 |
| CPS14 | BO796 | 0.256609897 | CPS65 | BO752 | 0.980894332 |
| CPS38 | BO702 | 0.256710327 | CPS19 | BO903 | 0.99791595 |
| CPS64 | BO986 | 0.269818722 | CPS93 | BO829 | 1.01021687 |
| CPS12 | BO904 | 0.286831782 | CPS59 | BO714 | 1.017028699 |
| CPS09 | BO940 | 0.350899354 | CPS42 | BO944 | 1.034984758 |
| CPS37 | BO997 | 0.384202865 | CPS20 | BO792 | 1.043190175 |
| CPS86 | BO865 | 0.411267653 | CPS44 | BO737 | 1.072372342 |
| CPS100 | BO799 | 0.415646302 | CPS28 | BO729 | 1.129882247 |
| CPS33 | BO707 | 0.426683394 | CPS43 | BO758 | 1.144859688 |
| CPS73 | BO783 | 0.427410005 | CPS85 | BO976 | 1.171341584 |
| CPS91 | BO945 | 0.438600343 | CPS27 | BO731 | 1.195429419 |
| CPS61 | BO734 | 0.449024365 | CPS75 | BO988 | 1.220902806 |
| CPS17 | BO704 | 0.463262396 | CPS56 | BO801 | 1.222480974 |
| CPS46 | BO992 | 0.472848022 | CPS70 | BO711 | 1.305662632 |
| CPS79 | BO751 | 0.500011094 | CPS58 | BO866 | 1.32401572 |
| CPS11 | BO961 | 0.508362847 | CPS16 | BO953 | 1.35616638 |
| CPS53 | BO763 | 0.511087397 | CPS57 | BO991 | 1.38509208 |
| CPS78 | BO979 | 0.518055834 | CPS90 | BO831 | 1.40943126 |
| CPS81 | BO810 | 0.539183244 | CPS32 | BO978 | 1.431265646 |
| CPS62 | BO875 | 0.541310938 | CPS35 | BO740 | 1.436627543 |
| CPS96 | BO724 | 0.551257463 | CPS83 | BO720 | 1.465130533 |
| CPS47 | BO745 | 0.564976291 | CPS74 | BO934 | 1.532815843 |
| CPS25 | BO825 | 0.575754249 | CPS97 | BO962 | 1.577371822 |
| CPS41 | BO766 | 0.591162636 | CPS05 | BO864 | 1.663410075 |
| CPS04 | BO771 | 0.599006303 | CPS88 | BO757 | 1.702962816 |
| CPS80 | BO715 | 0.600399502 | CPS67 | BO966 | 1.731763336 |

Fig. 27 (cont.)

| CPS29 | BO824 | 0.602249975 | CPS18 | BO721 | 1.764296136 |
|---|---|---|---|---|---|
| CPS36 | BO709 | 0.624766582 | CPS87 | BO765 | 1.777437922 |
| CPS60 | BO844 | 0.626769354 | CPS98 | BO769 | 1.875072249 |
| CPS48 | BO973 | 0.632283636 | CPS92 | BO954 | 1.93980376 |
| CPS49 | BO797 | 0.635924863 | CPS99 | BO867 | 2.121789963 |
| CPS66 | BO971 | 0.65391734 | CPS84 | BO880 | 2.160466939 |
| CPS15 | BO859 | 0.660255508 | CPS02 | BO761 | 2.177740673 |
| CPS30 | BO716 | 0.660973725 | CPS08 | BO764 | 2.225280123 |
| CPS50 | BO929 | 0.67432876 | CPS34 | BO839 | 2.267113767 |
| CPS31 | BO772 | 0.682906184 | CPS03 | BO837 | 2.347675716 |
| CPS55 | BO732 | 0.700204877 | CPS82 | BO790 | 2.372391337 |
| CPS52 | BO853 | 0.701115977 | CPS94 | BO747 | 2.438942282 |
| CPS72 | BO840 | 0.736716148 | CPS63 | BO939 | 2.543884304 |
| CPS26 | BO756 | 0.758025464 | CPS24 | BO743 | 2.618966695 |
| CPS68 | BO926 | 0.758307578 | CPS22 | BO712 | 2.660249606 |
| CPS39 | BO722 | 0.771825496 | CPS69 | BO863 | 2.801469228 |
| CPS71 | BO775 | 0.80108958 | CPS54 | BO920 | 2.934273694 |
| CPS77 | BO780 | 0.814959243 | CPS07 | BO950 | 3.685907851 |

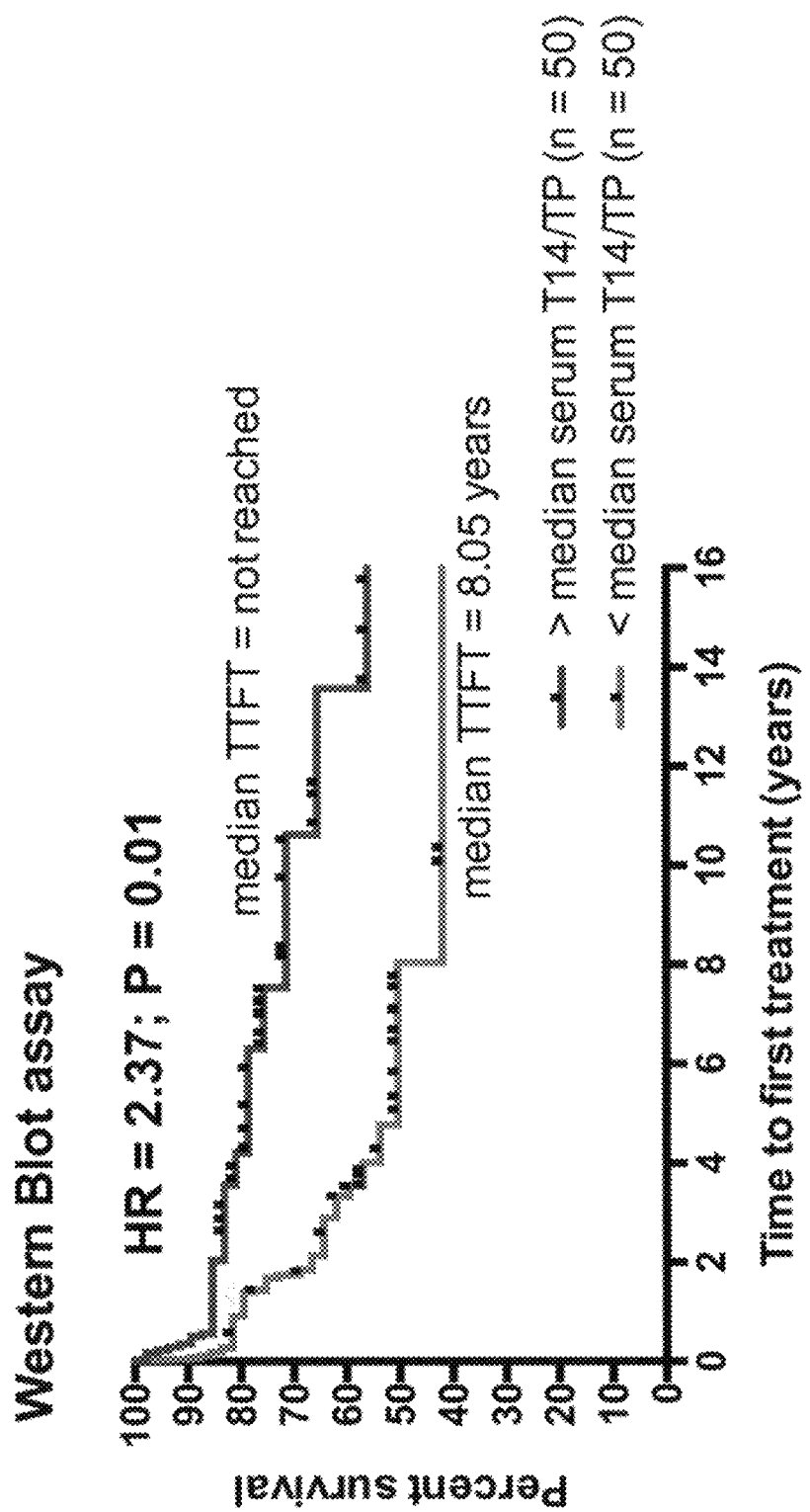

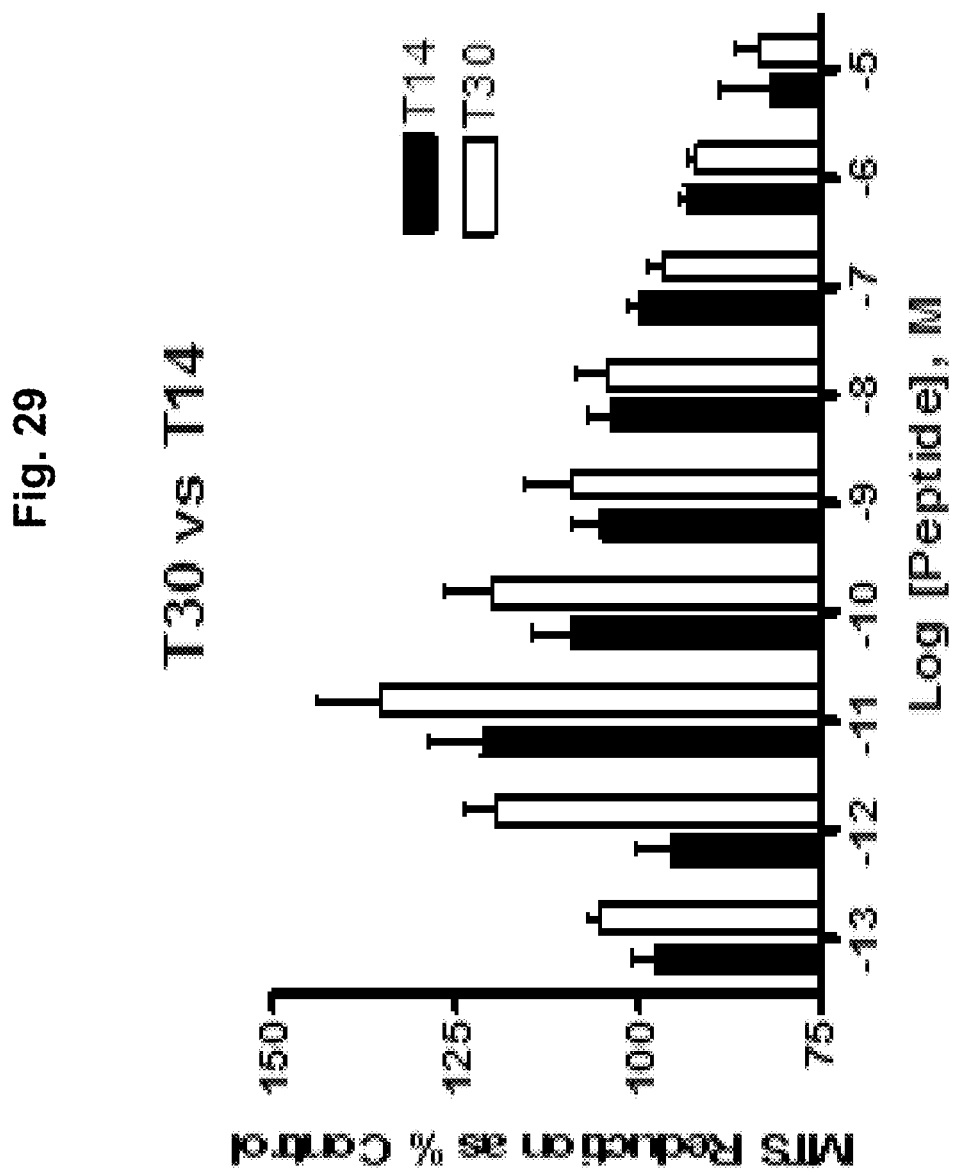

SEQUENCE LISTING

<160> NUMBER OF SEQ ID NOS: 7

<210> SEQ ID NO 1
<211> LENGTH: 614
<212> TYPE: PRT
<213> ORGANISM: Homo sapiens

<400> SEQUENCE: 1

```
Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
            35                  40                  45

Arg Gly Ile Arg Leu Lys Thr Pro Gly Gly Pro Val Ser Ala Phe Leu
        50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
        130                 135                 140

Val Leu Val Trp Ile Tyr Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
            195                 200                 205

Leu Ala Leu Gln Trp Val Gln Glu Asn Val Ala Ala Phe Gly Gly Asp
        210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
        275                 280                 285

Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
        355                 360                 365
```

```
Phe Leu Val Tyr Gly Ala Pro Gly Phe Ser Lys Asp Asn Glu Ser Leu
        370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Val Phe Glu His Arg
450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
        515                 520                 525

Pro Gln Trp Pro Pro Tyr Thr Ala Gly Ala Gln Gln Tyr Val Ser Leu
530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
        595                 600                 605

Asp Arg Cys Ser Asp Leu
        610

<210> SEQ ID NO 2
<211> LENGTH: 30
<212> TYPE: PRT
<213> ORGANISM: Homo sapiens

<400> SEQUENCE: 2

Lys Ala Glu Phe His Arg Trp Ser Ser Tyr Met Val His Trp Lys Asn
1               5                   10                  15

Gln Phe Asp His Tyr Ser Lys Gln Asp Arg Cys Ser Asp Leu
            20                  25                  30

<210> SEQ ID NO 3
<211> LENGTH: 14
<212> TYPE: PRT
<213> ORGANISM: Homo sapiens

<400> SEQUENCE: 3

Ala Glu Phe His Arg Trp Ser Ser Tyr Met Val His Trp Lys
1               5                   10

<210> SEQ ID NO 4
<211> LENGTH: 15
<212> TYPE: PRT
<213> ORGANISM: Homo sapiens
```

```
<400> SEQUENCE: 4

Asn Gln Phe Asp His Tyr Ser Lys Gln Asp Arg Cys Ser Asp Leu
1               5                   10                  15

<210> SEQ ID NO 5
<211> LENGTH: 7
<212> TYPE: PRT
<213> ORGANISM: Homo sapiens

<400> SEQUENCE: 5

Ser Tyr Met Val His Trp Lys
1               5

<210> SEQ ID NO 6
<211> LENGTH: 4
<212> TYPE: PRT
<213> ORGANISM: Homo sapiens

<400> SEQUENCE: 6

Val His Trp Lys
1

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Cys Ala Glu Phe His Arg Trp Ser Ser Tyr Met Val His Trp Lys
1               5                   10                  15
```

CANCER

CROSS-REFERENCE TO RELATED APPLICATION

This application is a filing under 35 U.S.C. § 371 of International Patent Application No. PCT/GB2017/050227, filed Jan. 30, 2017, which claims priority to United Kingdom Patent Application No. 1601585.1, filed Jan. 28, 2016. Each of the foregoing applications is incorporated herein by reference in its entirety.

The invention relates to cancer, and in particular to novel pharmaceutical compositions, therapies and methods for treating, preventing or ameliorating cancer, and especially metastatic disease. The invention also relates to diagnostic and prognostic methods for cancer and metastatic disease, and biomarkers for these conditions.

Cancer and malignant tumours form a group of diseases involving abnormal cell growth with the potential to invade or spread to other parts of the body, i.e. metastasis. In 2012, approximately 14 million new cases of cancer occurred globally. There is therefore a need to provide an improved diagnosis and therapies for the treatment of cancer and metastasis.

Acetylcholinesterase (AChE) is expressed at different stages of development in various forms, all of which have identical enzymatic activity, but which have very different molecular composition. The 'tailed' (T-AChE—SEQ ID No: 1) is expressed at synapses and the inventors have previously identified two peptides that could be cleaved from the C-terminus, one referred to as "T14" (SEQ ID No: 3), within the other which is known as "T30" (SEQ ID No: 2), and which both have strong sequence homology to the comparable region of β-amyloid. The AChE C-terminal peptide "T14" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30"—SEQ ID No: 3) display actions comparable to those reported for 'non-cholinergic' AChE, whereas the inert residue within the T30 sequence (i.e. "T15"—SEQ ID No: 4) is without effect.

The T14 peptide binds to an allosteric site on the α7 nicotinic-receptor, where, on its own, it has no effect. However, in the presence of a primary ligand, such as acetylcholine or dietary choline, T14 enhances the calcium influx induced by these primary agents. Excessive calcium can be taken up into the mitochondria where it compromises oxidative phosphorylation, and causes a leakage of electrons. Free radicals are consequently formed that then destabilize the membrane, and the cell then dies.

The inventors investigated the levels of the toxic T14 peptide, α7 nicotinic-receptor and acetylcholinesterase proteins using Western Blotting in cell lysate and cell culture media of seven cancer cell lines (MEC-1, KG1a, H929, MCF-7, MDA-MB 231, CLL, and JJN3). They found that only the toxic T14 peptide was released from the cancer cells, and that T14 concentrations were higher outside of the cells than the T14 levels inside cancer cells. The inventors then went on to investigate the relationship between the known metastatic marker CD44 with the toxic T14 peptide, AChE, and the α7 nicotinic-receptor in membrane and cytosol fractions of cancer cell lines. They were surprised to observe that CD44 is significantly and positively correlated with the toxic molecule T14. Collectively, these data strongly suggest that the toxic T14 peptide, including its biosynthesis and metabolic pathways, represents a good target for treating cancer and metastasis, and furthermore, that T14 itself acts as a robust biomarker for cancer metastasis.

Thus, in a first aspect of the invention, there is provided an inhibitor of the synthesis and/or activity of a peptide of SEQ ID No: 3, for use in treating, ameliorating or preventing cancer or metastatic disease.

In a second aspect, there is provided a method of treating, ameliorating or preventing cancer or metastatic disease in a subject, the method comprising, administering to a subject in need of such treatment, a therapeutically effective amount of an inhibitor of the synthesis and/or activity of a peptide of SEQ ID No: 3.

As described in Example 1, the inventors detected the levels of the toxic T14 peptide (SEQ ID No: 3), nicotinic alpha-7 receptor and acetylcholinesterase (AChE) proteins using Western Blotting in cell lysate and cell culture media of seven cancer cell lines (MEC-1, KG1a, H929, MCF-7, MDA-MB 231, CLL, and JJN3), and normal B lymphocytes acting as control. MDA-MB-231, KG1a, and MEC-1 cells are highly migratory cancer cell lines, whereas H929, JJN3, CLL and MCF-7 are less migratory cancer cell lines, and B-lymphocytes are normal, non-cancerous cells. T14, alpha 7 receptors and AChE were all detected within the cancer cells. Surprisingly, all three proteins have similar mobility and their levels are positively correlated with each other, suggesting that they are complexed with each other. However, outside cancer cells (i.e. within the cell culture media), only the toxic T14 peptide was detected. Even more surprising was that the T14 levels were higher outside the cells than they were inside six out of the seven cancer cell lines, suggesting that T14 is produced to be released from the cell. The inventors were also surprised to see that the levels of T14 outside of the cancer cells were significantly negatively correlated with alpha-7 receptor levels within the cancer cells.

Example 2 describes the use of Western Blotting to show the relationship between the well-known metastatic marker $CD_{44}$ with the toxic T14 peptide, AChE, and the alpha-7 receptor in membrane and cytosol fractions of six cancer cell lines (JJN3, MDA-MB231, MCF-7, KG1a, MEC-1, and H929) and also one cancer-derived cell line (PC12). In all cancer cell lines, the metastatic marker (CD44) is significantly and positively correlated with the toxic molecule T14, and this correlation holds true for within the cancer cell membrane as well as within the cancer cell cytosol. These findings strongly suggest that T14 is a good predictor of the degree of cancer and metastasis, i.e. tumour cell migration.

The cancer, which is treated in accordance with the first or second aspect, may be leukaemia. For example, the cancer may be lymphocytic leukaemia or chronic lymphocytic leukaemia (CLL). The cancer may be myeloid leukaemia, or acute myeloid leukaemia. The cancer may be multiple myeloma. The cancer may be breast cancer. The cancer may be plasmacytoma.

Most preferably, the inhibitor of T14 peptide (SEQ ID No: 3) synthesis and/or activity, is for use in treating, ameliorating or preventing metastatic disease or metastasis.

Acetylcholinesterase is a serine protease that hydrolyses acetylcholine, and will be well-known to the skilled person. The major form of acetylcholinesterase, which is found in the brain, is known as tailed acetylcholinesterase (T-AChE). The protein sequence of one embodiment of human tailed acetylcholinesterase (Gen Bank: AAA68151.1) is 614 amino acids in length, and is provided herein as SEQ ID No:1, as follows:

```
                                                                        [SEQ ID No: 1]
  1  mrppqcllht  pslasplll  llwllgggvg  aegredaell  vtvrggrlrg  irlktpggpv 61  saflgipfae  ppmgprrflp  pepkqpwsgv  vdattfqsvc  yqyvdtlypg  fegtemwnpn 121  relsedclyl  nvwtpyprpt  sptpvlvwiy  gggfysgass  ldvydgrflv  qaertvlvsm 181  nyrvgafgfl  alpgsreapg  nvglldqrla  lqwvqenvaa  fggdptsvtl  fgesagaasv 241  gmhllsppsr  glfhravlqs  gapngpwatv  gmgearrrat  qlahlvgcpp  ggtggndtel 301  vaclrtrpaq  vlvnhewhvl  pqesvfrfsf  vpvvdgdfls  dtpealinag  dfhglqvlvg 361  vvkdegsyfl  vygapgfskd  neslisraef  lagvrvgvpq  vsdlaaeavv  lhytdwlhpe 421  dparlreals  dvvgdhnvvc  pvaqlagrla  aqgarvyayv  fehrastlsw  plwmgvphgy 481  eiefifgipl  dpsrnytaee  kifaqrlmry  wanfartgdp  neprdpkapq  wppytagaqq 541  yvsldlrple  vrrglraqac  afwnrflpkl  lsatdtldea  erqwkaefhr  wssymvhwkn 601  qfdhyskqdr  csdl
```

It will be appreciated that the first 31 amino acid residues of SEQ ID No:1 are removed while the protein is released, thereby leaving a 583 amino acid sequence.

The amino acid sequence of T30 (which corresponds to the last 30 amino acid residues of SEQ ID No:1) is provided herein as SEQ ID No:2, as follows:

[SEQ ID No: 2]
KAEFHRWSSYMVHWKNQFDHYSKQDRCSDL

The amino acid sequence of the toxic T14 peptide (which corresponds to the 14 amino acid residues located towards the end of SEQ ID No:1, and lacks the final 15 amino acids found in T30) is provided herein as SEQ ID No:3, as follows:

[SEQ ID No: 3]
AEFHRWSSYMVHWK

The amino acid sequence of T15 (which corresponds to the last 15 amino acid residues of SEQ ID No:1) is provided herein as SEQ ID No:4, as follows:

[SEQ ID No: 4]
NQFDHYSKQDRCSDL

The inventors have found that inhibition of the toxic T14 peptide is required for the effective treatment of cancer or metastasis. Inhibitors of the invention may be used to prevent the development of cancer or development and spread of metastasis. For instance, the inhibitors may be given to subjects who are at risk (e.g. a genetic predisposition or adverse environmental exposure) of developing cancer or metastasis. The inhibitors may also be used after surgery, radiotherapy or chemotherapy to prevent cancer re-establishing itself in a subject.

The inventors have shown that the toxic T14 peptide binds to an allosteric site on the α7 nicotinic-receptor, where, on its own, it has no effect on the cell. However, in the presence of a primary ligand, such as acetylcholine or dietary choline, T14 enhances the calcium influx into the cell induced by these primary agents. Excessive calcium is taken up into the mitochondria where it compromises oxidative phosphorylation, and causes a leakage of electrons. Free radicals are consequently formed that then destabilize the membrane, and the cell then dies.

Based on the above understanding, the inventors have designed inhibitors that are capable of decreasing the synthesis or biological activity of the toxic T14 peptide, and which may achieve their effect by a number of biosynthetic and/or metabolic means. Preferably, the inhibitor can bind to T14, and prevent it from binding to the α7 nicotinic-receptor. The inventors have found that any T14 peptide that has managed to reach the allosteric site stays interacting with the receptor, and that this interaction can cause upregulations of more receptors within 24 hours, i.e. T14 can increase its own target. Accordingly, prevention of T14 interaction with the allosteric site is most preferred.

For instance, such inhibitors may:
(a) reduce the interaction between the T14 peptide and an allosteric site on the alpha-7 receptor;
(b) compete with endogenous T14 peptide for the allosteric site on the alpha-7 receptor;
(c) bind to the T14 peptide to reduce its biological activity;
(d) decrease post-translational cleavage of acetylcholinesterase polypeptide to create the T14 peptide; or
(e) inhibit T14 translocation to the allosteric site on the alpha-7 receptor.

In a preferred first embodiment of the invention, the inhibitor may directly interact with the T14 peptide (e.g. (a) to (c) above) to reduce T14's biochemical and/or metabolic activity, and thus toxicity, of T14, in the subject's cells. Preferably, the inhibitor results in a reduction in T14 interaction with the allosteric site on the alpha-7 receptor.

Preferred inhibitors comprise small molecule inhibitors. Such inhibitors may be identified as part of a high throughput screen of small molecule libraries. For example, the screening method according to the fifth aspect of the invention (see below) represents a suitable means of identifying such inhibitors which can be used to treat cancer or metastasis.

In a preferred embodiment, the inhibitor comprises a compound of Formula (I):

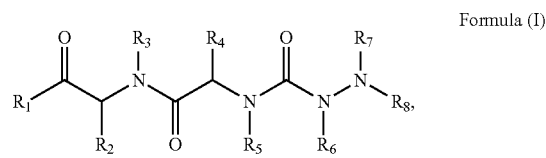

Formula (I)

wherein:

R$_1$ is —NR$_9$R$_{10}$ or —OH;
R$_2$ is

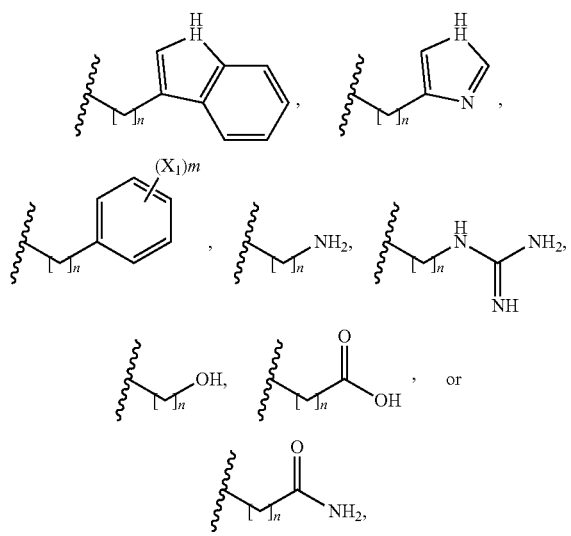

R$_3$ is —H or a C$_{1-5}$ straight or branched alkyl or alkenyl;
R$_4$ is

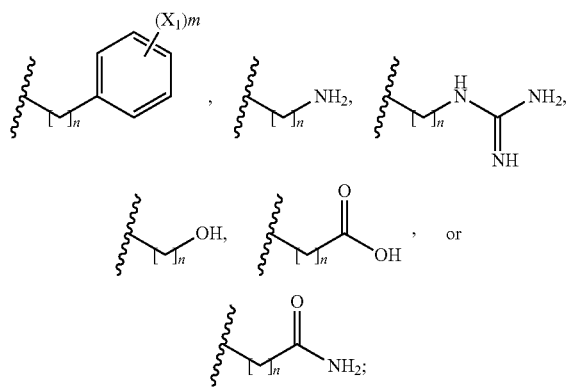

R$_5$ is —H or a C$_{1-5}$ straight or branched alkyl or alkenyl;
R$_6$ is

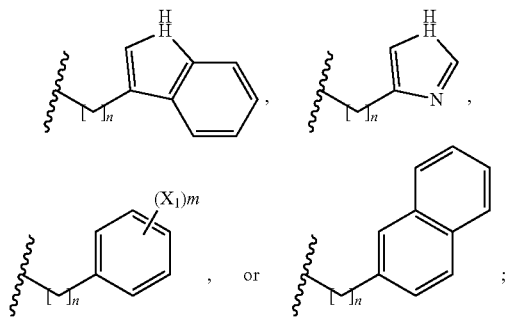

R$_7$ is —H or a C$_{1-5}$ straight or branched alkyl or alkenyl;
R$_8$ is —H; a C$_{1-5}$ straight or branched alkyl or alkenyl or

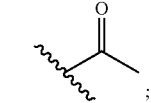

X$_1$ is —NR$_9$R$_{10}$, —OH or

the or each R$_9$ and R$_{10}$ are independently —H or a C$_{1-5}$ straight or branched alkyl or alkenyl;
R$_{11}$ is —NH$_2$, —OH or an aryl group;
the or each m is independently between 0 and 5; and
each n is independently between 0 and 10;
or a pharmaceutically acceptable salt, solvate, tautomeric form, or polymorphic form thereof.

It may be understood that the term "salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts may further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

It may be understood that the term "solvate" refers to a compound provided herein or a salt thereof, that further includes a stoichiometric or non-stoichiometric amount of solvent bound by non-covalent intermolecular forces. Where the solvent is water, the solvate is a hydrate.

It may be appreciated that an aryl group refers to a substituent derived from an aromatic ring. The aryl group may be a C6-C12 aryl group. Preferably, the aryl group is phenyl, biphenyl or naphthyl.

Most preferably, the compound has Formula (Ia):

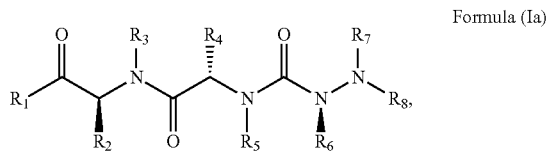

Formula (Ia)

$R_1$ may be —OH. However, preferably, $R_1$ is —$NR_9R_{10}$, more preferably $R_1$ is —$NR_9H$, and most preferably $R_1$ is —$NH_2$.

Preferably, $R_2$ is and n is

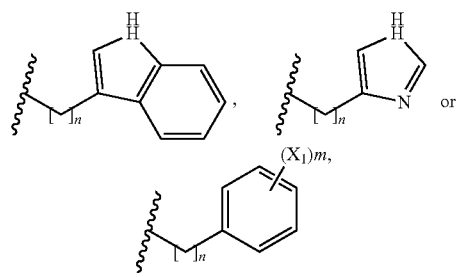

preferably between 1 and 5. Accordingly, n may be 1, 2, 3, 4 or 5, and most preferably n is 1.

It will be appreciated that in embodiments where $R_2$ is then m may

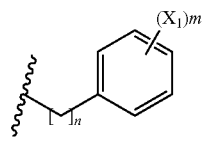

be 0, 1, 2, 3, 4 or 5. Preferably m is 1. Preferably, $X_1$ is in the para position.

In a preferred embodiment $R_2$ is

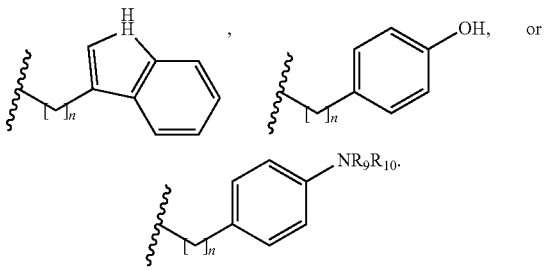

Preferably, in embodiments when $R_2$ is

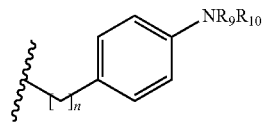

then at least one of $R_9$ or $R_{10}$ is —H, and most preferably $R_9$ or $R_{10}$ are both —H.

In a preferred embodiment, $R_2$ is

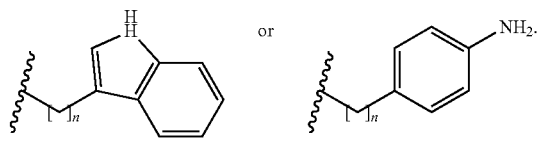

In a most preferred embodiment, $R_2$ is

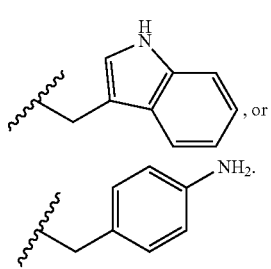

It will be appreciated that $R_3$ may be a methyl, ethyl, propyl, butyl or pentyl group. Preferably, $R_3$ is methyl. However, in a more preferred embodiment, $R_3$ is —H.

In one embodiment $R_4$ is

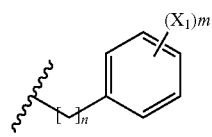

and n is preferably between 1 and 5. Accordingly, n may be 1, 2, 3, 4 or 5, and preferably n is 1.

In embodiments where R$_4$ is

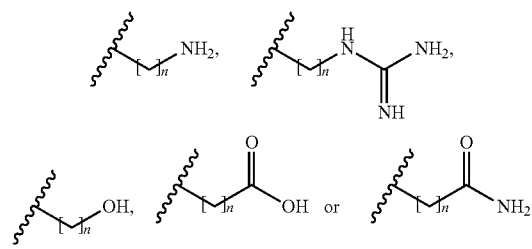

then n is preferably between 1 and 7, and is more preferably between 2 and 6. Accordingly, n may be 2, 3, 4, 5 or 6, and is preferably n is 3 or 4.

In one embodiment, R$_4$ is preferably

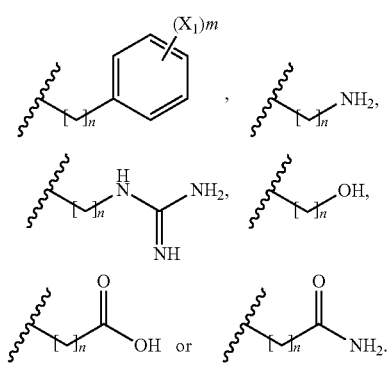

More preferably, R$_4$ is

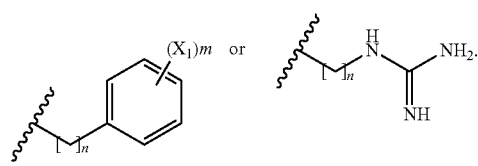

It will be appreciated that in embodiments where R$_4$ is

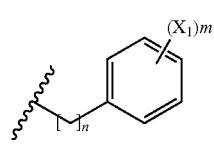

then m may be 0, 1, 2, 3, 4 or 5. Preferably m is 1. Preferably, X$_1$ is in the para position.

Preferably, R$_4$ is

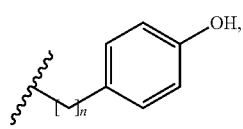

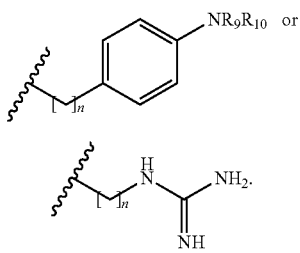

More preferably, R$_4$ is

Preferably, in embodiments when R$_4$ is then at least one of R$_9$ or R$_{10}$ is —H, and most preferably both R$_9$ or R$_{10}$ are —H.

Accordingly, R$_4$ is preferably

More preferably, R$_4$ is

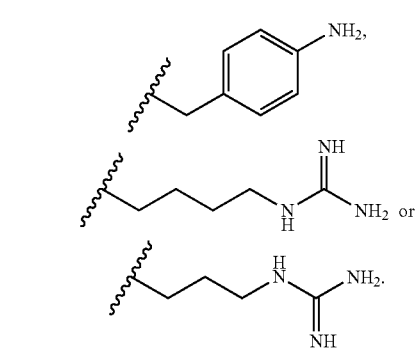

Most preferably, $R_4$ is

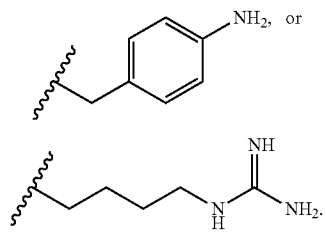

It will be appreciated that $R_5$ may be a methyl, ethyl, propyl, butyl or pentyl group. Preferably, $R_5$ is methyl. However, in a more preferred embodiment, $R_5$ is —H.

In $R_6$ is

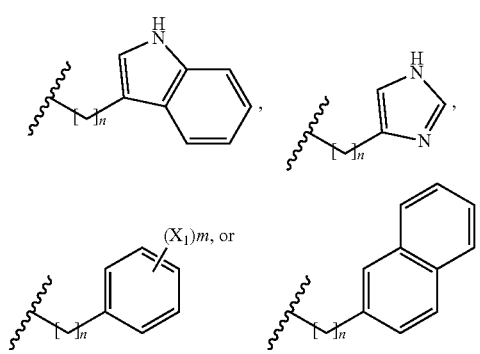

and n is between 1 and 5. Accordingly, n may be 1, 2, 3, 4 or 5, and preferably n is 1.

Preferably, $R_6$ is

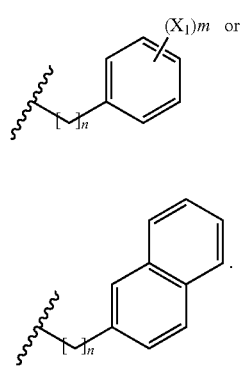

It will be appreciated that in embodiments where $R_6$ is

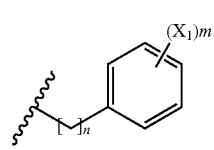

then m may be 0, 1, 2, 3, 4 or 5. Preferably, m is 0. More preferably, m is 1. Preferably, $X_1$ is in the para position.

In a preferred embodiment $R_6$ is

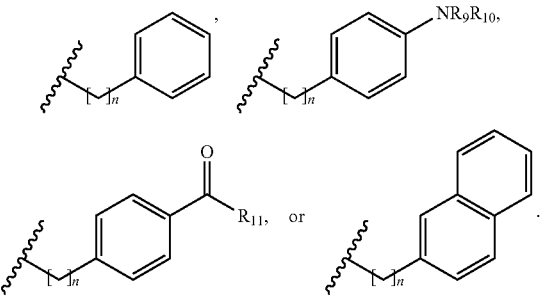

Preferably, in embodiments when $R_6$ is

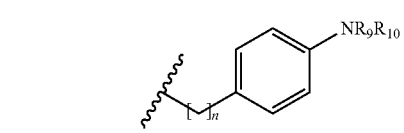

then at least one of $R_9$ or $R_{10}$ is —H, and most preferably both $R_9$ or $R_{10}$ are —H.

Preferably, in embodiments when $R_6$ is

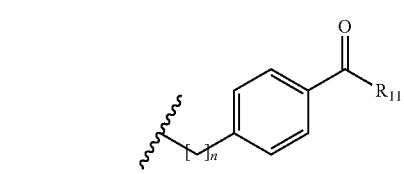

then $R_{11}$ is aryl, and most preferably phenyl.

In a preferred embodiment, $R_6$ is

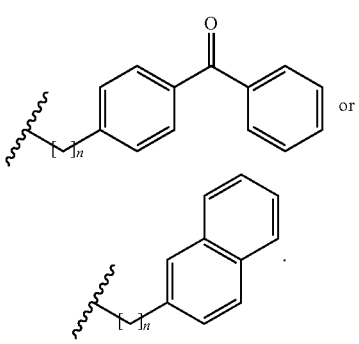

In a most preferred embodiment, $R_6$ is

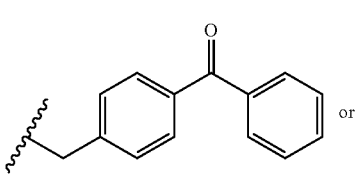

-continued

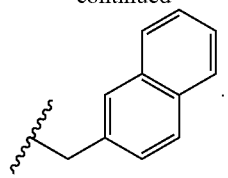

It will be appreciated that $R_7$ may be a methyl, ethyl, propyl, butyl or pentyl group. Preferably, $R_7$ is methyl. However, in a more preferred embodiment, $R_7$ is —H.

In one preferred embodiment $R_8$ is —H. However, in a more preferred embodiment $R_8$ is

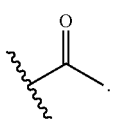

In a preferred embodiment, the inhibitor comprises a compound of Formula (I), wherein:
$R_2$ is

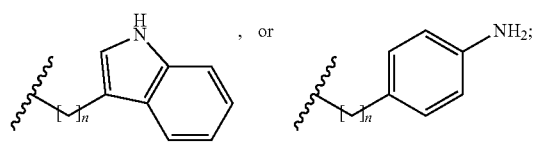

$R_3$ is H or a $C_{1-5}$ straight or branched alkyl or alkenyl;
$R_4$ is

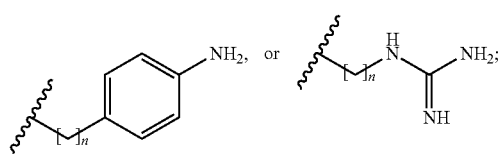

$R_5$ is H or a $C_{1-5}$ straight or branched alkyl or alkenyl;
$R_6$ is

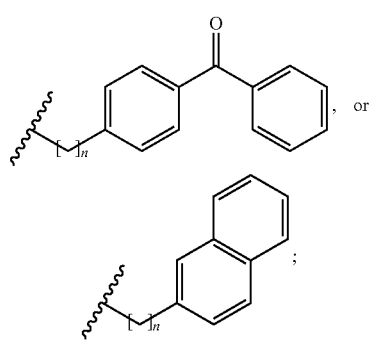

$R_7$ is H or a $C_{1-5}$ straight or branched alkyl or alkenyl.
Preferably, $R_3$ is H, $R_5$ is H and $R_7$ is H.
In a more preferred embodiment, the inhibitor comprises a compound of Formula (I), wherein:

$R_2$ is

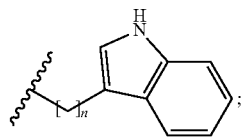

$R_3$ is H or a $C_{1-5}$ straight or branched alkyl or alkenyl;
$R_4$ is

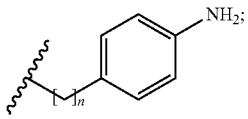

$R_5$ is H or a $C_{1-5}$ straight or branched alkyl or alkenyl; or
$R_6$ is

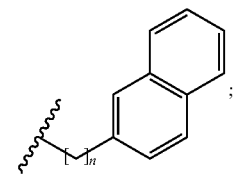

and
$R_7$ is H or a $C_{1-5}$ straight or branched alkyl or alkenyl.
Preferably, the inhibitor comprises a compound of Formula (Ia). Preferably, $R_3$ is H, $R_5$ is H and $R_7$ is H.
Preferably, $R_1$ is —OH and $R_8$ is H. More preferably, $R_1$ is $NH_2$ and $R_8$ is

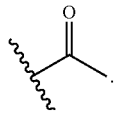 [SMILES: *C(C)=O]

In an alternative more preferred embodiment, the inhibitor comprises a compound of Formula (I), wherein:
$R_2$ is

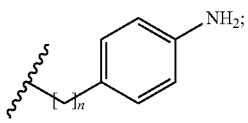

$R_3$ is H or a $C_{1-5}$ straight or branched alkyl or alkenyl;
$R_4$ is

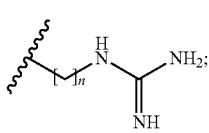

$R_5$ is H or a $C_{1-5}$ straight or branched alkyl or alkenyl; or
$R_6$ is

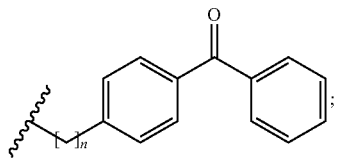

and $R_7$ is H or a $C_{1-5}$ straight or branched alkyl or alkenyl.

Preferably, the inhibitor comprises a compound of Formula (Ia). Preferably, $R_3$ is H, $R_5$ is H and $R_7$ is H.

Preferably, $R_1$ is —OH and $R_8$ is H. More preferably, $R_1$ is $NH_2$ and $R_8$ is

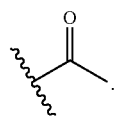

In an even more preferred embodiment, the inhibitor comprises a compound of Formula (I), wherein:
$R_2$

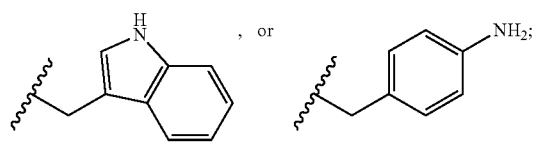 [SMILES: *Cc1c[nH]c2ccccc12 ; *Cc1ccc(N)cc1]

is $R_3$ is H or a $C_{1-5}$ straight or branched alkyl or alkenyl;
$R_4$ is

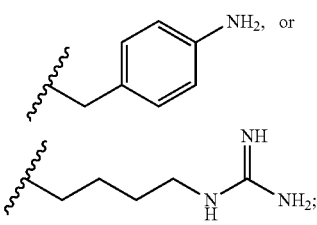

$R_5$ is H or a $C_{1-5}$ straight or branched alkyl or alkenyl;
$R_6$ is

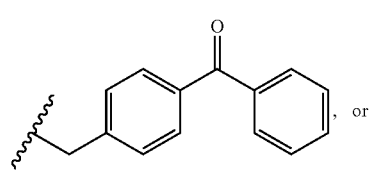

-continued

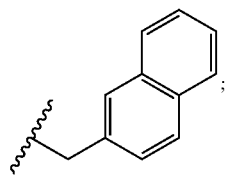

and $R_7$ is H or a $C_{1-5}$ straight or branched alkyl or alkenyl.

Preferably, $R_3$ is H, $R_5$ is H and $R_7$ is H.

In a more preferred embodiment, the inhibitor comprises a compound of Formula (I), wherein:
$R_2$ is

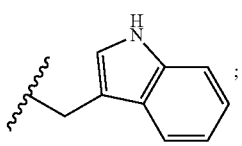 [SMILES: *Cc1c[nH]c2ccccc12]

$R_3$ is H or a $C_{1-5}$ straight or branched alkyl or alkenyl;
$R_4$ is

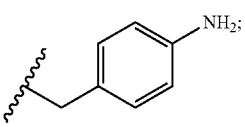 [SMILES: *Cc1ccc(N)cc1]

$R_5$ is H or a $C_{1-5}$ straight or branched alkyl or alkenyl; or
$R_6$ is

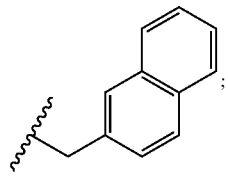 [SMILES: *Cc1ccc2ccccc2c1]

and $R_7$ is H or a $C_{1-5}$ straight or branched alkyl or alkenyl.

Preferably, the inhibitor comprises a compound of Formula (Ia). Preferably, $R_3$ is H, $R_5$ is H and $R_7$ is H.

Preferably, $R_1$ is —OH and $R_8$ is H. More preferably, $R_1$ is $NH_2$ and $R_8$ is

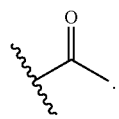

In an alternative more preferred embodiment, the inhibitor comprises a compound of Formula (I), wherein:

R₂ is

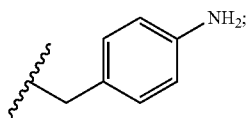 [SMILES: *Cc1ccc(N)cc1]

R₃ is H or a C₁₋₅ straight or branched alkyl or alkenyl;
R₄ is

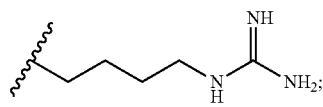 [SMILES: *CCCCNC(=N)N]

R₅ is H or a C₁₋₅ straight or branched alkyl or alkenyl; or
R₆ is

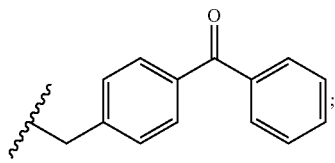 [SMILES: *Cc1ccc(C(=O)c2ccccc2)cc1]

and
R₇ is H or a C₁₋₅ straight or branched alkyl or alkenyl.

Preferably, the inhibitor comprises a compound of Formula (Ia). Preferably, R₃ is H, R₅ is H and R₇ is H.

Preferably, R₁ is —OH and R₈ is H. More preferably, R₁ is NH₂ and R₈ is

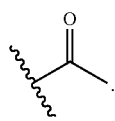

Preferably, the inhibitor comprises a compound of Formula (101) or (103):

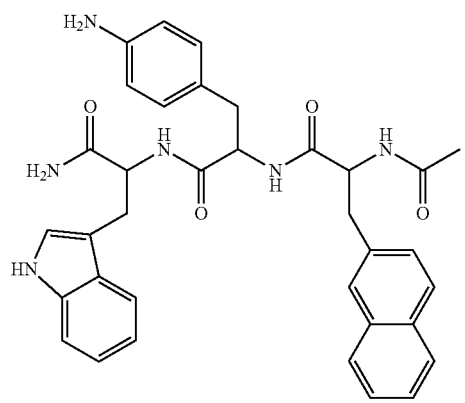

Formula (101)

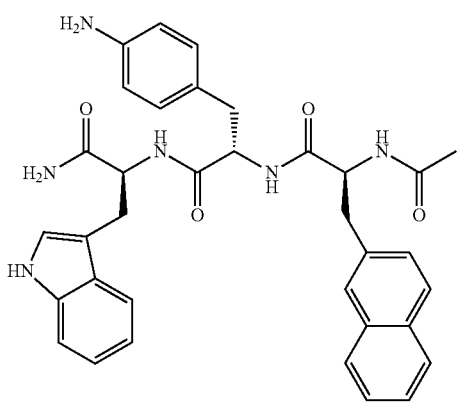

Formula (103)

More preferably, the inhibitor comprises a compound of Formula (101a) or (103a):

Formula (101a)

-continued

Formula (103a)

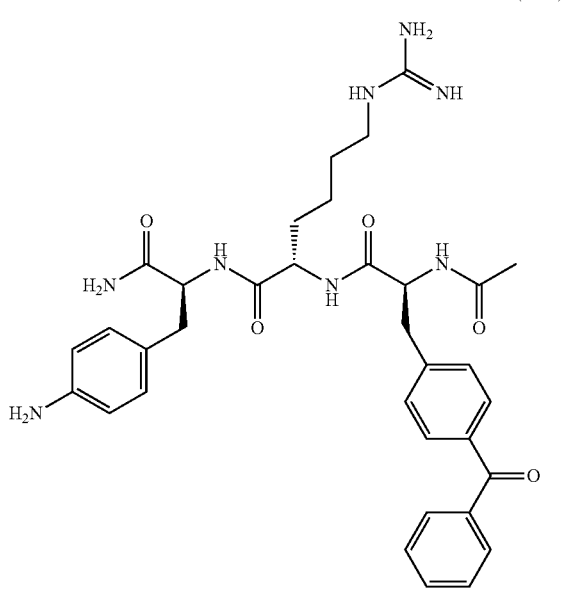

It will be appreciated that compounds of Formula (101a) and (103a) correspond to compounds Tri02 and Tri04, respectively, which are discussed in the Examples. Hence, in a further aspect, there is provided an inhibitor as defined herein, for use in treating, ameliorating or preventing cancer or metastatic disease, preferably wherein the inhibitor is Formula (101a) or (103a).

In one preferred embodiment, the inhibitor comprises an antibody or antigen-binding fragment thereof, i.e. a T14-neutralising antibody. The antibody or antigen-binding fragment thereof preferably blocks T14 interaction with the allosteric site on the alpha-7 receptor. Preferably, the antibody binds to T14, thereby forming a complex, which is unable to bind to the receptor to cause toxicity.

The antibody or antigen-binding fragment thereof may be polyclonal or monoclonal. The antibody or antigen-binding fragment thereof may be generated in a rabbit, mouse or rat.

Preferably, the antibody or antigen-binding fragment thereof specifically binds to SEQ ID No:3. Preferably, the antibody or antigen-binding fragment thereof specifically binds to one or more amino acid in the C-terminus of SEQ ID No:3. Preferably, the antibody or antigen-binding fragment thereof specifically binds to one or more amino acid in SEQ ID No: 5 (i.e. SYMVHWK, which are the C-terminal amino acids numbers 7-14 of SEQ ID No: 3). Preferably, the antibody or antigen-binding fragment thereof specifically binds to a C-terminal lysine (K) residue in the epitope.

The inventors have surprisingly observed that the C-terminal amino acid sequence VHWK in SEQ ID No:3, which is described herein as SEQ ID No. 6 (i.e. the C-terminal amino acids numbers 10-14 of SEQ ID No.3), acts as an epitope for the antibody or antigen-binding fragment thereof. Accordingly, more preferably the antibody or antigen-binding fragment thereof specifically binds to one or more amino acid in SEQ ID No.6. Most preferably, the antibody or antigen-binding fragment thereof specifically binds to SEQ ID No.6. Hence, it will be appreciated that the epitope to which the antibody binds comprises or consists of SEQ ID No: 6.

Based on the discovery of the VHWK epitope (SEQ ID No: 6) within the T14 peptide, the inventors believe that these sequences can be used as an antigen for the production of useful antibodies. As described in the Examples, the T14 peptide (SEQ ID No:3) was cysteine-cross-linked to Keyhole Limpet Hemocyanin (KLH) acting as a carrier protein which stimulates an immune response in the host. The KLH protein cross-linked to T14 is referred to herein as SEQ ID No:7, i.e. CAEFHRWSSYMVHWK (the C was added to link KLH to the A at the N-terminus of the T14 peptide).

Preferably, the antibody or antigen-binding fragment thereof does not bind to SEQ ID No:2. Preferably, the antibody or antigen-binding fragment thereof does not bind to SEQ ID No:4.

Polyclonal antibodies may be produced as polyclonal sera by injecting antigen into animals. Preferred polyclonal antibodies may be raised by inoculating an animal (e.g. a rabbit) with antigen (e.g. T14 or fragments thereof, including the C-terminus) using techniques known to the art. For example, the antibody or antigen-binding fragment thereof may be obtained by immunising a host animal with SEQ ID No:3, and then collecting the antibody or antigen-binding fragment thereof. The host animal is most preferably a rabbit.

In another preferred embodiment, the inhibitor comprises a monoclonal antibody or an antigen-binding fragment thereof. Preferred monoclonal antibodies may be raised using hybridoma technology using T14 or fragments thereof as antigen. Preferably, the antibody of the invention is a human antibody. As used herein, the term "human antibody" can mean an antibody, such as a monoclonal antibody, which comprises substantially the same heavy and light chain CDR amino acid sequences as found in a particular human antibody exhibiting immunospecificity for SEQ ID No:3. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids. Such a human antibody maintains its function of selectively binding to SEQ ID No:3.

Conventional hybridoma techniques may be used to raise the antibodies. The antigen used to generate monoclonal antibodies may be the whole T14 protein or a fragment thereof. Preferred fragments for generating the antibodies may also be the peptides discussed above, and particularly SYMVHWK (SEQ ID No: 5) or VHWK (SEQ ID No: 6). It is preferred that the antibody is a γ-immunoglobulin (IgG).

Another preferred inhibitor according to the invention is an inactive peptide fragment of T14 peptide which will compete with endogenous T14 and thereby reduce its activity. For instance, truncation mutants of T14 that do not bind to the allosteric site on the alpha-7 receptor and which inhibit the ability of T14 to interact with the allosteric site on the alpha-7 receptor may also be used as inhibitors of the invention.

In another embodiment, the inhibitor may prevent or reduce post-translational cleavage of acetyl cholinesterase enzyme to form the T14 peptide, i.e. (d) above. For example, the inhibitor according to the invention may be a gene-silencing molecule configured to block or disrupt enzymatic cleavage of acetyl cholinesterase polypeptide into T14.

The term "gene-silencing molecule" can mean any molecule that interferes with the expression of the T14 peptide. Such molecules include, but are not limited to, RNAi molecules, including siNA, siRNA, miRNA, ribozymes and antisense molecules.

As discussed above, the gene encoding acetylcholinesterase is expressed and translated into the protein shown as SEQ ID NO: 1. Post-translational modifications of SEQ ID No:1 can include cleavage by a protease to create T14 (SEQ ID No:3). Accordingly, in a preferred embodiment, the inhibitor comprises a gene-silencing molecule which reduces or prevents expression of the protease responsible for cleaving off T15 (SEQ ID No:4) from T30 to create T14.

In another embodiment, the inhibitor may inhibit of T14 translocation to the alpha-7 receptor (i.e. (e) above).

It will be appreciated that inhibitors according to the invention may be used in a medicament, which may be used as a monotherapy (i.e. use of the T14 inhibitor alone), for treating, ameliorating, or preventing cancer or metastasis. Alternatively, the T14 inhibitor may be used as an adjunct to, or in combination with, known therapies for treating, ameliorating, or preventing cancer or metastasis, such as radiotherapy or chemotherapy, or any of the known anticancer drugs, such as Lapatinib.

The inhibitors according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the inhibitor to the target site, for example across the blood-brain barrier when treating brain tumours.

Inhibitors according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with inhibitors used according to the invention is required and which would normally require frequent administration (e.g. at least daily injection).

In a preferred embodiment, medicaments according to the invention may be administered to a subject by injection into the blood stream or directly into a site requiring treatment. For example, the medicament may be administered by injection into the blood stream. Injections may be intravenous (bolus or infusion) or subcutaneous (bolus or infusion), or intradermal (bolus or infusion).

It will be appreciated that the amount of the inhibitor that is required is determined by its biological activity and bioavailability, which in turn depends on the mode of administration, the physiochemical properties of the inhibitor and whether it is being used as a monotherapy or in a combined therapy. The frequency of administration will also be influenced by the half-life of the inhibitor within the subject being treated. Optimal dosages to be administered may be determined by those skilled in the art, and will vary with the particular inhibitor in use, the strength of the pharmaceutical composition, the mode of administration, and the advancement of the cancer or metastasis. Additional factors depending on the particular subject being treated will result in a need to adjust dosages, including subject age, weight, gender, diet, and time of administration.

Generally, a daily dose of between 0.001 µg/kg of body weight and 10 mg/kg of body weight, or between 0.01 µg/kg of body weight and 1 mg/kg of body weight, of the inhibitor according to the invention may be used for treating, ameliorating, or preventing cancer or metastasis, depending upon which inhibitor is used.

The inhibitor may be administered before, during or after onset of cancer. Daily doses may be given as a single administration (e.g. a single daily injection or inhalation of a nasal spray). Alternatively, the inhibitor may require administration twice or more times during a day. As an example, inhibitors may be administered as two (or more depending upon the severity of the cancer or metastasis being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of inhibitor according to the invention to a patient without the need to administer repeated doses.

Known procedures, such as those conventionally employed by the pharmaceutical industry (e.g. in vivo experimentation, clinical trials, etc.), may be used to form specific formulations of the inhibitor according to the invention and precise therapeutic regimes (such as daily doses of the agents and the frequency of administration). The inventors believe that they are the first to suggest an anti-cancer treatment composition, based on the use of inhibitors of the invention.

Hence, in a third aspect of the invention, there is provided an anti-cancer or anti-metastatic pharmaceutical composition comprising a therapeutically effective amount of the inhibitor according to the first aspect, and optionally a pharmaceutically acceptable vehicle.

The invention also provides in a fourth aspect, a process for making the anti-cancer or anti-metastatic pharmaceutical composition according to the third aspect, the process comprising combining a therapeutically effective amount of inhibitor according to the first aspect, with a pharmaceutically acceptable vehicle.

The inhibitor of the first aspect inhibits the synthesis and/or activity of a peptide of SEQ ID No: 3, as described above.

A "subject" may be a vertebrate, mammal, or domestic animal. Hence, medicaments according to the invention may be used to treat any mammal, for example livestock (e.g. a horse), pets, or may be used in other veterinary applications. Most preferably, however, the subject is a human being.

A "therapeutically effective amount" of the inhibitor is any amount which, when administered to a subject, is the amount of active agent that is needed to treat the cancer or metastasis, or produce the desired effect. The inhibitor may be used as an adjuvant for the treatment of solid or metastatic tumours, for example with chemotherapy or radiotherapy. This means that lower doses and exposure times of chemotherapy and/or radiotherapy are required.

For example, the therapeutically effective amount of inhibitor used may be from about 0.001 mg to about 800 mg, and preferably from about 0.01 mg to about 500 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. However, the pharmaceutical vehicle may be a liquid, and the pharmaceutical composition is in the form of a solution. Liquid pharmaceutical compositions, which are sterile solutions or suspensions, can be utilized by, for example, intramuscular, intrathecal, epidural, intraperitoneal, intravenous and particularly subcutaneous injection.

The inhibitor and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The inhibitor used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Knowledge of the surprising role that T14 plays in cancer, and especially metastatic disease, as evidenced by the CD44 data in Example 2, has enabled the inventors to develop a screen for identifying whether or not test compounds are putative inhibitors for treating, preventing or ameliorating cancer or metastasis.

Thus, according to a fifth aspect of the present invention, there is provided a method of screening a candidate compound to test whether or not the compound has efficacy for treating, preventing or ameliorating cancer or metastatic disease, the method comprising:
(i) exposing a biological system to the candidate compound;
(ii) detecting the concentration, expression or activity of the T14 peptide of SEQ ID No:3 in the biological system; and
(iii) comparing the concentration, expression or activity of T14 peptide in the biological system treated with the compound relative to the concentration, expression or activity found in a control biological system that was not treated with the compound,
wherein a compound with efficacy for treating, preventing or ameliorating cancer or metastatic disease decreases the concentration, expression or activity of the T14 peptide relative to the control.

It will be appreciated that the method according to the fifth aspect of the invention may be adapted such that it can be used to test whether or not a compound actually causes cancer or metastasis.

Therefore, according to a sixth aspect, there is provided a method of screening a compound to test whether or not the compound causes cancer, the method comprising:
(i) exposing a biological system to the test compound;
(ii) detecting the concentration, expression or activity of the T14 peptide of SEQ ID No:3 in the biological system; and
(iii) comparing the concentration, expression or activity of the T14 peptide in the biological system treated with the compound relative to the concentration, expression or activity of the T14 peptide found in a control biological system that was not treated with the compound,
wherein a compound that is carcinogenic or which increases metastasis increases the concentration, expression or activity of the T14 peptide relative to the control.

The screening methods or assays of the invention are based upon the inventors' realisation that the extent of T14 expression and/or activity is closely related to the development of cancer and metastasis. The screening method of the fifth aspect of the invention is particularly useful for screening libraries of compounds to identify compounds that may be used as anti-cancer or anti-metastasis agents used according to the first aspect of the invention. The sixth aspect of the invention may be used to identify compounds that are carcinogenic, and which should be avoided. Accordingly, the screen according to the sixth aspect of the invention may be used for environmental monitoring (e.g. to test effluents from factories) or in toxicity testing (e.g. to test the safety of putative pharmaceuticals, cosmetics, foodstuffs and the like).

The term "biological system" can mean any experimental system that would be understood by a skilled person to provide insight as to the effects a compound may have on the concentration, expression or activity of the T14 peptide in the physiological environment. The system may comprise: (a) an experimental test subject when an in vivo test is to be employed; (b) a biological sample derived from a test subject (for instance: blood or a blood fraction (e.g. serum or plasma), lymph or a cell/biopsy sample); (c) a cell line model (e.g. a cell naturally expressing the T14 peptide or a cell engineered to express T14); or (d) an in vitro system that contains T14 or its gene and simulates the physiological environment such that the concentration, expression or activity of the T14 peptide can be measured.

The screen preferably assays biological cells or lysates thereof. When the screen involves the assay of cells, they may be contained within an experimental animal (e.g. a mouse or rat) when the method is an in vivo based test. Alternatively, the cells may be in a tissue sample (for ex vivo based tests) or the cells may be grown in culture. It will be appreciated that such cells should express, or may be induced to express, functional (i.e. toxic) T14. It is also possible to use cells that are not naturally predisposed to produce T14 provided that such cells are transformed with an expression vector. Such cells represent preferred test cells for use according to the fifth or sixth aspects of the invention. This is because animal cells or even prokaryotic cells may be transformed to express human T14 peptide and therefore represent a good cell model for testing the efficacy of candidate drugs for use in human therapy.

It is most preferred that biological cells used according to the screening methods of the present invention are derived from a subject and in particular xenograft models of cancer (e.g. mouse xenografts).

With regards to "detecting the concentration, expression or activity of the T14 peptide" according to the screening methods of the present invention, the term "activity" can mean the detection of T14 interaction with the allosteric site on the alpha-7 receptor or determination of an end-point physiological effect. The term "expression" can mean detection of the T14 protein in any compartment of the cell (e.g. in the cytosol, the Endoplasmic Reticulum or the Golgi Apparatus).

Expression of T14 in the biological system may be detected by Western Blot, immuo-precipitation (IP) or co-IP, or immunohistochemistry.

The screening methods may also be based upon the use of cell extracts comprising T14 peptide. Such extracts are preferably derived from the cells described above.

The concentration, expression or activity of the T14 peptide may be measured using a number of conventional techniques. The test may be an immunoassay-based test. For instance, labelled antibodies may be used in an immunoassay to evaluate binding of a compound to T14 in the sample. T14 peptide may be isolated and the amount of label bound to it detected. A reduction in bound label (relative to controls) would suggest that the test compound competes with the label for binding to T14 and that it was also a putative anti-cancer or anti-metastasis agent. Alternatively, a functional activity measuring T14 peptide activity may be employed.

Furthermore, molecular biology techniques may be used to detect T14 peptide in the screen. For instance, cDNA may be generated from mRNA extracted from tested cells or subjects and primers designed to amplify test sequences used in a quantitative Polymerase Chain Reaction to amplify from cDNA. When a subject is used (e.g. an animal model or even an animal model engineered to express human T14), the test compound should be administered to the subject for a pre-determined length of time and then a sample taken from the subject for assaying concentration, expression or activity of the T14 peptide. The sample may for instance be blood or biopsy tissue.

As discussed in the Examples, the inventors have clearly shown that toxic T14 peptide is readily detectable outside cancer cells (i.e. within the cell culture media), whereas AChE and alpha-7 nicotinic receptor were not. Moreover, the inventors have demonstrated a strong correlation between the metastatic marker (CD44) and the toxic molecule T14 peptide. This correlation holds true for both within the cancer cell membrane and within the cancer cell cytosol. Accordingly, the inventors believe that T14 represents a robust biomarker for cancer per se, and in particular, for metastasis.

Thus, according to a seventh aspect of the invention, there is provided the use of a peptide of SEQ ID No: 3, or a fragment or variant thereof, as a diagnostic or prognostic biomarker for cancer or metastatic disease.

Most preferably, the invention provided use of a peptide of SEQ ID No: 3, or a fragment or variant thereof, as a diagnostic or prognostic biomarker for metastatic disease.

According to an eighth aspect, there is provided a method for diagnosing an individual who suffers from cancer or metastatic disease, or has a pre-disposition thereto, or for providing a prognosis of an individual's condition, the method comprising detecting, in a sample obtained from the individual, for the presence of a peptide of SEQ ID No: 3, or a fragment or variant thereof, wherein the presence of the peptide of SEQ ID No: 3, or a fragment or variant thereof, means that the individual suffers cancer or metastatic disease, or has a pre-disposition thereto, or the individual's condition has a negative prognosis.

According to a ninth aspect of the invention, there is provided a kit for diagnosing a subject suffering from cancer or metastatic disease, or a pre-disposition thereto, or for providing a prognosis of the subject's condition, the kit comprising detection means for determining the concentration of a peptide of SEQ ID No: 3, or a fragment or variant thereof, present in a sample from a test subject, wherein presence of the peptide of SEQ ID No: 3, or a fragment or variant thereof, in the sample suggests that the subject suffers from cancer or metastatic disease, or a pre-disposition thereto.

Advantageously, the use, method and kit of the invention enable the diagnosis or prognosis of an individual who suffers from cancer or metastatic disease, or has a pre-disposition thereto, most preferably metastasis. The inventors have found that the toxic T14 peptide is a robust biomarker for identifying individuals who suffer from cancer or metastatic disease. Thus, individuals diagnosed with cancer or metastatic disease, or who have a predisposition thereto, or have a negative prognosis, according to the use, methods and kit of the invention, can benefit from the early therapeutic treatment in order to prevent the onset of cancer or metastatic disease.

The individual may be a vertebrate, mammal, or domestic animal. Most preferably, however, the individual is a human being. The individual may be a child or adult. Preferably, the method is carried out in vitro.

Preferably, the sample comprises a biological sample. The sample may be any material that is obtainable from an individual from which protein is obtainable. Furthermore, the sample may be blood, plasma, serum, spinal fluid, urine, sweat, saliva, tears, breast aspirate, prostate fluid, seminal fluid, vaginal fluid, stool, cervical scraping, cytes, amniotic fluid, intraocular fluid, mucous, moisture in breath, animal tissue, cell lysates, tumour tissue, hair, skin, buccal scrapings, lymph, interstitial fluid, nails, bone marrow, cartilage, prions, bone powder, ear wax, or combinations thereof.

The sample may comprise blood, urine, tissue etc. Most preferably, the sample comprises a blood sample. The blood may be venous or arterial blood.

The kit may comprise a sample collection container for receiving the extracted sample. Blood samples may be assayed for T14 levels immediately. Alternatively, the blood sample may be stored at low temperatures, for example in a fridge or even frozen before the T14 assay is conducted. Detection of T14 may be carried out on whole blood. Preferably, however, the blood sample comprises blood serum. Preferably, the blood sample comprises blood plasma.

The blood may be further processed before the T14 assay is performed. For instance, an anticoagulant, such as citrate (such as sodium citrate), hirudin, heparin, PPACK, or sodium fluoride may be added. Thus, the sample collection container may contain an anticoagulant in order to prevent the blood sample from clotting. Alternatively, the blood sample may be centrifuged or filtered to prepare a plasma or serum fraction, which may be used for analysis. Hence, it is preferred that the T14 is analysed or assayed in a blood plasma or a blood serum sample. It is preferred that T14 concentration is measured in vitro from a blood serum sample or a plasma sample taken from the individual.

Preferably, the kit or method is used to identify the presence or absence of T14-positive cells (i.e. cells comprising SEQ ID No:3) in the sample, or determine the concentration thereof in the sample. The detection means may comprise an assay adapted to detect the presence and/or absence of T14-positive cells in the sample. The kit or method may comprise the use of a positive control and/or a negative control against which the assay may be compared. For example, the kit preferably comprises a reference for the concentration of T14-positive cells in a sample from an individual who does (i.e. positive control) suffer from cancer or metastatic disease and/or a reference for the concentration of T14-negative cells in a sample from someone who does not (i.e. a negative control) suffer from cancer or metastatic disease.

T14 peptide (SEQ ID No: 3) may be assayed by a number of ways known to one skilled in the art. For example, preferably, immunoassays may be employed to measure T14 peptide levels. However, it will be appreciated that non-immuno based assays may be employed, for example, labelling a compound having affinity with a ligand of the T14 peptide molecule, and then assaying for the label.

T14 peptide may also be determined with Western Blot analysis. Hence, immunoassays and Western blot analyses may be used to determine the total protein level of T14 peptide. T14 peptide concentration may also be detected by enzyme-linked immunosorbent assay (ELISA), fluorometric assay, chemiluminescent assay, or radioimmunoassay analyses.

The kit may further comprise a label which may be detected. The term "label" can mean a moiety that can be attached to the detection means, or fragment thereof. Moieties can be used, for example, for therapeutic or diagnostic procedures. Therapeutic labels include, for example, moieties that can be attached to an antibody or fragment thereof of the invention and used to monitor the binding of the antibody to T14 peptide (i.e. SEQ ID No:3). As described herein the antibody or antigen-binding fragment thereof binds specifically to SEQ ID No:3, or a fragment or variant thereof, and can be used as the detection means, or in the detection means. Preferably, the antibody or antigen-binding fragment thereof does not bind to SEQ ID No:2 (i.e. T30). Preferably, the antibody or antigen-binding fragment thereof does not bind to SEQ ID No:4 (i.e. T15).

Diagnostic labels include, for example, moieties which can be detected by analytical methods. Analytical methods include, for example, qualitative and quantitative procedures. Qualitative analytical methods include, for example, immunohistochemistry and indirect immunofluorescence. Quantitative analytical methods include, for example, immunoaffinity procedures such as radioimmunoassay, ELISA or FACS analysis. Analytical methods also include both in vitro and in vivo imaging procedures. Specific examples of diagnostic labels that can be detected by analytical means include enzymes, radioisotopes, fluorochromes, chemiluminescent markers, and biotin.

Examples 3 and 4 describe ELISA and Western Blot data for T14 in a range of cancer patients. It will be appreciated that the concentration of T14 peptide in cancer patients is highly dependent on a number of factors, for example, how far the cancer has progressed. It will also be appreciated that the concentration of T14 peptide in individuals who do not suffer from cancer may fluctuate to some degree, but that on average over a given period of time, the concentration tends to be substantially constant. In addition, it should be appreciated that the concentration of T14 peptide in one group of individuals who do not suffer from cancer may be different to the concentration of T14 peptide in another group of individuals who do not suffer from cancer. However, the skilled technician will know how to determine the average concentration of T14 peptide in individuals who do not suffer from cancer, and this is referred to as the 'normal' concentration of T14 peptide. The normal concentration corresponds to the reference values discussed above.

T14 peptide serum or T14 peptide plasma concentrations may be measured by double-antibody sandwich ELISA, which will be known to the skilled technician. The ELISA may comprise using a suitable antibody for coating a microtiter plate. For example, such a suitable antibody may comprise an affinity-purified polyclonal rabbit anti-human T14 peptide antibody. Furthermore, the ELISA may comprise using a suitable antibody for detection. For example, such a suitable antibody may comprise peroxidase-labeled monoclonal mouse anti human T14 peptide antibody. Human T14 peptide, which may be purified from plasma, and which then may be quantified by amino acid analysis, may be used to calibrate a plasma standard using standard techniques known to the skilled technician.

A label can be attached directly to the antibody, or be attached to the secondary binding agent that specifically binds T14. Such a secondary binding agent can be, for example, a secondary antibody. A secondary antibody can be either polyclonal or monoclonal, and of human, rodent or chimeric origin.

Due to current limitations of the assays (both western blot and ELISA), all values in both cases can currently only be considered relative different groups. However, whilst ELISA data may not be totally conclusive, there was a surprisingly clear and significant difference between groups using western blot analysis where poor survival with longer time to first treatment corresponded (P=0.01) to lower levels of T14. Since western blots will measure aggregates of the peptide, these data suggest that there will be more free monomer to act as a signalling molecule in the circulation of those yet to be treated and therefore with poorer prognosis. The fact that data with ELISA is, at present, inconclusive could be that the free monomer that it would be measuring has been taken up and/or is bound to its respective targets, mediating cell migration.

Preferably, therefore, western blot is used to detect T14 and/or quantify T14 levels.

The invention further extends to methods of treatment.

Hence, according to a tenth aspect of the invention, there is provided a method of treating an individual having a susceptibility to developing cancer or metastatic disease, the method comprising:

(i) determining the concentration of a peptide of SEQ ID No: 3, or a fragment or variant thereof, present in a sample from a test subject, wherein presence of the peptide of SEQ ID No: 3, or a fragment or variant thereof, in the sample suggests that the subject suffers from cancer or metastatic disease, or a pre-disposition thereto; and (ii) administering, to the individual, a therapeutic agent or treatment regime that prevents, reduces or delays the development of cancer or metastatic disease.

Examples of suitable therapeutic agents which may be administered include but are not limited to Herceptin. Examples of suitable treatment regimes include radiotherapy or chemotherapy.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID No:1-7, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence, which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No: 1-4.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:

FIG. 1 are Western Blot data showing similar mobility between T14 (A), alpha 7 receptor (B) and AChE (C) in the cell lysate of seven cancer cell lines (CL), i.e. MEC-1, KG1a, H929, MCF-7, MDA-MB-231, CLL, and JJN3, and normal B-lymphocytes acting as control. MDA-MB-231, KG1a, and MEC-1 cells are highly migratory cancer cell lines. H929, JJN3, CLL and MCF-7 are less migratory cancer cell lines. B-lymphocytes are normal, non-cancerous cells. The peptide/protein levels were normalised to total protein (TP) and plotted together for each cell line. Peptide/protein levels were similar within each cell line with the exception of MCF-7 cells in which T14 levels were lower. Between cell lines, the peptide/protein levels were variable. The protein levels of the above were then subsequently quantified, as shown in FIG. 2 and FIG. 5;

FIG. 2 are graphs of the Western Blot data showing variable levels of T14, alpha 7 receptor and AChE in cell lysate between the cancer cell lines, but similar levels within each cell line;

FIG. 3 are graphs based on the Western Blot data shown in FIG. 1. The T14, alpha 7 receptor and AChE levels were normalised to total protein (TP) and the level of each peptide/protein was correlated with the other in x-y plots and linear regression analysis were conducted, displaying lines of best fit (solid line) along with their 95% confidence interval (dotted lines). A): T14 and alpha 7 receptor, $R^2$=0.6262, P=0.0193. B): Alpha 7 receptor and AChE, $R^2$=0.6705, P=0.0129.C): T14 and AChE. The circle in (C) highlights an anomaly data point, which, when excluded, gives a significant positive correlation ($R_u$=0.7032, P=0.0184). The fact that all correlations were significantly linear suggests that the peptide/proteins exist as a complex with a ratio of 1:1:1 (D);

FIG. 4 are Western Blot data showing that T14 was detected in cancer cell culture media of all seven cancer cell lines, but that AChE and alpha7 were not. T14 mobility in the cell media is slightly different from that in the cell lysate.

The protein levels of the above were then subsequently quantified, as shown in FIG. 5;

FIG. 5 are graphs of the Western Blot data showing that T14 concentrations within the cancer cell culture media are significantly greater than the concentrations of cellular T14 peptide/protein levels in MEC-1, KG1a, Normal B lymphocyte and MDA-MB-231 cell lines. No alpha 7 and AChE signals were detected in the cancer culture media. The peptide/protein levels were normalised to total protein (TP) and they were plotted together for each cell line;

FIG. 6 are graphs based on the Western Blot data shown in FIG. 1 and FIG. 4. T14, alpha 7 receptor and AChE levels were normalised to total protein (TP) and the level of T14 within the cancer culture media (extracellular T14) was correlated with each intracellular peptide/protein in x-y plots and linear regression analysis were conducted, displaying lines of best fit (solid line) along with their 95% confidence interval (dotted lines). A): Extracellular T14 and intracellular alpha 7 receptor, $R^2=0.6518$, $P=0.0154$. B): Extracellular T14 and intracellular T14. Cell lines were split into two groups (Dark grey and light grey circles). Dark grey on its own showed $R^2=0.9794$, $P=0.0105$. C): Extracellular T14 and intracellular AChE;

Figure 9:
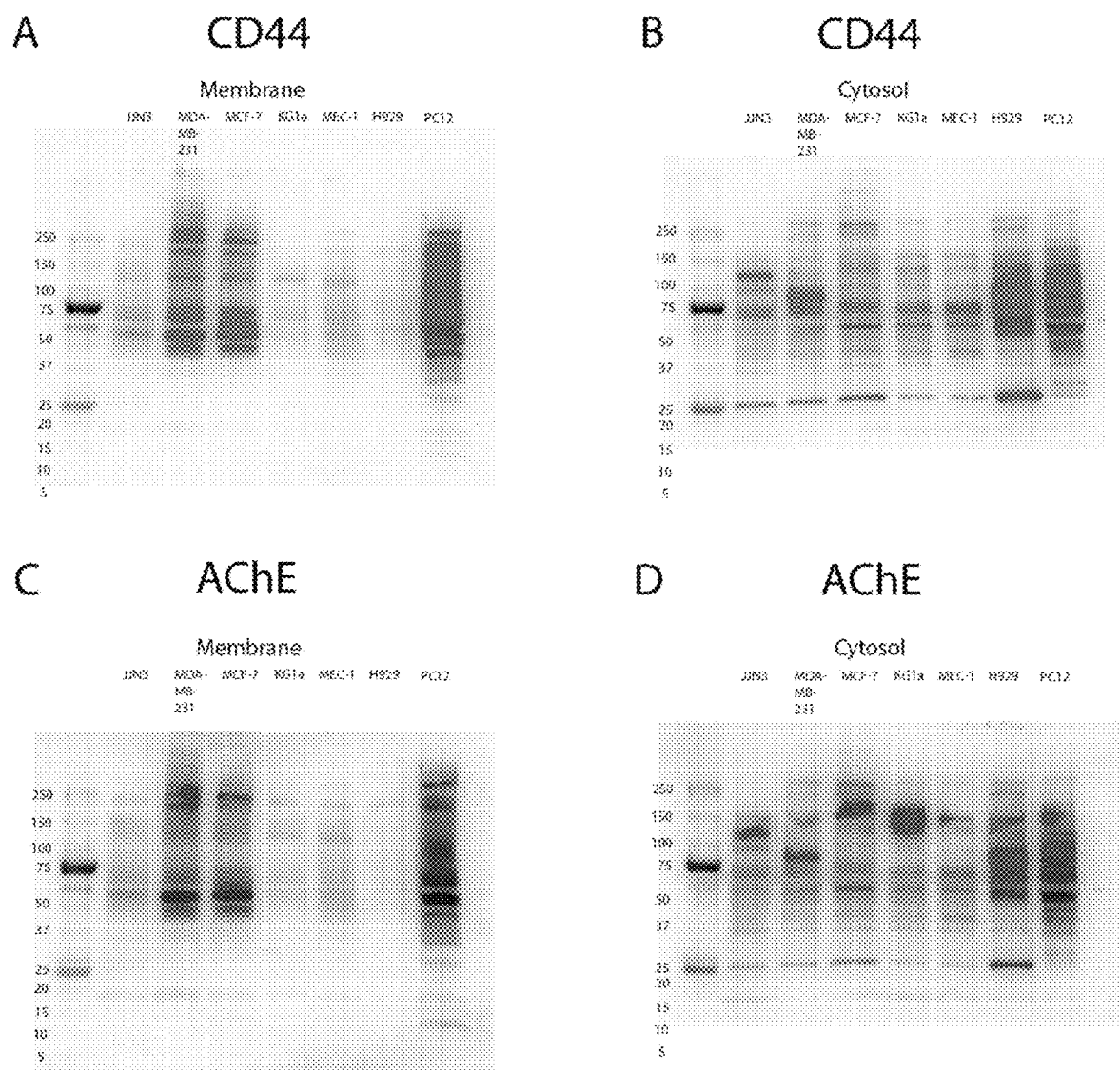
Figure 9:
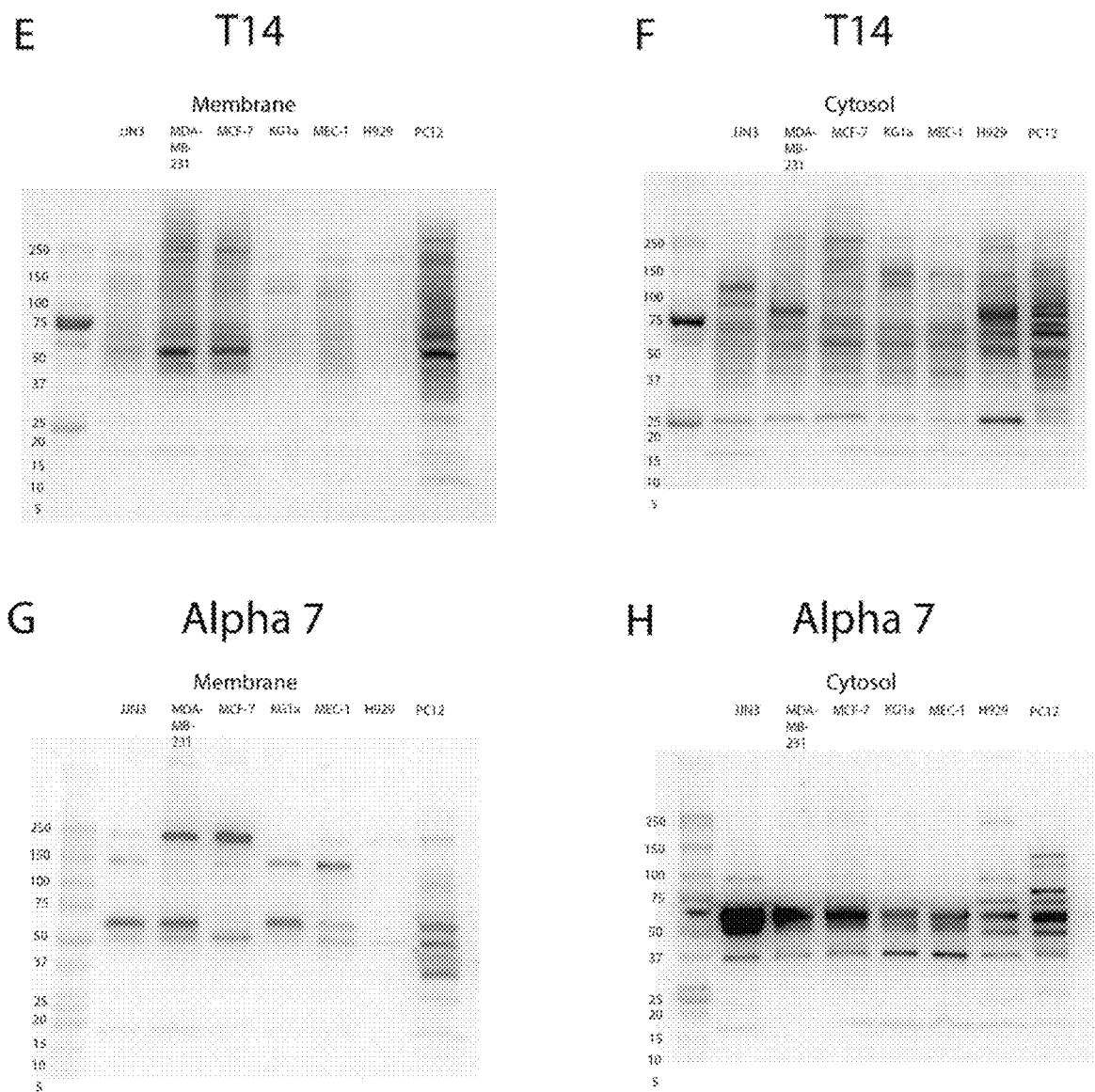
Figure 10:
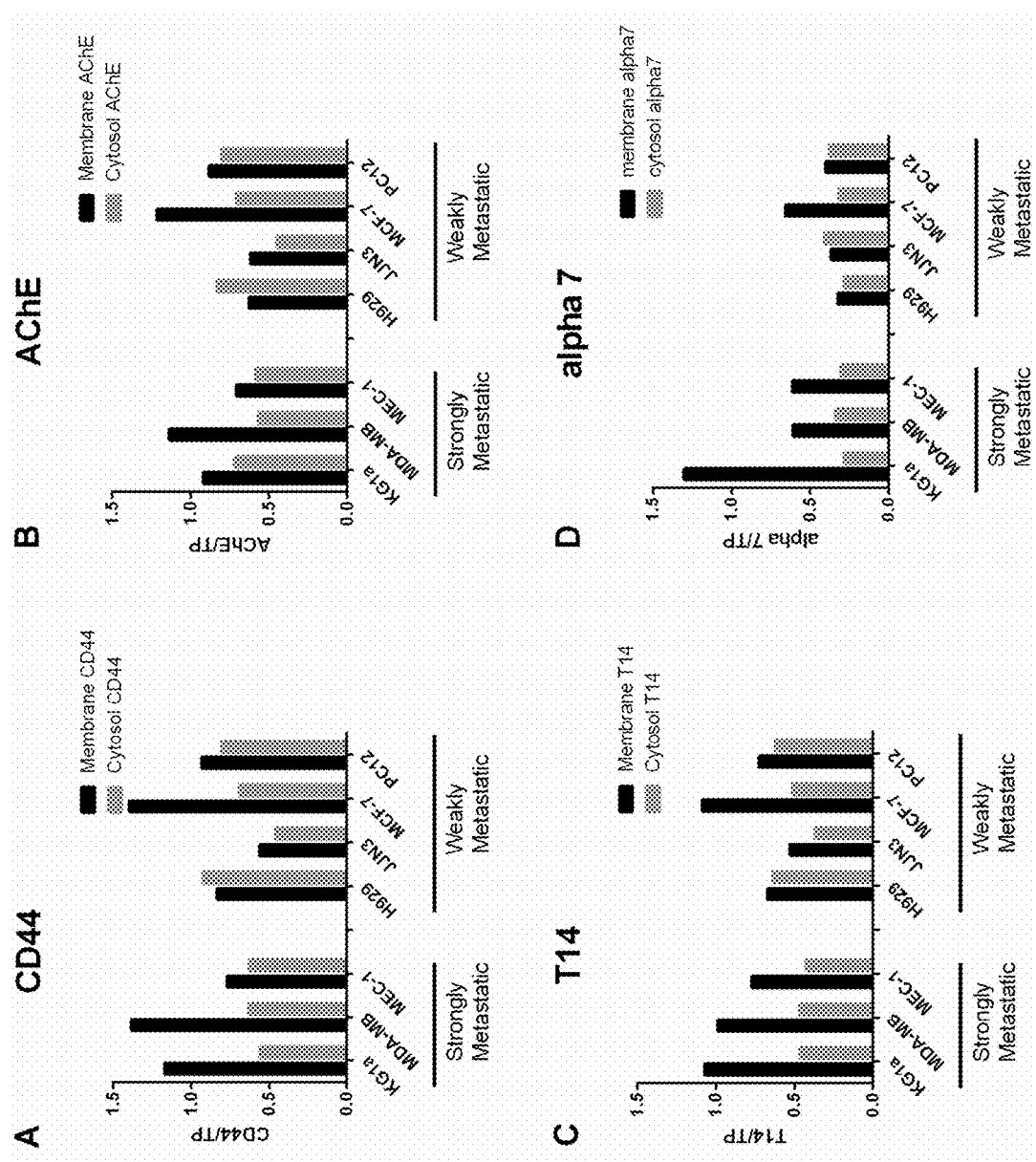
Figure 11:
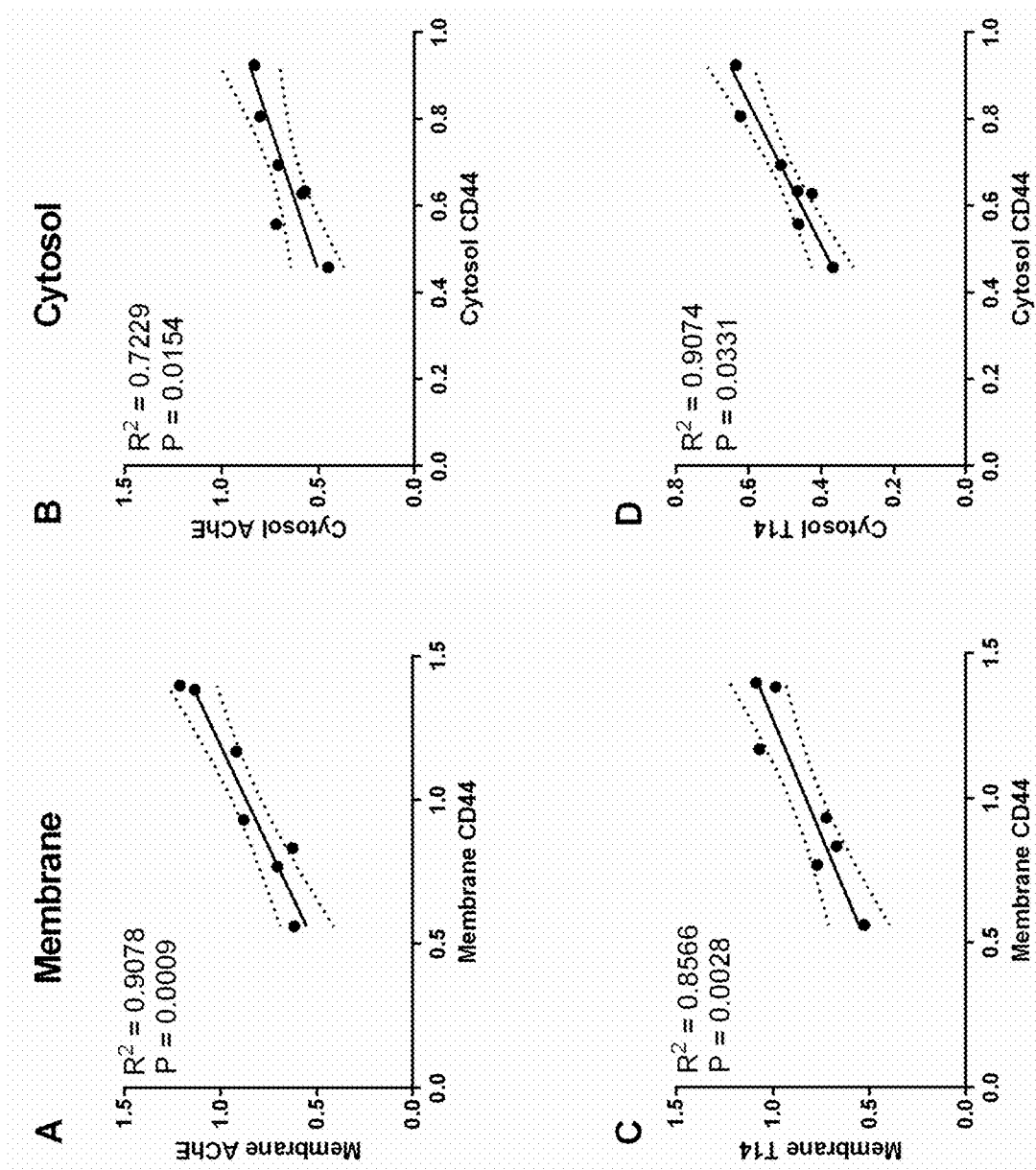
Figure 11:
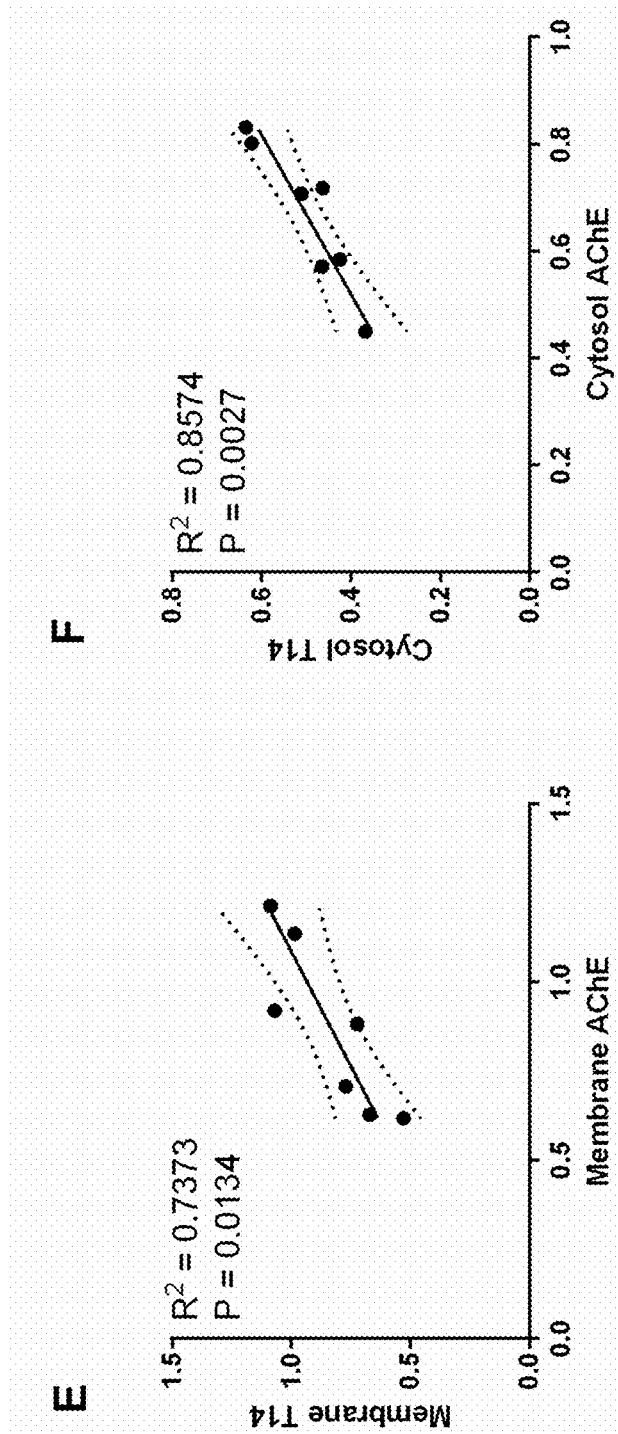
Figure 12:
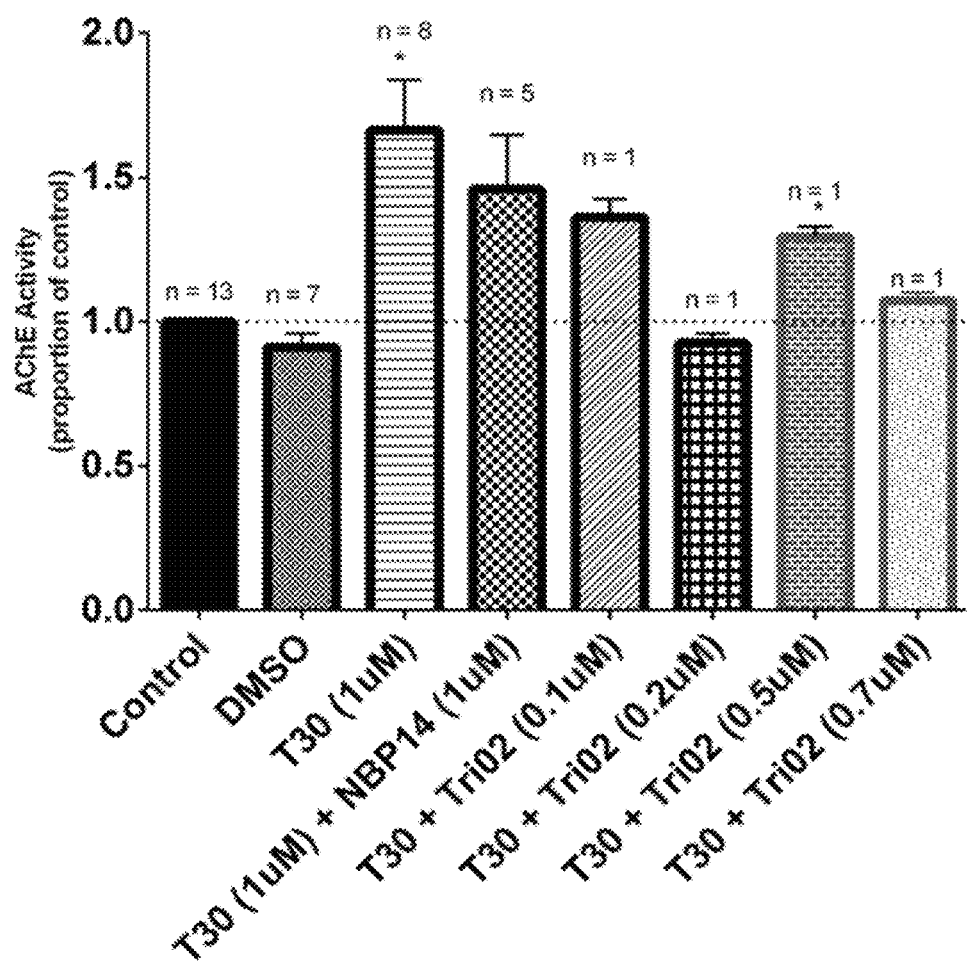
Figure 13:
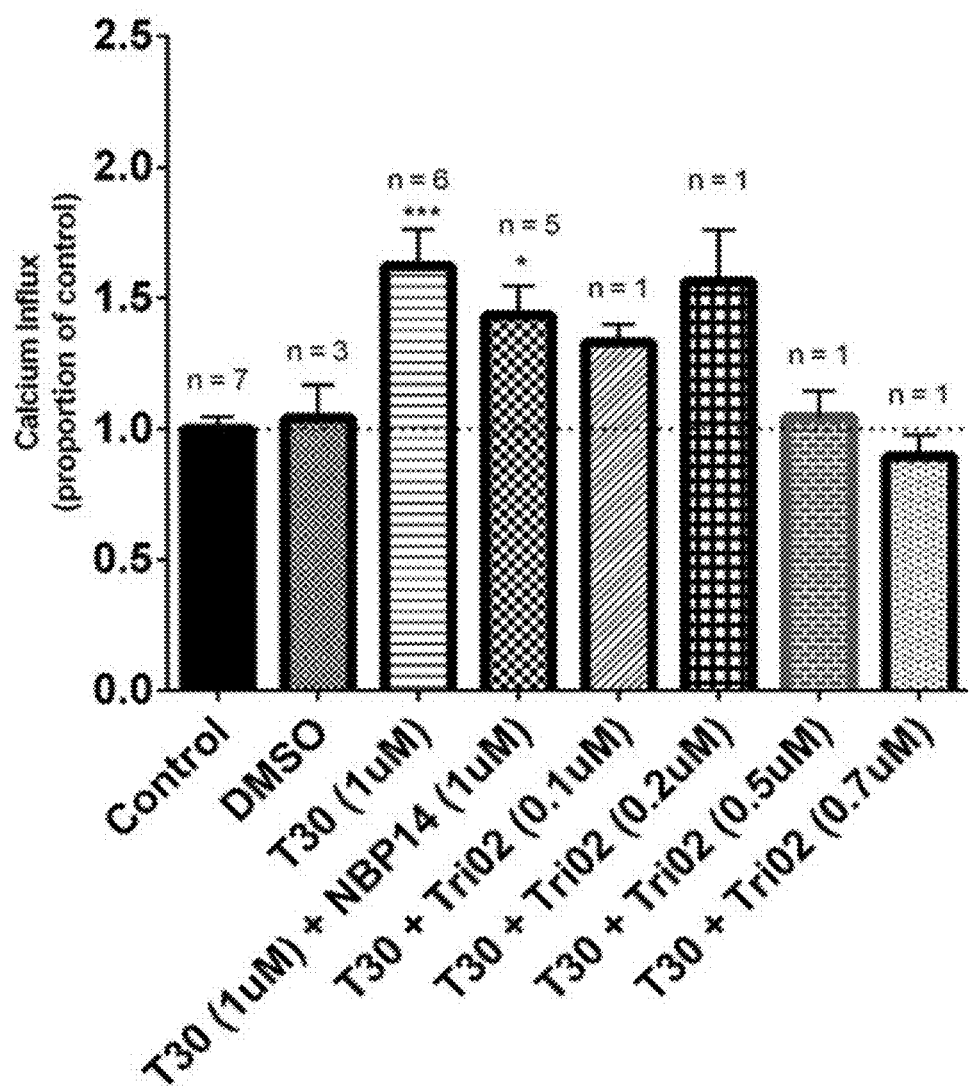
Figure 14:
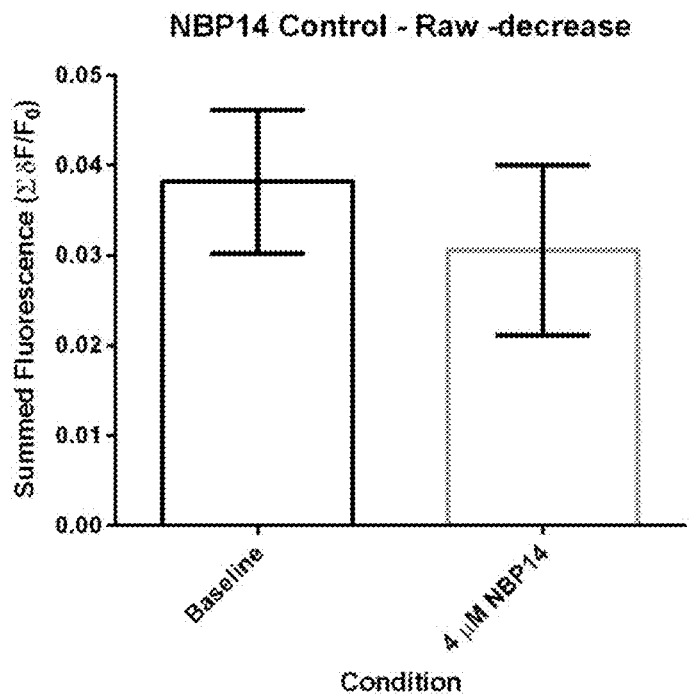
Figure 14:
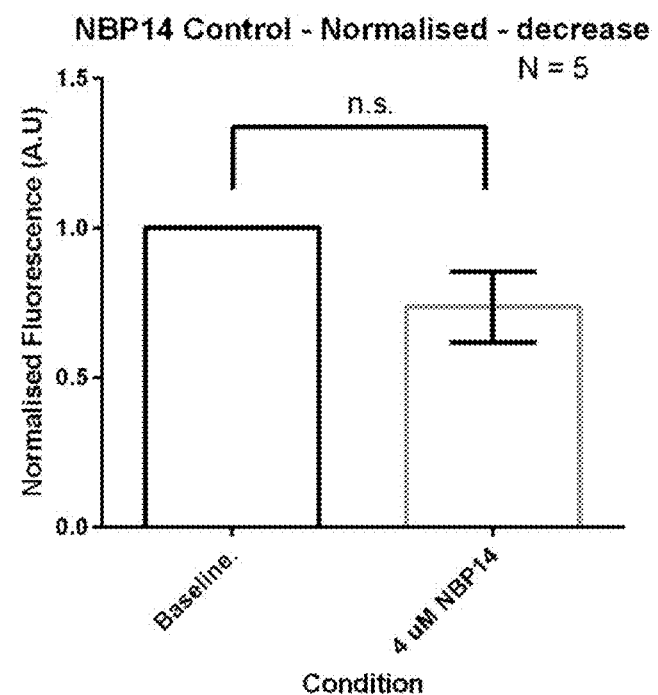
Figure 14:
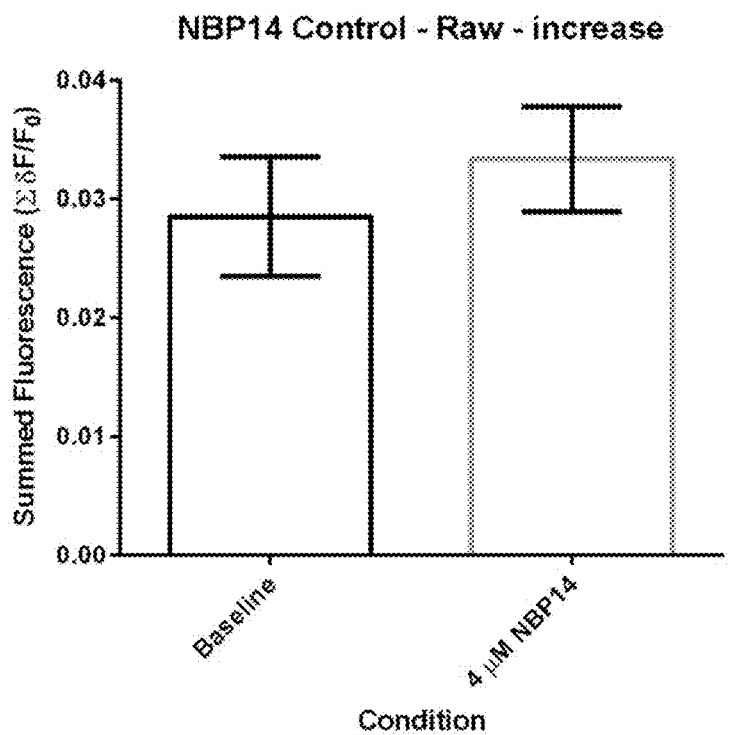
Figure 14:
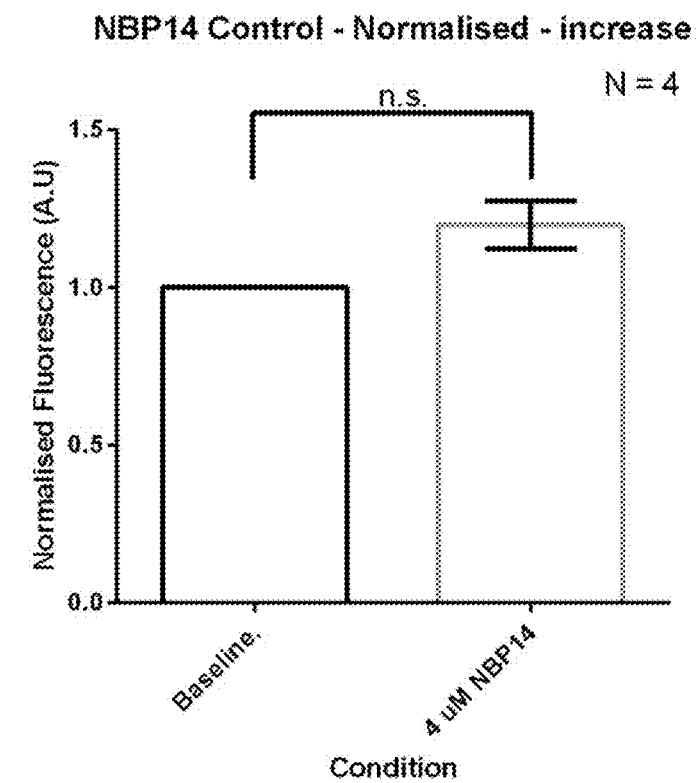
Figure 15:
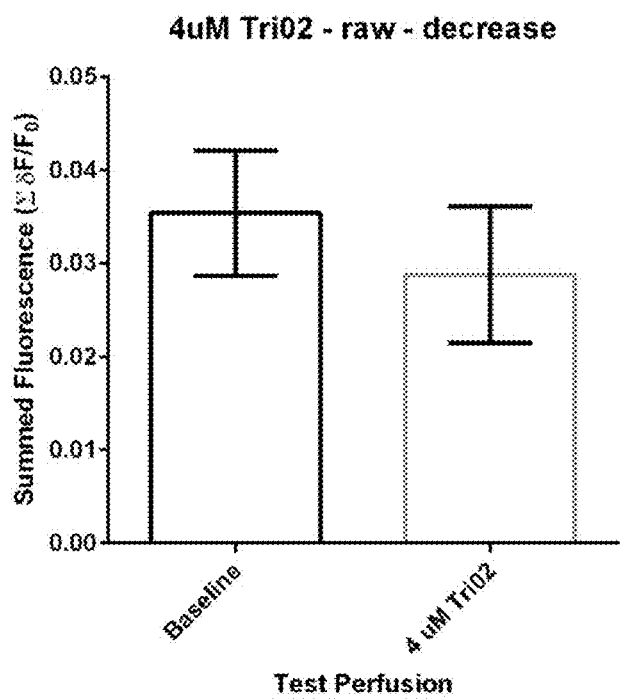
Figure 15:
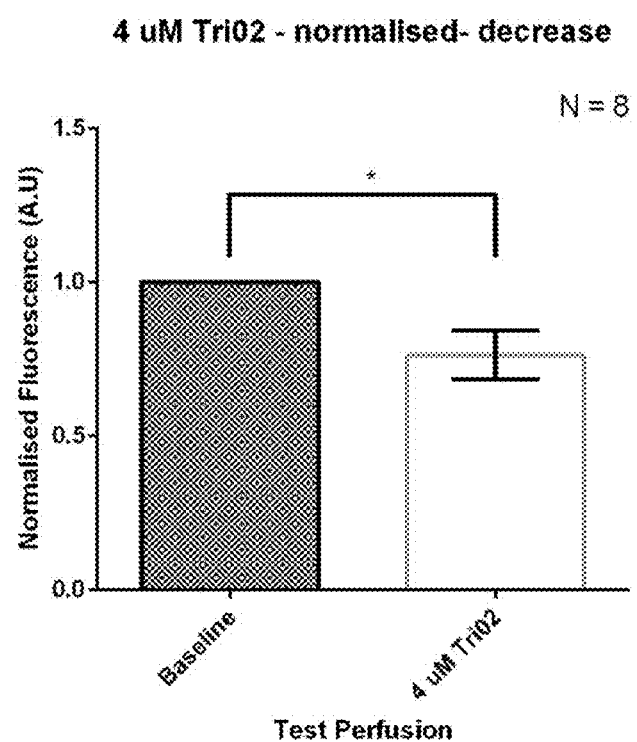
Figure 15:
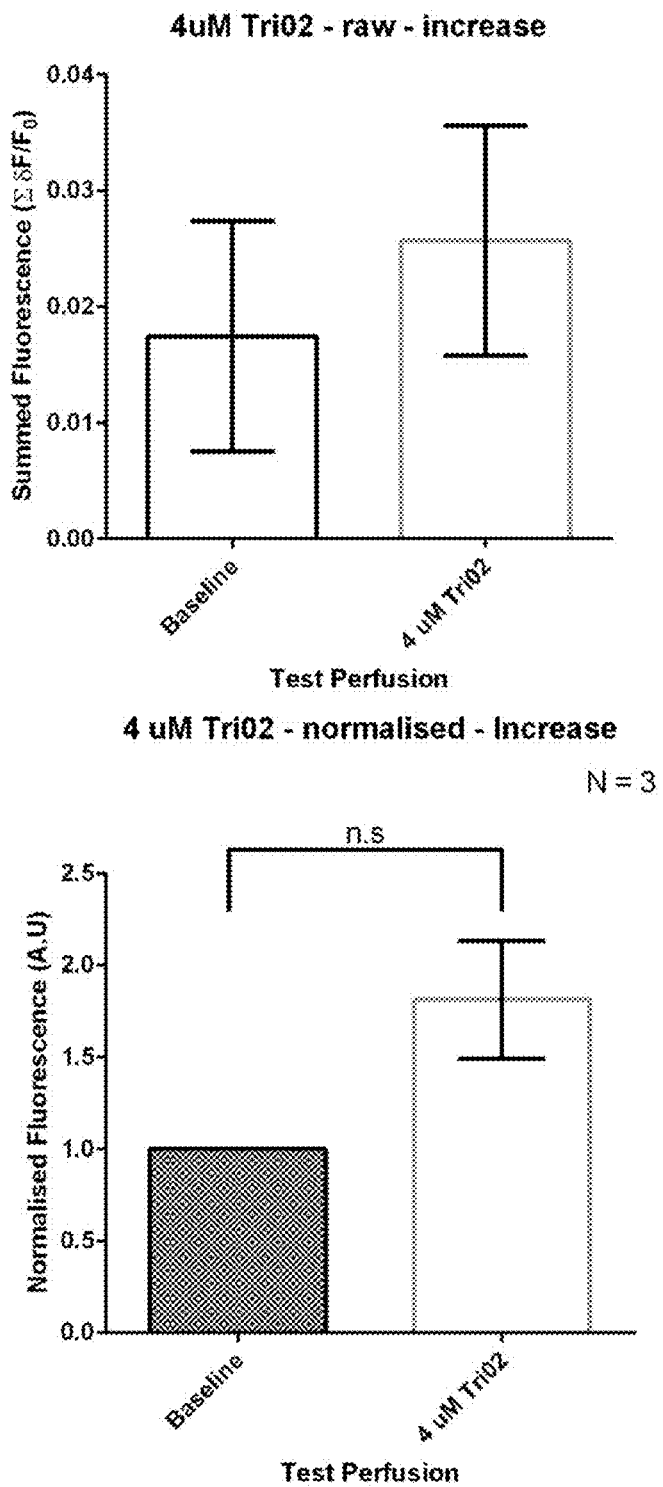
Figure 16:
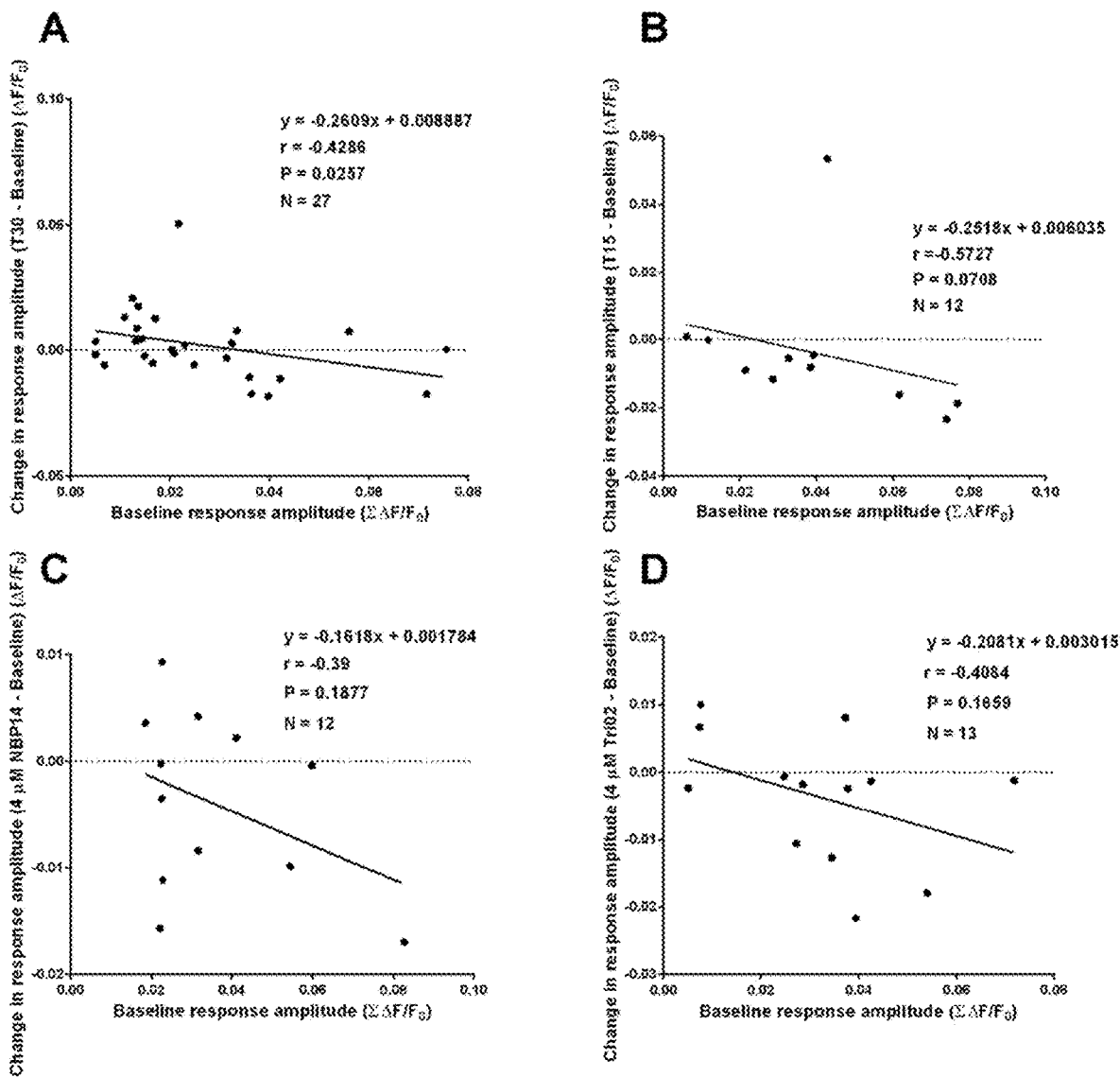
Figure 16:
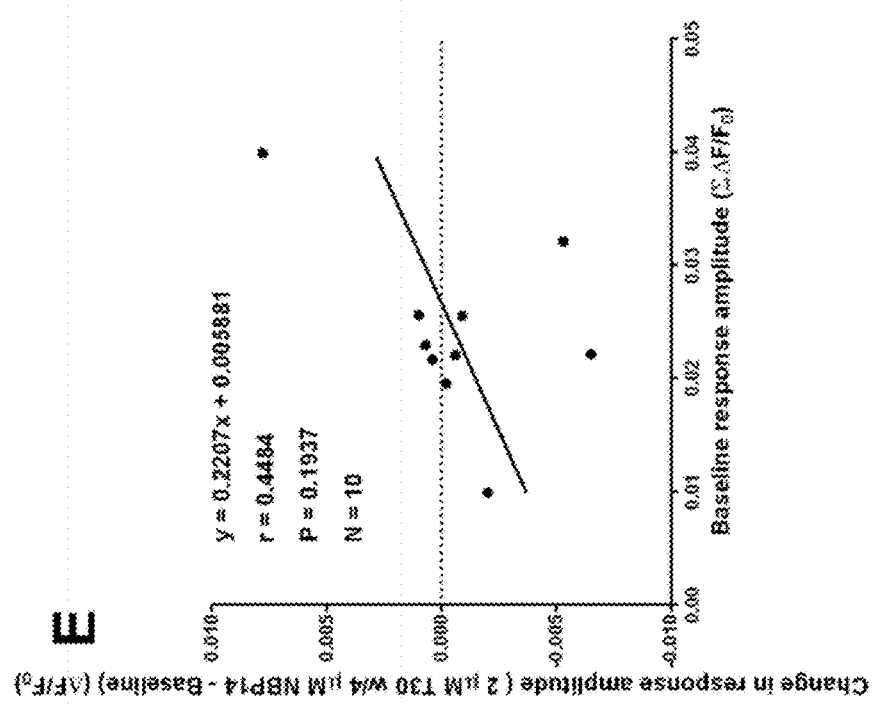
Figure 17:
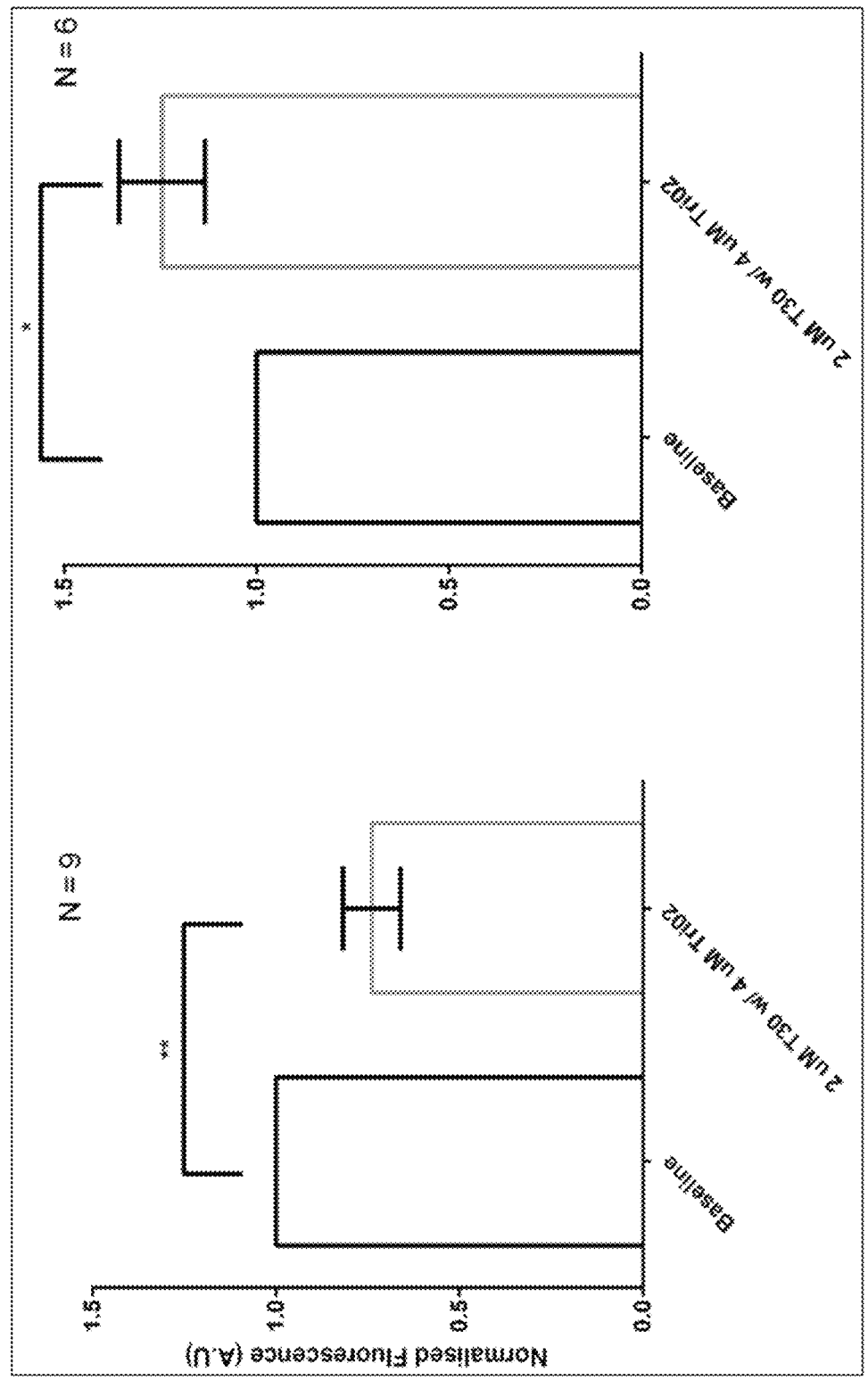
Figure 18:
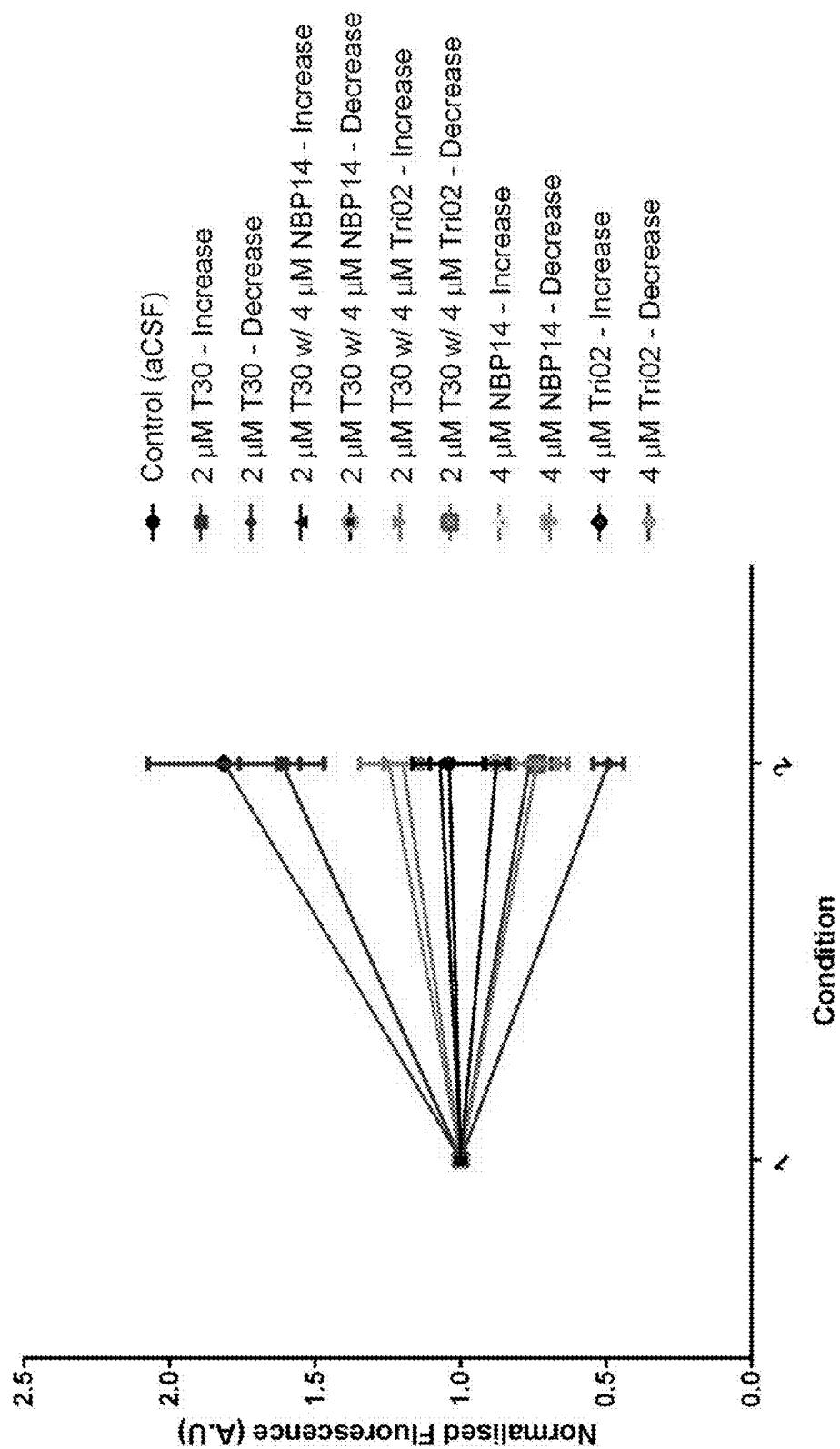
Figure 19:
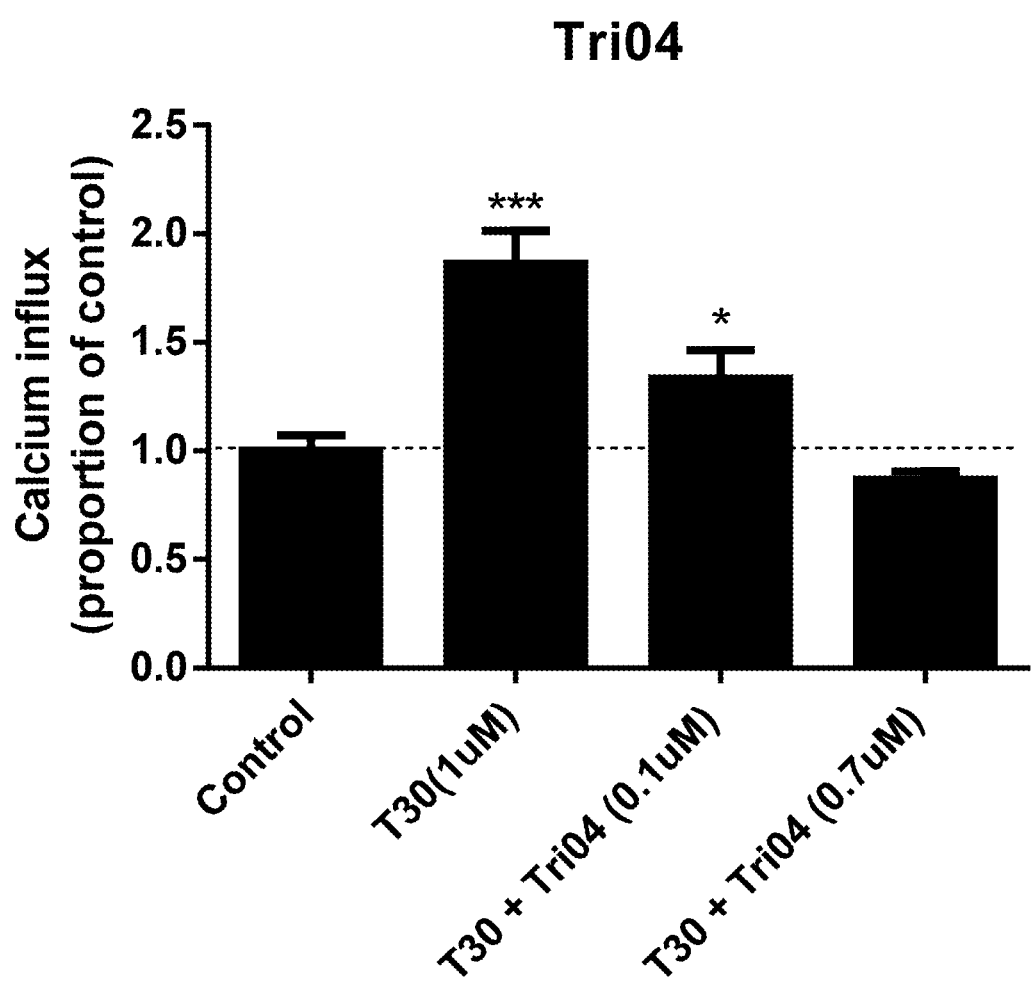
Figure 20:
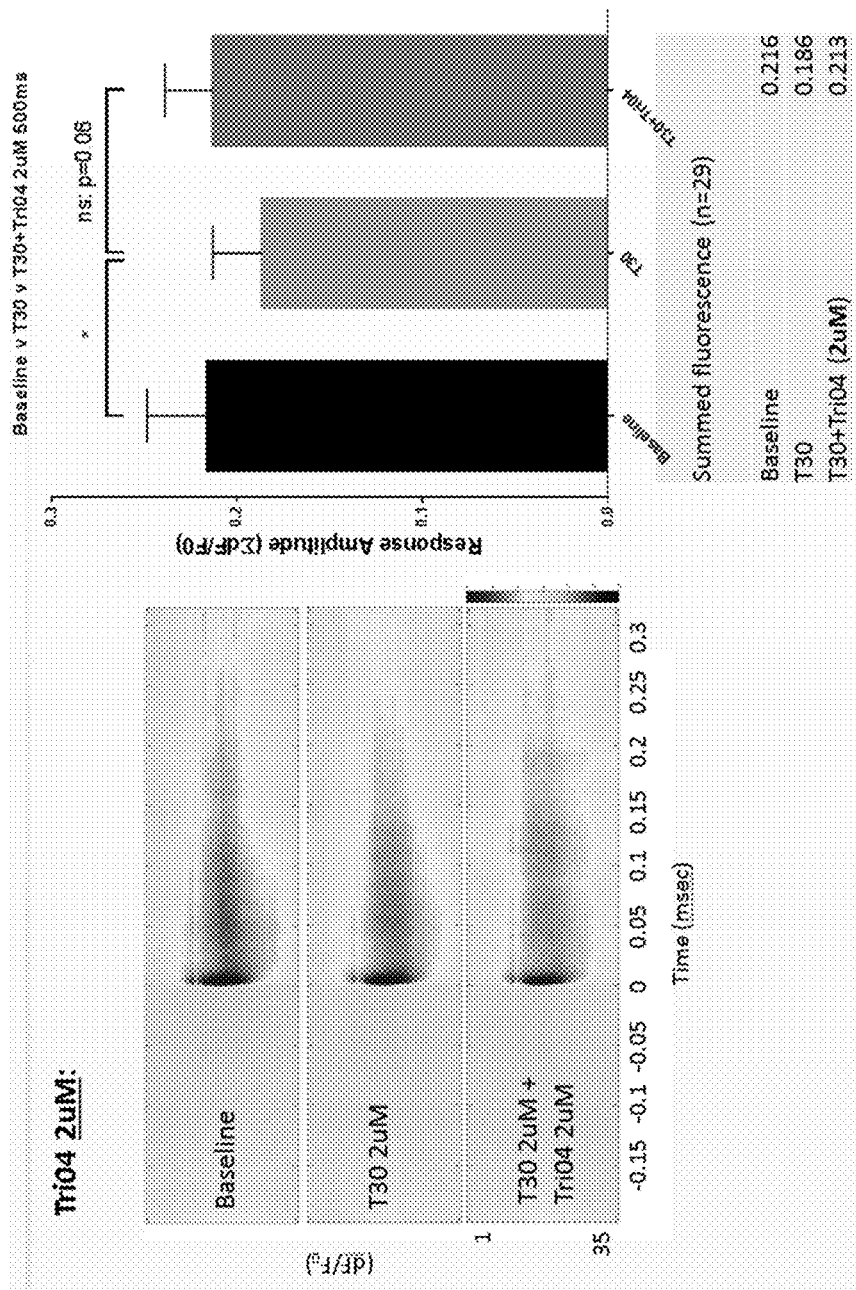
Figure 21:
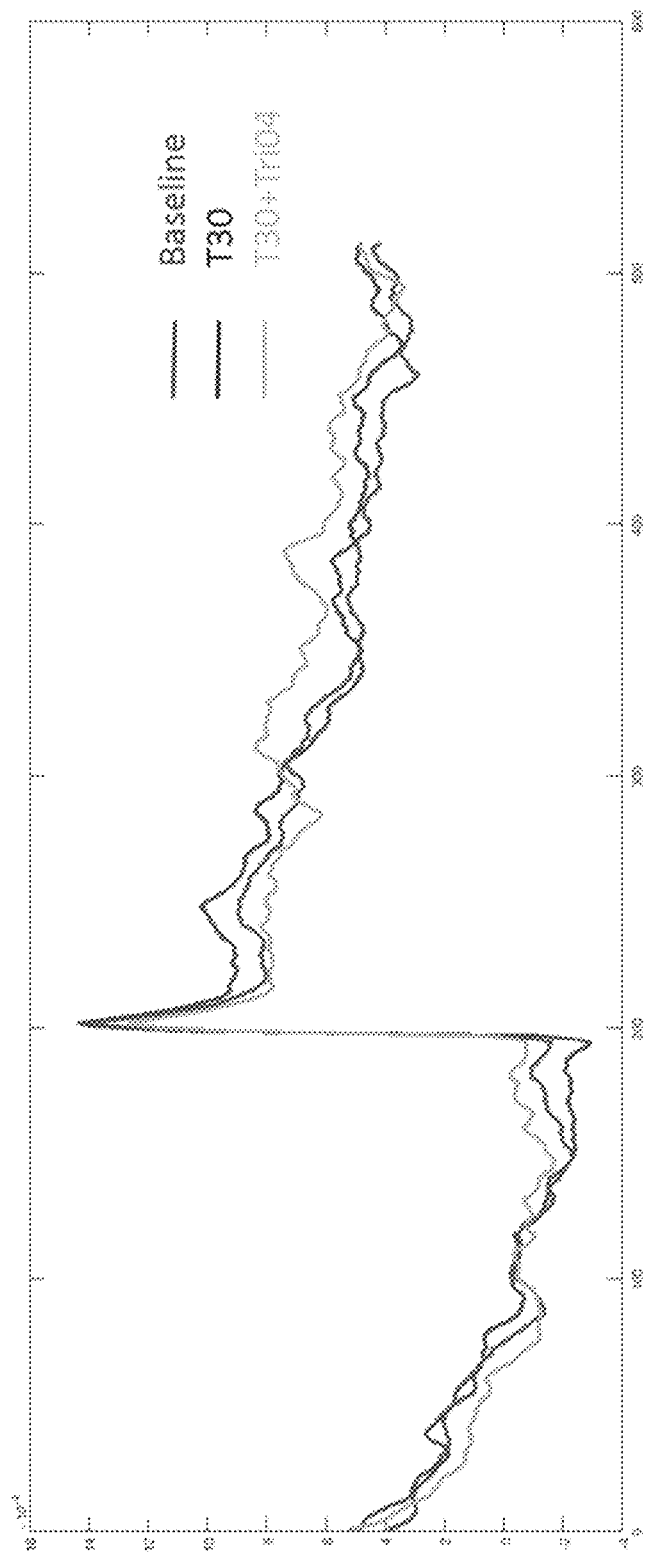
Figure 22:
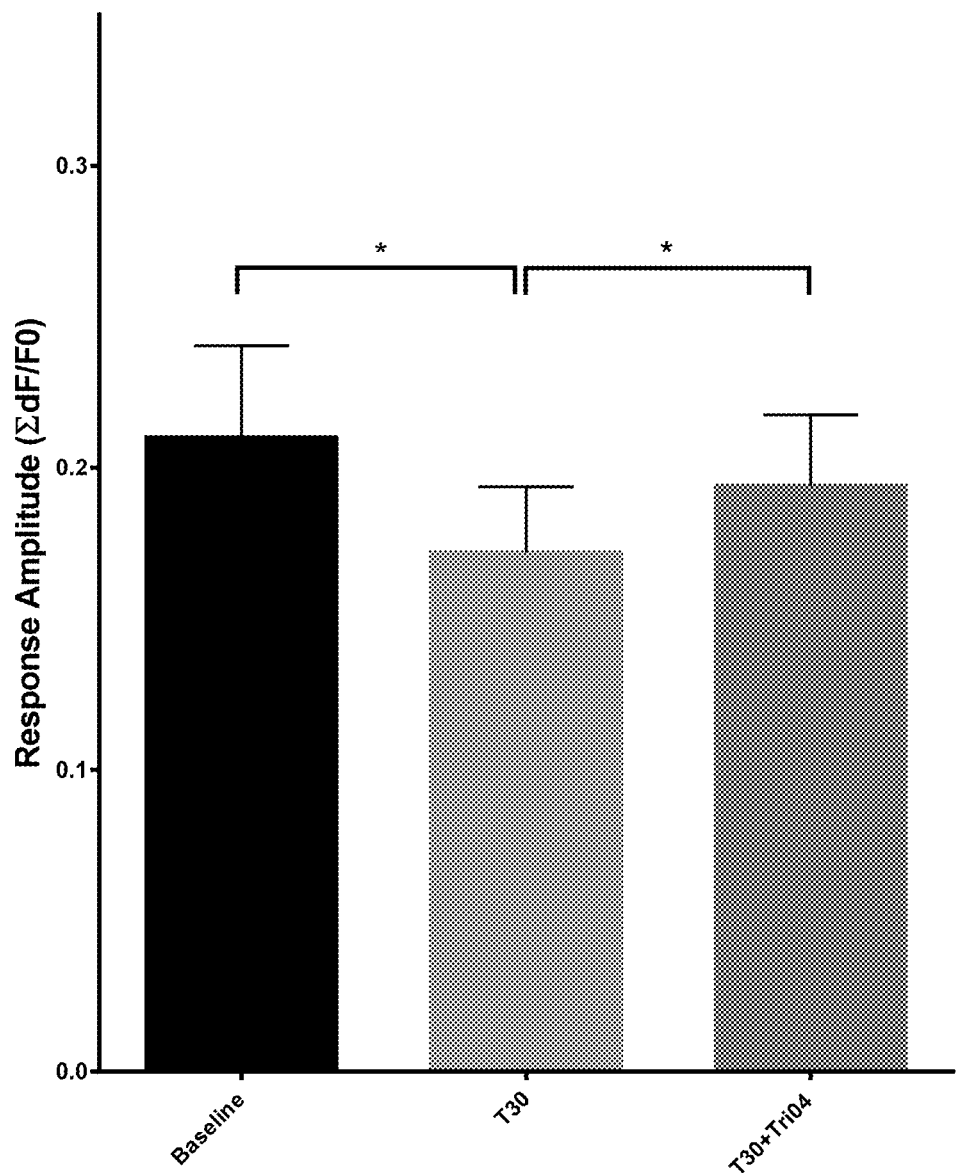
Figure 23:
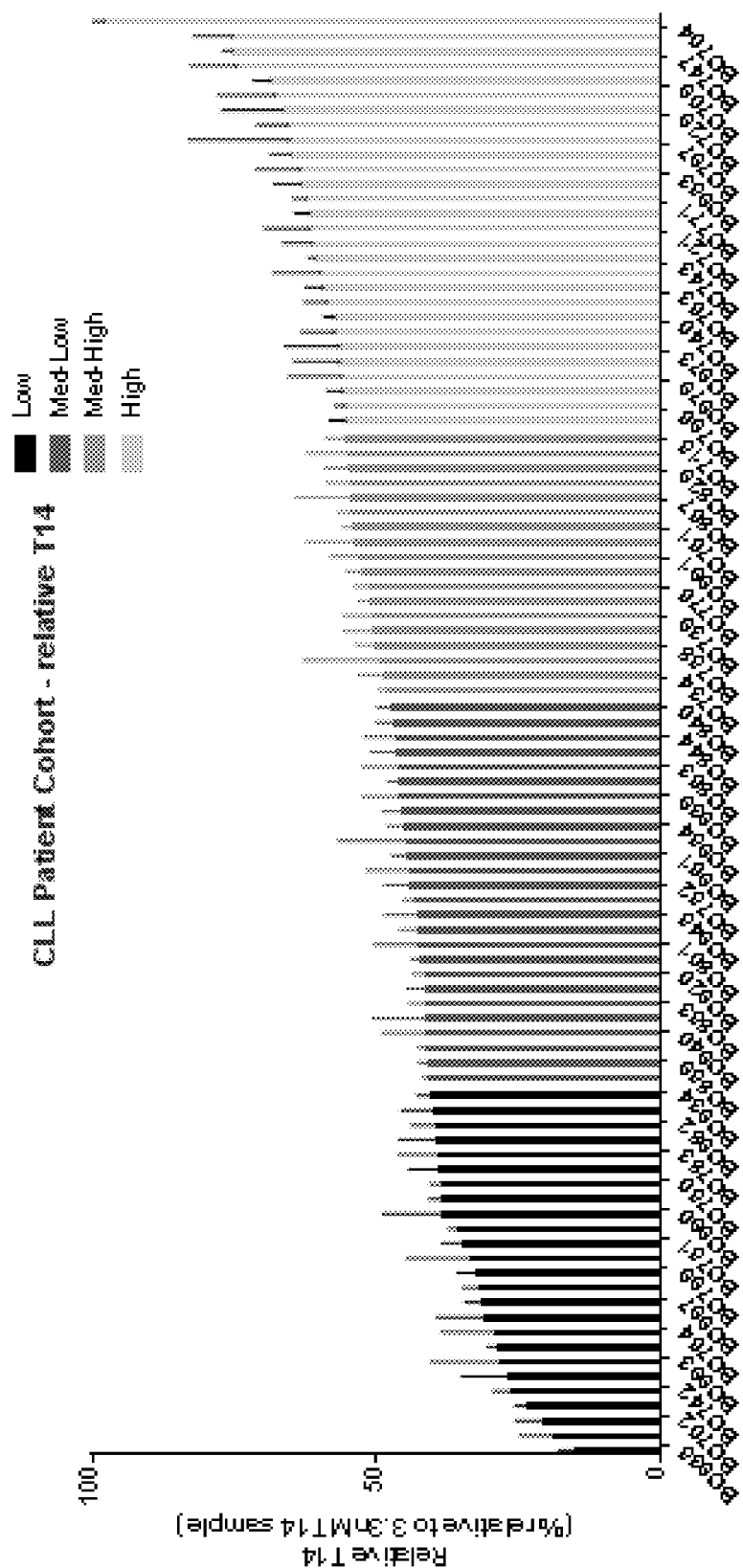
Figure 25:
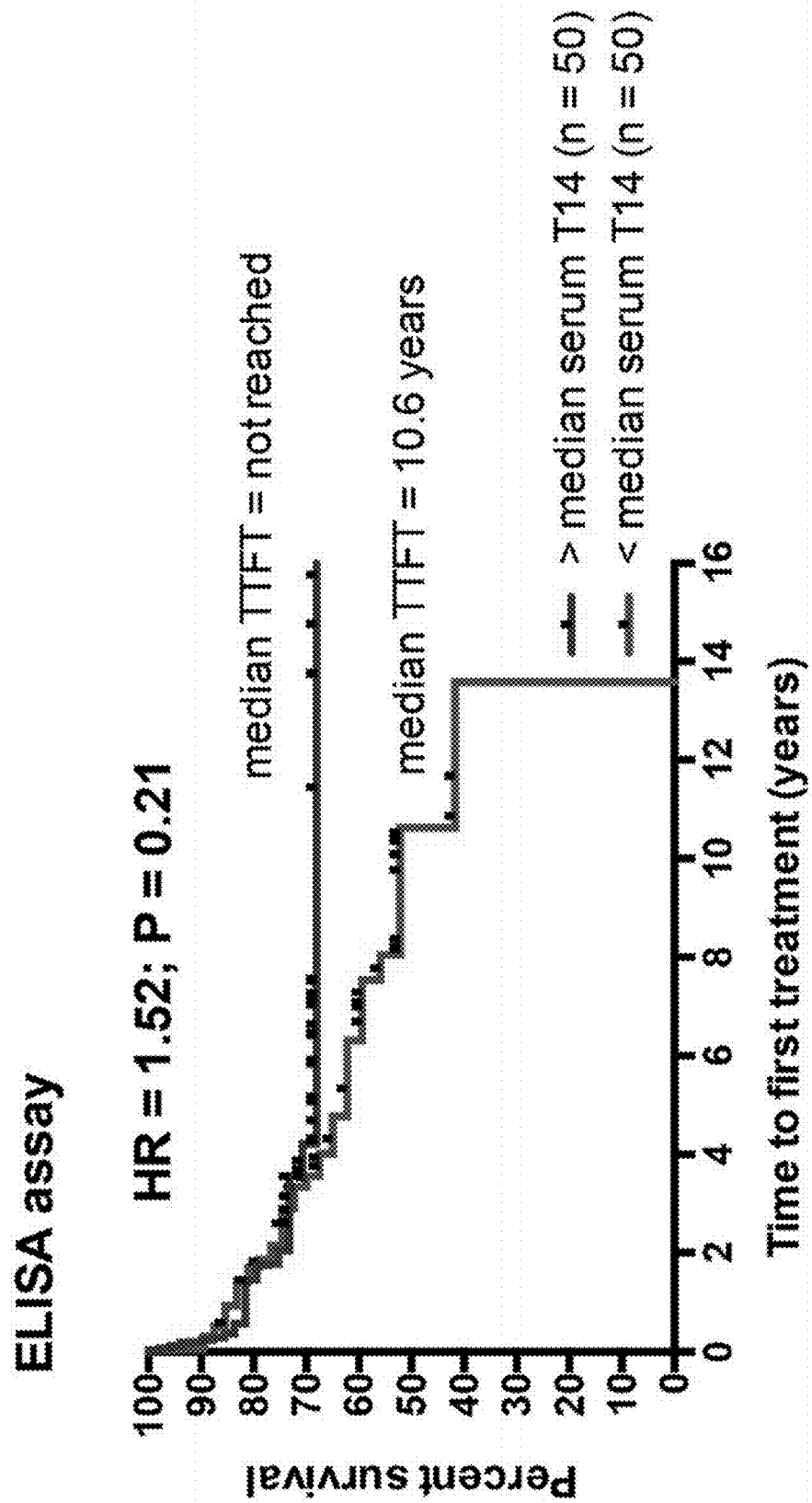
Figure 26:
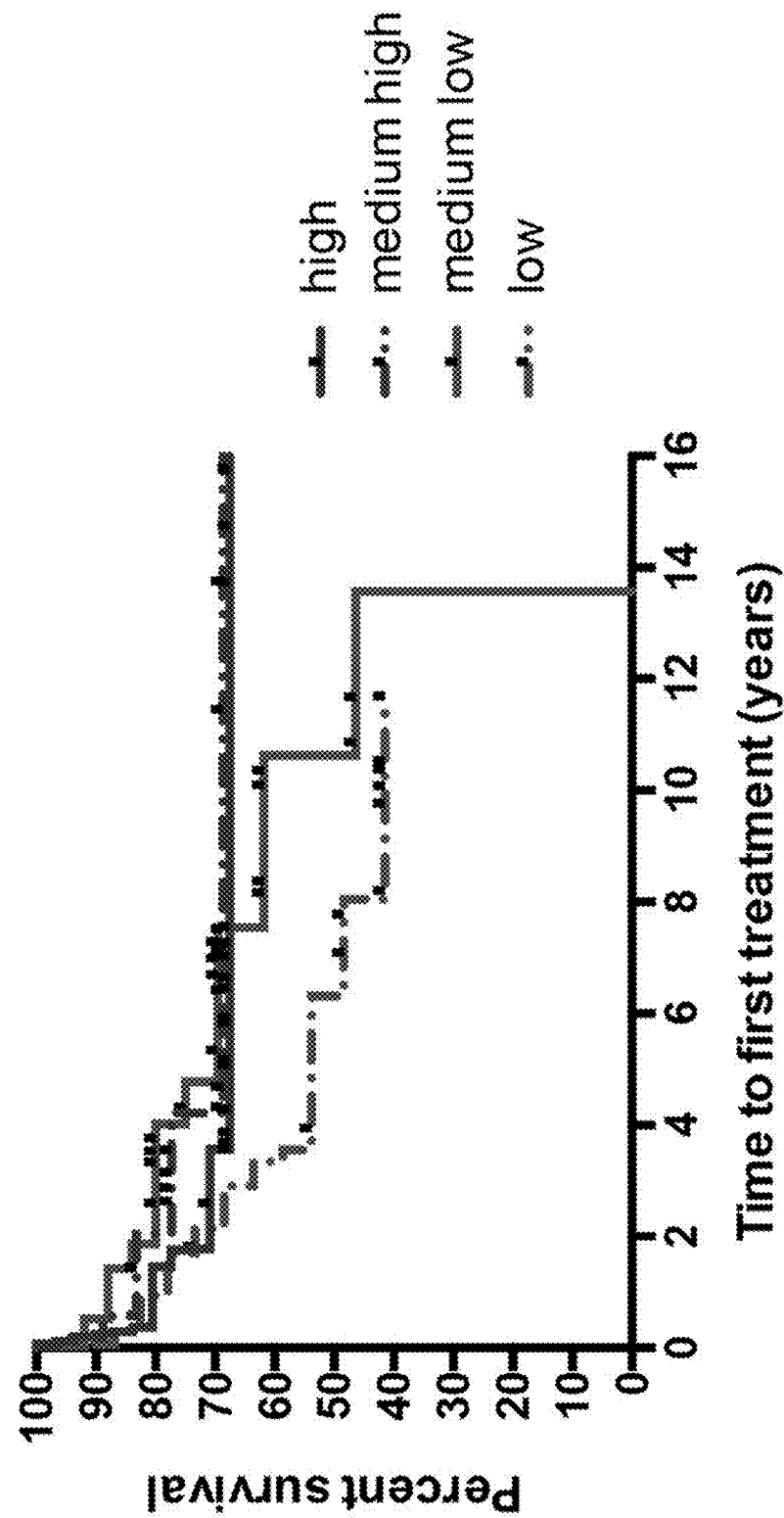

FIG. 9 shows Western Blot data showing similar mobility between CD44, T14 and AChE in the cell membrane and cytosol fractions of six cancer cell lines and one cancer-derived cell line. Alpha 7 receptor displayed different mobility from CD44, T14 and AChE. The order of lanes from left to right is: JJN3, MDA-MB231, MCF-7, KG1a, MEC-1, H929, and PC12. MDA-MB-231, KG1a, and MEC-1 cells are highly migratory cancer cell lines, whereas H929, JJN3, MCF-7 and PC12 are less migratory cancer cell lines;

FIG. 10 shows relative expressions of CD44, T14, AChE and Alpha 7 receptor to total protein (TP) level. Strongly metastatic cancers have more proteins at the membrane compared to the cytosol, whereas this relationship is variable for weakly metastatic cancers;

FIG. 11 shows significant positive correlations between CD44, T14 and AChE, strongly suggesting that T14 and AChE are good predictors of the degree of cancer metastasis;

FIG. 12 shows cell culture data (i.e. acetylcholinesterase activity) for peptidomimetic compound 1 (i.e. Tri02);

FIG. 13 shows cell culture data (i.e. calcium ion influx) for peptidomimetic compound 1 (i.e. Tri02);

FIG. 14 shows the results of voltage-sensitive dye imaging (VSDI) on brain slices for control cyclic peptide NBP-14;

FIG. 15 shows the results of voltage-sensitive dye imaging (VSDI) on brain slices for peptidomimetic compound 1 (i.e. Tri02);

FIG. 16 shows correlation analysis of changes induced by addition of peptides against respective baseline response amplitude using voltage-sensitive dye imaging (VSDI) on brain slices. Changes in response amplitude induced by T30 were found to be negatively correlated with the amplitude of their respective baselines (A). Therefore, subsequent correlation analyses were carried out for each experiment in which exogenous peptides were perfused: B) T15, C) NBP14, D) Tri02, E) T30 in the presence of NBP14 and F) T30 in the presence of Tri02. Units on y-axis=$\Delta F/Fo$; x-axis=$\Sigma \delta F/Fo$;

FIG. 17 shows quantification of effects mediated by the addition of Tri02 and T30;

FIG. 18 shows a graph comparing the co-application of T30 and NBP14 against that of Tri02 and T30 at blocking the effects of T30 on activity within the basal forebrain. NBP14 co-application was able to totally block the T30-induced effects, whereas T30 w/Tri02 caused a similar but muted modulatory response;

FIG. 19 shows PC12 cell culture data (i.e. calcium ion influx) for peptidomimetic compound 2 (i.e. Tri04);

FIG. 20 shows (A) space-time maps of basal forebrain activity changes induced by addition of peptides (T30 and Tri04) against the baseline response amplitude using voltage-sensitive dye imaging (VSDI) on brain slices. In (B) is shown a graph comparing basal forebrain evoked activity for recordings with T30 and Tri04 (2 uM) with that of T30 alone in the basal forebrain;

FIG. 21 shows the fluorescence fractional change (response time-series, n=29) for recordings made in the presence of T30 alone or after co-application of T30 and its blocker Tri04 in comparison to the baseline condition;

FIG. 22 shows a bar graph of basal forebrain activity using the blocker Tri04 at 4 µM concentration. Tri04 co-application was able to totally block the T30-induced effects in the rat basal forebrain;

FIG. 23 shows a bar graph of the range of levels of T14 as measured by ELISA relative to a known concentration of exogenous T14. Patients are rank ordered by relative T14 concentrations in the examined CLL patient cohort;

FIG. 24 shows a table of values of T14 as measured by ELISA relative to a known concentration of exogenous T14 in the examined CLL patient cohort and a statistical grouping;

FIG. 25 shows the Kaplan Meier estimate conducted on 100 CLL serum samples separated into the dark grey group (top curve) above the median and the light grey group (bottom curve) below the median. Hazard ratio, P value and the predicted median TTFT are indicated above;

FIG. 26 shows the Kaplan Meier estimate conducted on 100 CLL serum samples separated into four groups non different groups. Hazard ratio, P value and the predicted median TTFT are indicated above;

FIG. 27 shows a table of values of T14 from the examined CLL patient cohort and a statistical grouping;

FIG. 28 shows Kaplan Meier estimate conducted on 100 CLL serum samples, separated into the dark grey group (top curve) above the median and the light grey group (bottom curve) below the median. Hazard ratio, P value and the predicted median TTFT are indicated above; and FIG. 29 shows the results of a cell proliferation assay. Both T14 and T30 exhibit equal toxic effects at high concentrations (10 µM), the trophic effect at low concentrations on astroglia is greater with T30 (120±4% at 1 pM and 135±9% at 10 pM) than with T14 (96±5% at 1 pM and 121±8% at 10 pM).

EXAMPLES

Materials and Methods

Synthesis of Polyclonal Antibody

The antibody was synthesised on order by Genosphere Biotechnologies (Paris, France). Two New Zealand rabbits were used with four immunizations with KLH-peptide ("Pep4":T14-hapten CAEFHRWSSYMVHWK—SEQ ID No. 7) as immunogen over 70 days. The C was included to link the T14 peptide to the KLH acting as immunogen. The animals were bled four times and the bleeds were pooled. The antiserum was then passed through a gravity column with covalently bound peptide-support, following washing, the antibodies were eluted in acidic buffer and the solution neutralized. Further dialysis against PBS buffer and lyophilisation completed the process.

Optimisation of the T14 Antibody Conditions

The manufacturer's report on the antibody was used to perform the experiments of ELISA at the optimum conditions. In the report, the manufacturer specifies the optical density related to the concentration of antibody (see table below) and the ELISA protocol used for this procedure (see protocol below).

Protocol from the Manufacturer:

Antigens were coated on EIA strips at ioug per well. Wells were washed with 200 ul PBS buffer.

| Manufacturer ELISA Results: Absorbance 405 nm | | | | |
|---|---|---|---|---|
| Antibody | Rabbit No. 1 | | Rabbit No. 2 | |
| Dilution | Pre-immune | Purified | Pre-immune | Purified |
| 1:1 000 | 0.120 | 1.64 | 0.143 | 1.66 |
| 1:10 000 | 0.045 | 0.77 | 0.036 | 0.74 |
| 1:100 000 | 0.016 | 0.19 | 0.017 | 0.19 |

Antisera was diluted in series, added in separate wells, and incubated for 2 hours. Unbound antibodies were washed and anti-rabbit IgG-HRP conjugate was added. Plates were washed and colour development run for 15 minutes with TMB substrate. Absorbance was read at 405 nm (2.00 AUFS). Colour intensity was directly proportional to the amount of antibodies. Antibody was positive if absorbance was >2 folds over that of pre-immune serum. Background absorbance for pre-immune serum could reach 0.1 to 0.3.

Conclusion

For all the experiments described herein, the 1:1000 was the chosen dilution of antibody.

Western Blotting

Cell Fractionation

Whole cell pellets from the cancer cell lines (JJN3, MDA-MB231, MCF-7, KG1a, MEC-1, H929, PC12) were resuspended in the 300 µl of subcellular fractionation buffer (Hepes-NaOH 10 mM, $MgCl_2$ 1.5 mM, KCl 10 mM, EDTA 1 mM, DTT 1 mM, 1× Proteinase Inhibitor Cocktail, Nonidet P-40 0.05%) and left on ice for 10 min. Following that, the mixtures were homogenised using a polytron to ensure cell lysis. Then, the mixtures were centrifuged at 500 g for 5 min. The resulting supernatant contained the cytosol portion and was retained. The resulting pellet contained the membrane fractions, which was then resuspended in a further 300 µl of subcellular fractionation buffer and retained.

Cell Lysate Preparation

Whole cell pellets from seven cancer cell lines (MEC-1, CLL, KG1a, JJN3, H929, MCF-7 and MDA-MB) and normal B lymphocyte were kindly donated from Prof Chris Pepper (School of Bioscience, Cardiff University). Whole cell pellets were solubilised in 1×Lysis Buffer (20 mM Tris Base, 137 mM NaCl, 1% TWEEN-20 detergent, 2 mM EDTA) containing protease inhibitor cocktails (Phosphatase 1:1, PMSF 1:1, aprotinin 1:1) with a 17% v/v ratio. Subsequently, the mixture was triturated using a Polytron for 10 seconds and shaken at 4° C. for 2 hours. Then, the samples were centrifuged at 13,000 g for 30 minutes at 4° C. and the supernatants were taken and stored at −80° C.

Measuring Protein Sample Concentration

Protein concentrations from the above samples were measured using the Pierce™ 660 nm Protein Assay (Thermo Scientific). In short, a serial dilution (0 to 2 mg/ml) was made from a 10 mg/ml stock of bovine serum albumin (BSA). Three replicates of each BSA concentration were prepared by transferring 10 µl of the protein into a clear 96 well plate (Greiner). Then, samples were diluted with three concentrations (1:1, 1:2, 1:10) and three replicates of each concentration were placed into the same 96 well plate with each replicate containing 10 µl of sample. Subsequently, 150 µl of Pearce Reagent was added to the standards and all samples and the mixture was left to incubate for 5 min with gentle shaking. Finally, the plate was read on a spectrophotometer (Molecular Devices) at 660 nm. The protein concentrations of the samples were determined using the slope and y-intercept from the BSA standard curve, both calculated via Microsoft Excel.

Polyacrylamide Gel Electrophoresis of Protein Samples

Polyacrylamide gels (mini-PROTEAN® TGX stain free™ gels, BIO-RAD) were placed into the electrophoresis tank (BIO-RAD, mini-PROTEAN tetra system) and Running buffer (25 mM TRIS-base, pH 8.6, 192 mM glycine, 0.1% SDS) was added the gel and tank reservoirs (BioRad). Protein samples were prepared by mixing with distilled water and 4× Laemmli sample buffer (final concentrations: 69.5 mM TRIS-Ha pH 6.8, 1.1% LDS, 11.1% (w/v) glycerol, 0.005% bromophenol blue, BIO-RAD) and 2.5% mercaptoethanol (BIO-RAD). The mixtures were heated at 95° C. for 5 min before cooling on ice. Samples and the positive control were loaded into the gels and were electrophoresed alongside with a molecular weight marker (Precision Plus Protein™ Dual Xtra Standards, BIO-RAD) at 35 mV for 90 min. Ice block was placed inside the running tank to prevent any overheating.

Transfer of Protein Samples onto PVDF Membrane

Stacking gels were trimmed off and the separating gels were transferred onto PVDF Transfer Membrane (Thermo Scientific) in a Mini Transblot Cell (BIO-RAD). Briefly, the PVDF Transfer Membrane was activated by soaking with methanol for 1 min followed by soaking with distilled water for 2 min. All layers were subsequently saturated with transfer buffer (20 mM TRIS-base pH 8.6, 154 mM glycine, 0.8% w/v SDS and 20% methanol). The transfer sandwich, in the order of bottom to top, consists of transfer sponge, blotting paper, the gel, PVDF Transfer Membrane, blotting paper, transfer sponge were placed into a transfer cassette, which was inserted into the Mini Transblot Cell filled with Transfer Buffer. Finally, electrophoretic transfer took place for 90 min at 200 mA. Ice block was placed inside the transfer tank to prevent any overheating.

Staining of PVDF Membrane

BLOT-Faststain™ (G-Biosciences, USA) was used to stain for total protein, acting as the loading control. Immediately after electrophoretic transfer, the PVDF transfer membrane was stained with the diluted BLOT-Faststain™ fixer solution (10 fold) for 2 min with gentle shaking. The membrane was then incubated with the diluted BLOT-Faststain™ developer solution (4 fold) for 1 min with gentle shaking. Subsequently, the membrane was stored at 4° C. in the dark in the developer solution for 30 min to allow protein bands to reach maximum intensity. Finally, the membrane was washed with cold water to eliminate background staining and imaged using the G box (Syngene). The membrane can then be destained using warm deionised water (40-45° C.) and ready is for the blocking stage.

Detection of Protein Bands

The PVDF transfer membrane was blocked in TBS (TRIS-buffered saline, 20 mM TRIS-base pH 7.5, 0.5 mM NaCl) containing 5% skimmed milk powder for 1 h, then washed twice for 7 min each in TTBS (TBS supplemented with 0.05% v/v TWEEN-20 detergent). The membrane was incubated overnight at 4° C. with a primary antibody diluted in TTBS containing 1% skimmed milk powder. On the following day, the primary antibody was removed. The membrane was washed three times for 5 min each in TTBS, then incubated for 1 h at room temperature with the secondary antibody. The secondary antibody of choice depends on the type of primary antibody used. It can either be goat anti mouse secondary antibody conjugated to HRP (a9309, Sigma, diluted in TTBS containing 1% skimmed milk powder (working concentration: 1:1000) or goat anti rabbit secondary antibody conjugated to HRP (ab6721, abcam) diluted in TTBS containing 1% skimmed milk powder (working concentration: 1:5000). After secondary antibody incubation, membranes were washed three times for 5 min in TTBS before a final 10 min wash in TBS. Protein bands were detected using the G box (Syngene).

TABLE 1

Primary antibodies used for Western blotting detection.

| Antibody | Species Raised in | Company | Catalogue Number | Working conc. |
| --- | --- | --- | --- | --- |
| Anti-T14 | Rabbit | Neuro-Bio | N/A | 1:1000 |
| Anti-Nicotinic Acetylcholine Receptor alpha 7 | Rabbit | Abcam | Ab10096 | 1:1000 |
| Anti-AChE | Rabbit | Abnova | PAB 5222 | 1:1000 |
| Anti-CD44 | Rabbit | Sigma | HPA005785 | 1:1000 |

Protein Band Imaging and Data Analysis

The PVDF membrane was placed in the G box (Syngene). The focus and zoom settings were adjusted to ensure that the membrane was at its largest at the centre of the screen. Luminol and Peroxide solutions from Clarity™ Western ECL substrate (BIO-Rad) were mixed the equal parts and applied to the membrane. Images were taken in the dark at 1 min time intervals for 5 min to obtain the optimal signal for the protein bands. Following that, the membrane was exposed in white light using an automatic setting in order to obtain an image for the molecular ladder. The blot images were then analysed using image J. Box of equal sizes were placed around protein bands in each lane, allowing measurement of protein band intensities. The background was then subtracted from the band intensities and the results were analysed in Microsoft Excel and the Graphpad software.

Antibody Stripping for Reprobing

The protein signal from the PVDF transfer membrane can be stripped and reprobed for a different protein. Briefly, the membrane was washed with mild stripping buffer (200 mM Glycine, 3.5 mM SDS, 1% v/v TWEEN-20 detergent, pH 2.2) twice for 10 min each. Subsequently, the membrane was washed with PBS twice for 10 min each and then washed with TTBS twice for 5 min each. Clarity™ Western ECL substrate (BIO-Rad) was added to the membrane and imaged using the G Box (Syngene) in order to check for residual protein signals. If residual signal was too strong, then the whole stripping process was repeated. Then, the membrane was ready for subsequent blocking stage and primary antibody probing (see above).

ELISA for T14 Peptide Antibody

The standard curves and the samples were run in triplicate. The Cell Culture Media and Cell Lysate samples were diluted 1:10 in PBS Buffer. The standard curve for determination of T14 peptide in brain tissue samples were diluted in PBS buffer. The standard curve ranged from 8 to 100 nM of T14, and the blank was PBS buffer alone. Briefly, 96-well immunoplates (NUNC) were coated with 100 µl/well of sample or standard T14, covered with parafilm and incubated overnight at 4° C. The following day the sample was removed by flicking the plate over a sink with running water, and 200 µl of the blocking solution containing 2% bovine serum albumin (BSA) in Tris-buffered saline and Tween 20 (TBS-T) was added and incubated for 4 h at room temperature. Blocking solution was then removed and 100 µl of antibody, diluted in blocking solution to 1 µg/ml, was added and incubated overnight at 4° C. The primary antibody was removed the next day and wells were washed 3 times with 200 µl of TBS-T. After 100 µl of secondary enzyme-conjugated antibody diluted in blocking solution to 0.1 µg/ml was added and incubated for 2 h at room temperature; the plate was covered with parafilm during all incubations. After 2 h, the plate was washed 4 times with TBS-T. The addition of 3,3,5,5-tetramethylbenzidine started the colour reaction. The reaction was stopped 20 min later with stopping solution containing 2 M $H_2SO_4$, and the absorbance was measured at 450 nm in a Vmax plate reader (Molecular Devices, Wokingham, UK).

Example 1

The inventors set out to detect the levels of the toxic T14 peptide (AEFHRWSSYMVHWK—SEQ ID No:3), nicotinic alpha-7 receptor and acetylcholinesterase (AChE) proteins using Western Blotting in cell lysate and cell culture media of seven cancer cell lines (MEC-1, KG1a, H929, MCF-7, MDA-MB 231, CLL, JJN3), and normal B lymphocytes acting as control. In addition, they detected the levels of the T14 peptide using ELISA.

Results from Western Blotting

Figure 1:
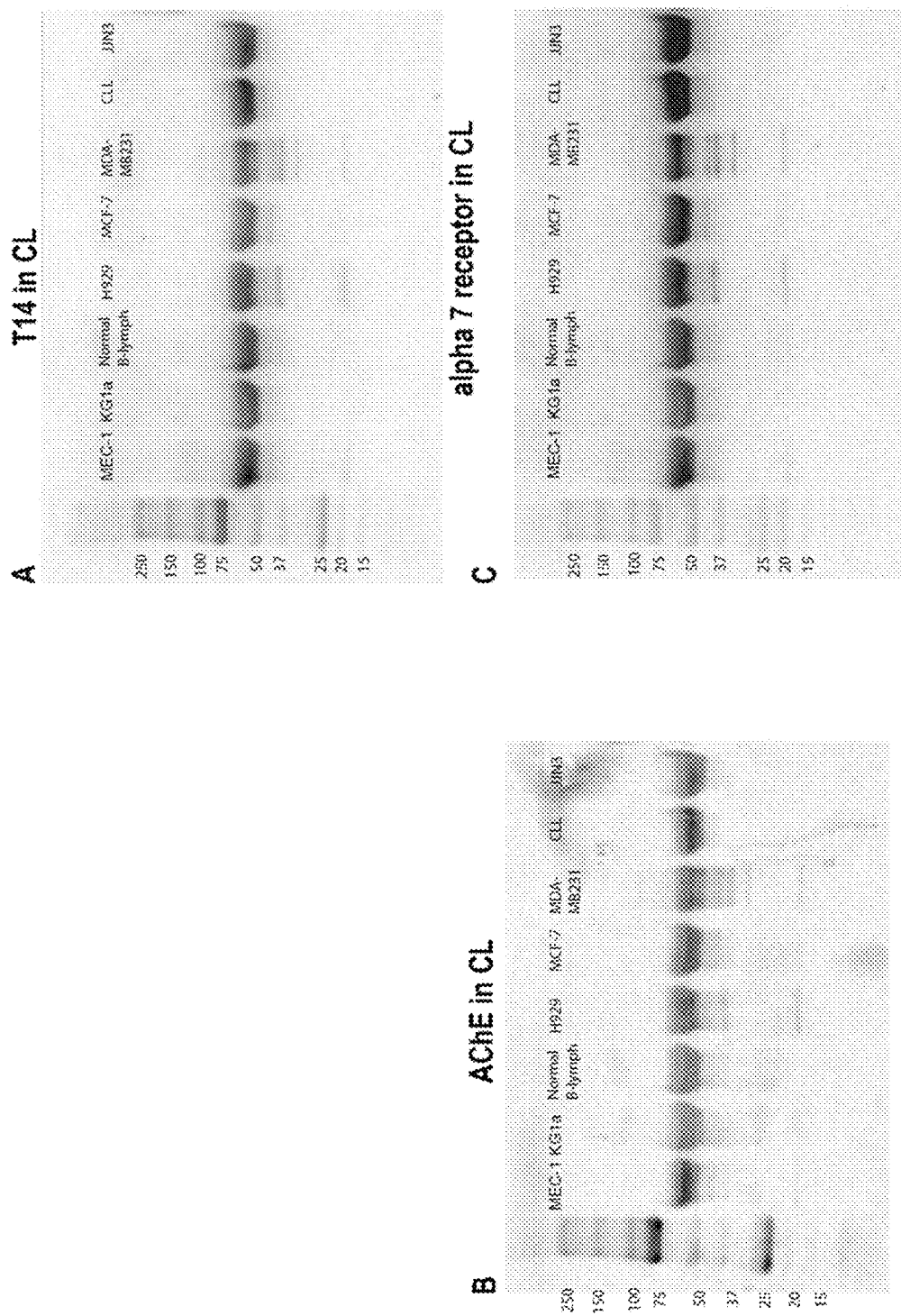

Western Blotting (WB) was carried out to detect the levels of T14, AChE and alpha 7 nicotinic acetylcholine receptor in cell lysate (CL) of seven different cancer cell lines, and normal B lymphocytes as control. Qualitative data showed that T14, AChE and alpha 7 receptor were all detected in the CL of all cell lines. Surprisingly, all three proteins have virtually identical mobility (see FIGS. 1A, B and C). The inventors do not consider this to be antibody cross-reactivity because the three proteins showed different mobility in the human brain homogenate (data not shown). Subsequently, T14, AChE and alpha 7 receptor levels were quantified and normalised against total protein levels (Colins et al 2015).

Figure 2:
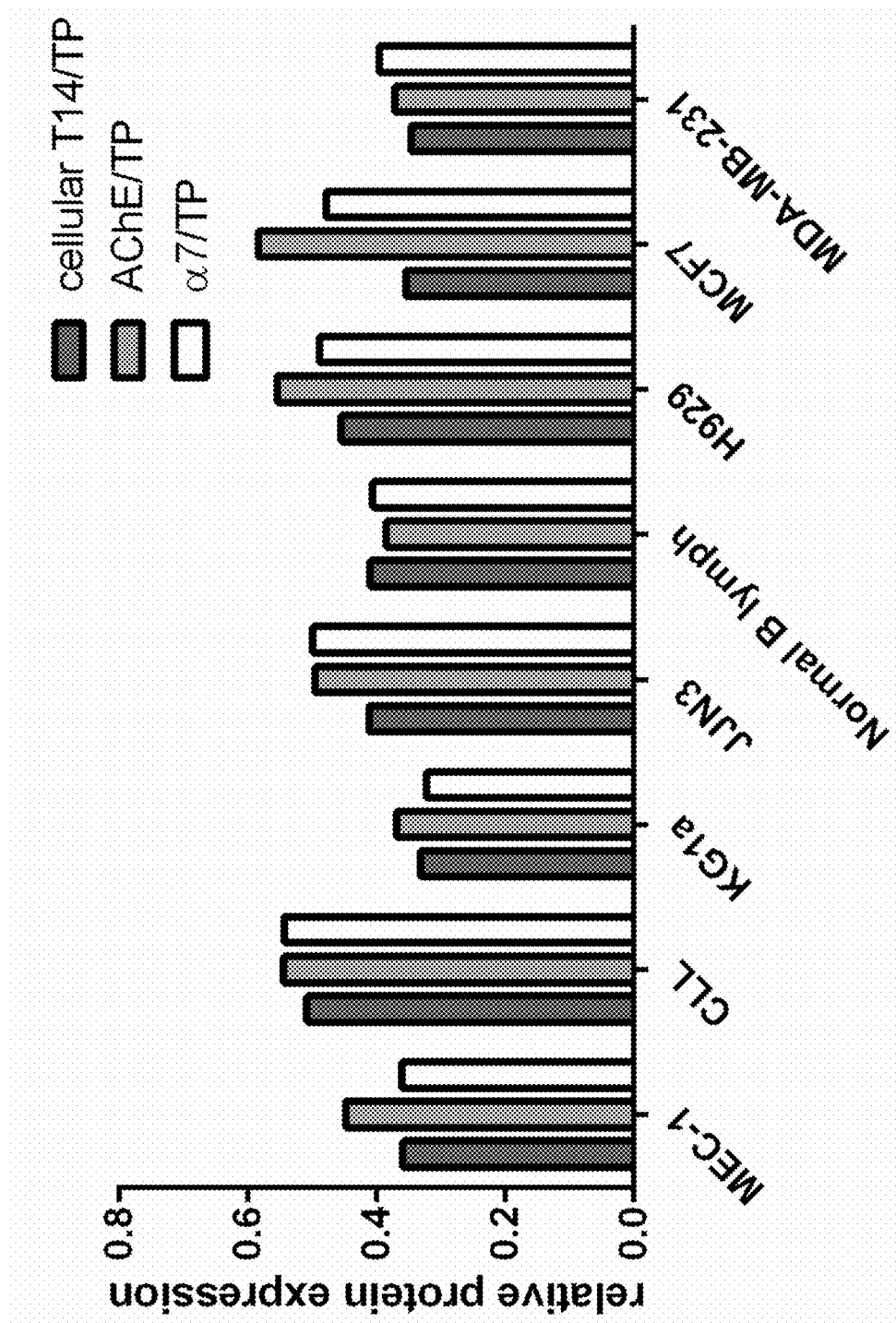

Quantitative data showed that the levels of T14, alpha 7 receptor and AChE within each cell line was similar, with the exception of the MCF-7 line having low cellular T14 levels (see FIG. 2). However, the levels of T14, alpha 7 receptor and AChE were variable between cell lines (see FIG. 2).

Figure 3:
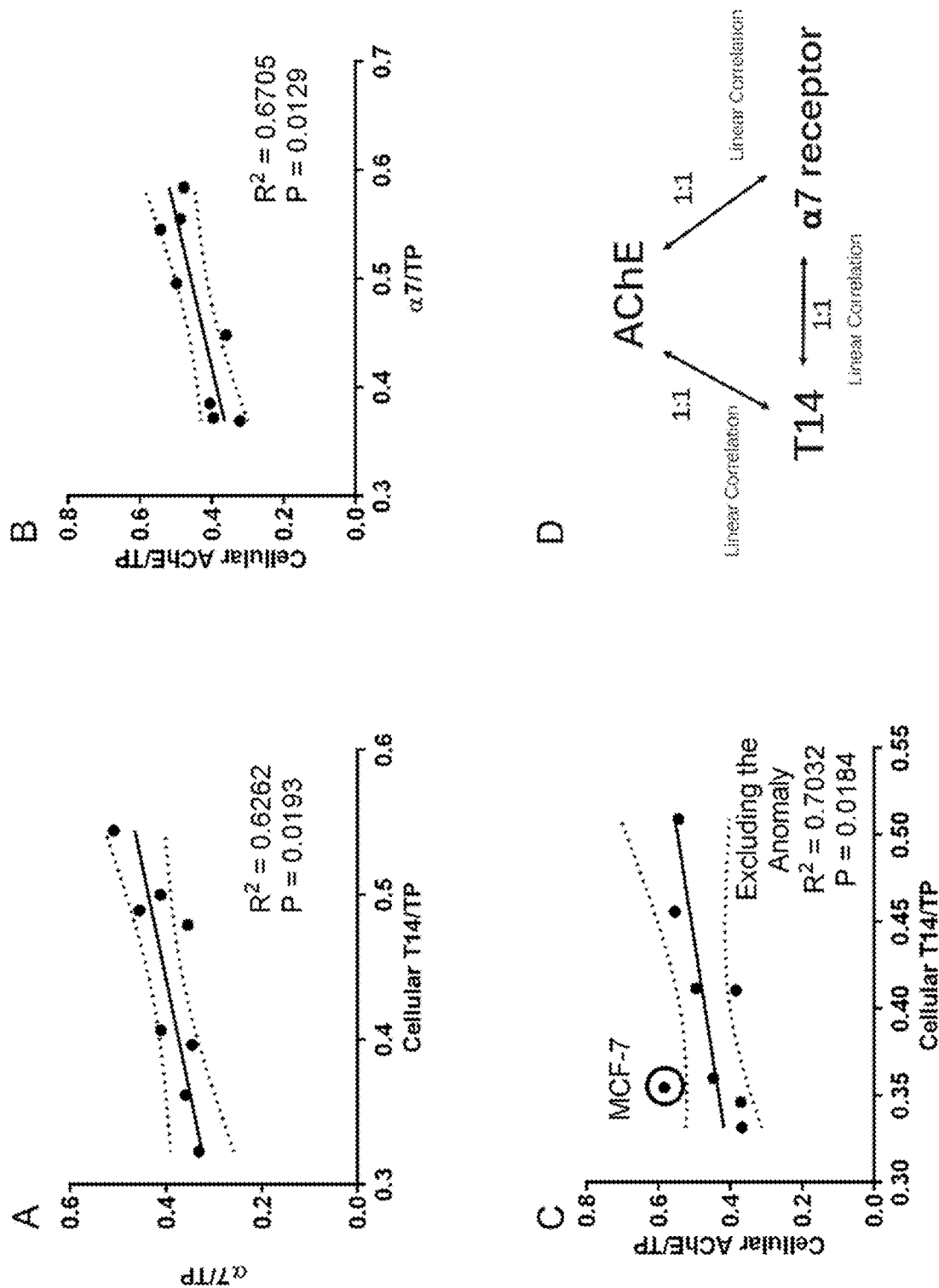

Interestingly, within the cell lysate, significant positive correlations were found between levels of T14 and the alpha 7 receptor (see FIG. 3A), alpha 7 receptor and AChE (see FIG. 3B), T14 and AChE levels (see FIG. 3C). These correlations and the identical mobility of protein bands suggest that T14, AChE and alpha 7 receptor exist as a protein complex within the cancer cells with a ratio of 1:1:1.

Figure 4:
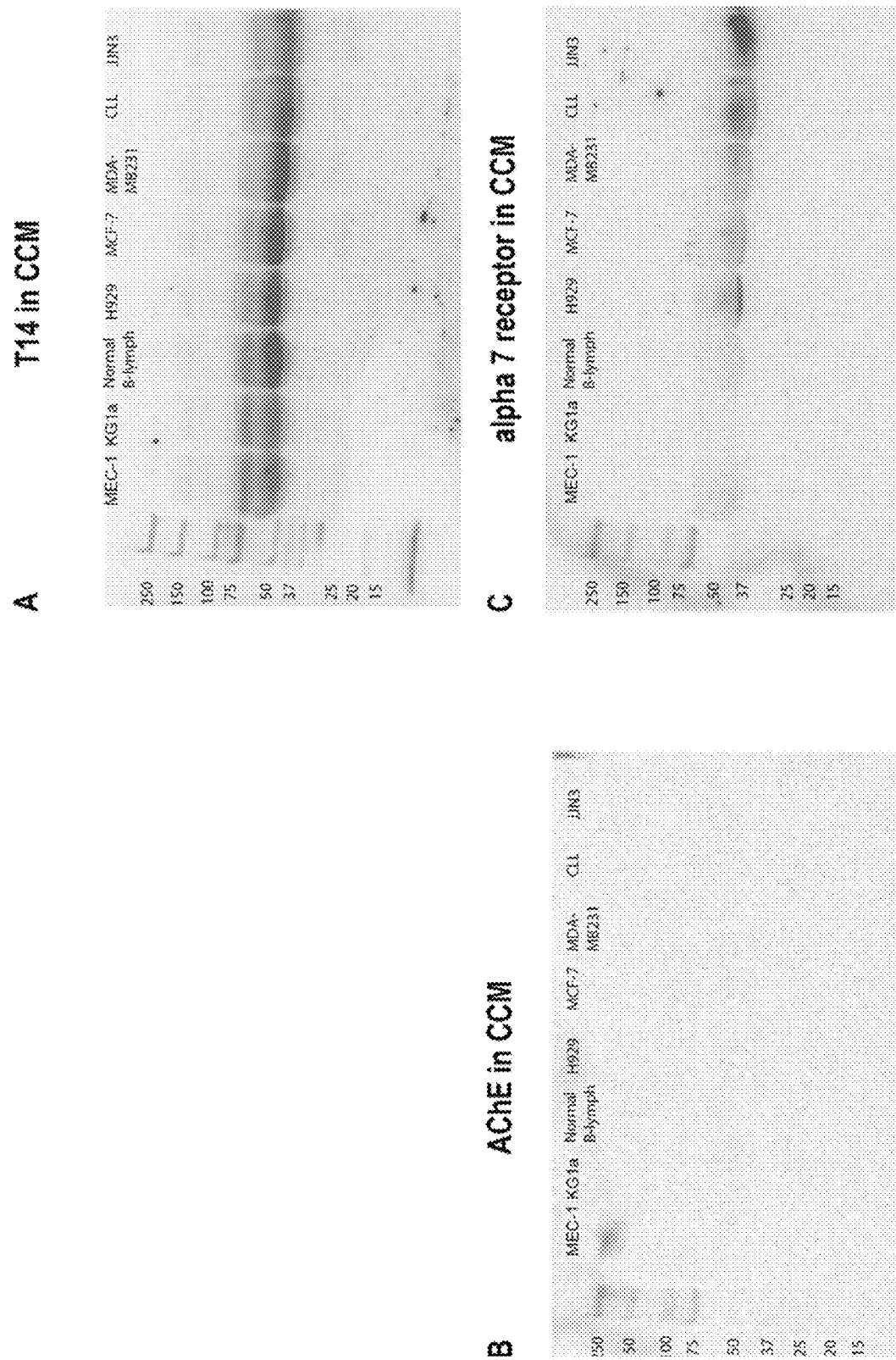

Subsequently, Western Blotting was carried out to detect the levels of T14 and possibly the alpha-7 receptor and AChE released into the cancer cell culture media (CCM) of the above cell lines. Qualitative data showed that there was only T14 released into the cell culture media (see FIG. 4) but AChE was not (see FIG. 4). There was a minute amount of alpha 7 receptor released into the cell culture media (see FIG. 4), suggesting that they could be from dead floating cancer cells.

Figure 5:
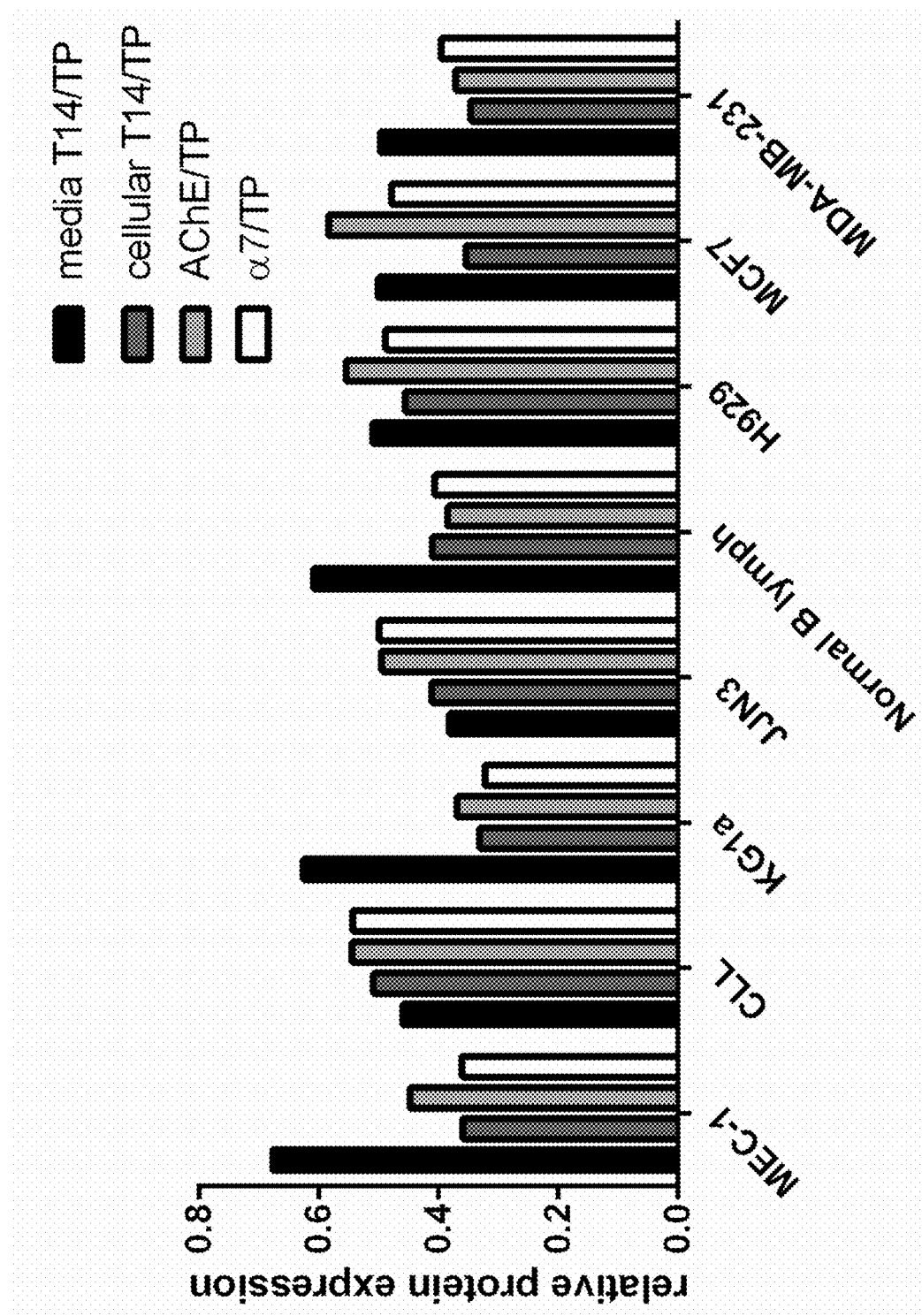

Quantitative data showed that T14 released into the cell culture media was greater than cellular T14, alpha 7 receptor and AChE in MEC-1, KG1a, Normal B lymphocyte and MDA-MB-231 cell lines (see FIG. 5). However, T14 released into the cell culture media was similar to T14, alpha 7 receptor and AChE levels in primary CLL, JJN3, H929 and MCF-7 cell lines (see FIG. 5).

Figure 6:
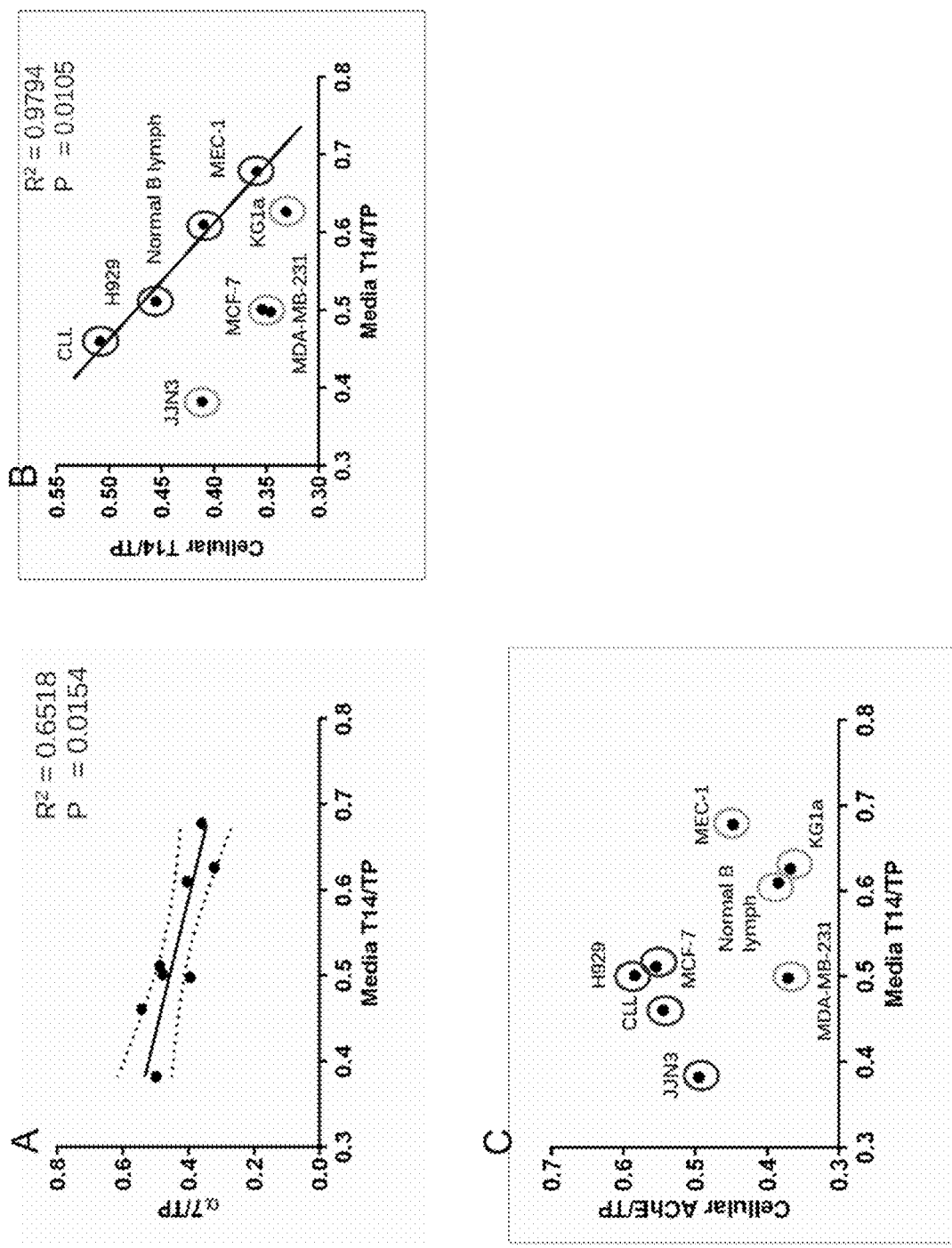

Subsequently, levels of T14 within the cell culture media was correlated with T14, AChE and alpha 7 receptor levels within the cell lysate. A significant inverse correlation was found between the released T14 levels in the cell culture media and the alpha 7 receptor levels in the cell lysate (see FIG. 6a). The inventors believe that this could be a general pathological mechanism since this effect also occurs in the Cerebral Cortex and Locus Coeruleus of Alzheimer's patients (data not shown). No apparent correlation was found between T14 within the cell culture media and T14 levels within the cell lysate, although there was a significant inverse correlation when only four cell lines were included in the analysis (see FIG. 6B, dark grey group). Moreover, no apparent correlation was found between T14 within the cell culture media and AChE levels within the cell lysate even when cell groups were analysed separately (see FIG. 6C).

ELISA Results

T14 Levels in Cell Lysate and Cell Culture Media

Figure 7:
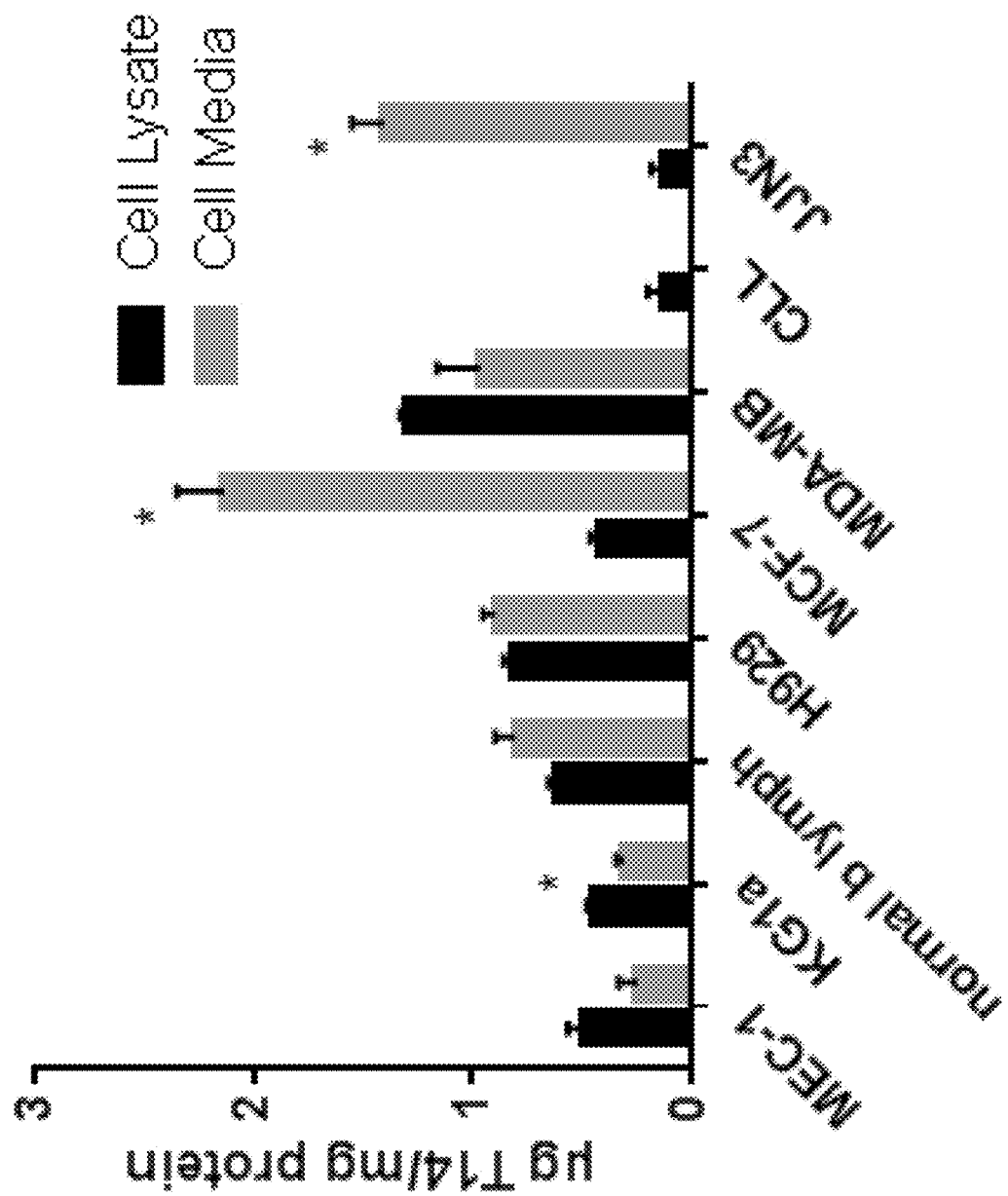
FIG. 7 is a graph showing that T14 levels vary significantly between cell lines and between cell media and cell lysate detected by ELISA.

The aim was to determine endogenous levels of T14 in cancer cells of varying metastatic propensity, kindly provided by Prof Chris Pepper of Cardiff University, in both the intracellular material recovered from lysed cells and levels of T14 released into the growth medium of the cells (CCM) using the ELISA Method. The method used combined results from a total protein (pierce assay) to provide a measure of μtg T14 for every mg of protein in the sample. The results show a high degree of variance in T14 levels between cell lines and between cell lysate and cell media within cell lines, as shown in FIG. 7.

T14 was highest in the cell lysate in the MDA-MB cell line but the same cell line showed lower levels of T14 in the cell media comparatively. Levels of T14 were shown to be highest in the MCF-7 cell line, however this cell line also had one of the lowest concentrations of T14 in the cell lysate, suggesting that although T14 is highly expressed in this cell line, there is approximately 5× more outside of the cells than within the cells. Only JJN3 and KG1a had significantly different levels of T14 when comparing intracellular and extracellular levels. In JJN3, the same profile is seen as in the MDA-MB cell line with extracellular levels of T14 significantly higher than intracellular levels. The KG1a cell line is the only cell line to demonstrate a significantly higher level of T14 in the cell lysate when compared with the media. T14 in the media of the CLL cell line was below the limit of detection for this assay.

Comparison of Cancer Cell Line ELISA T14 Data with WB Cancer Cell Line Data

Figure 8:
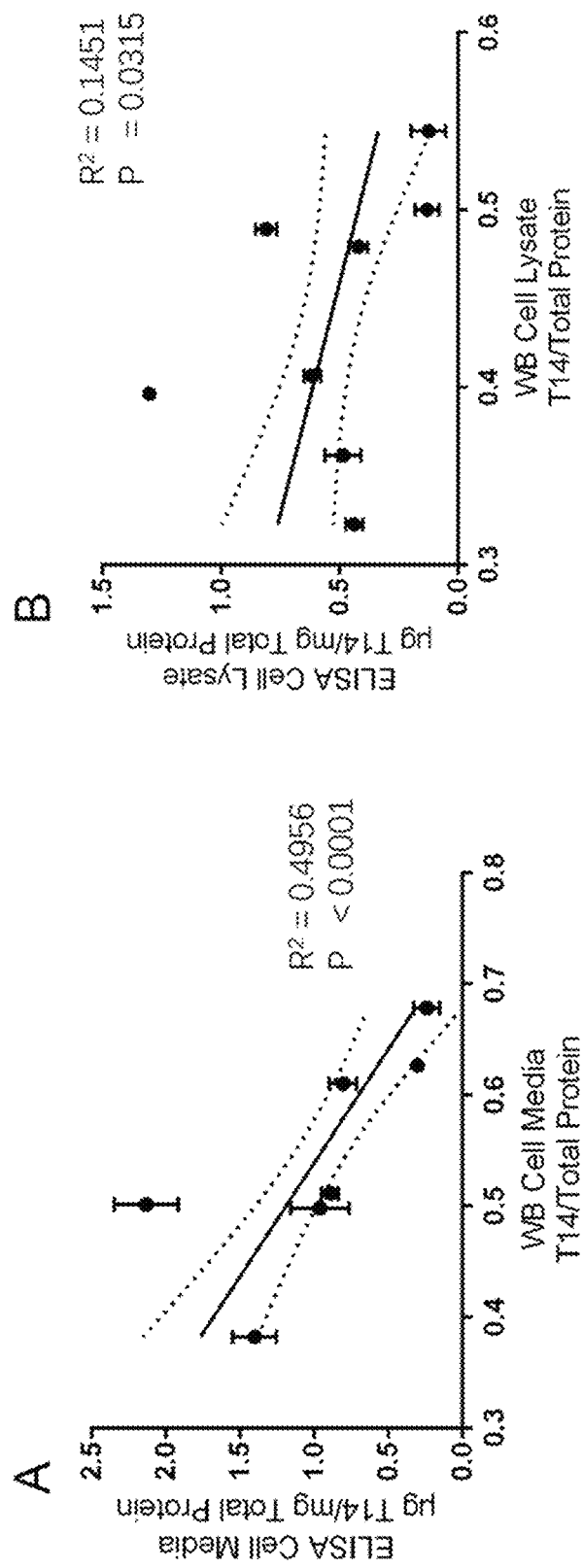
FIG. 8 are graphs demonstrating the significant inverse correlations between T14 levels in ELISA and Western Blot measurements for cell media and cell lysate in cancer cell lines.

Using the results taken from the ELISA and those collected from the Western Blots, the inventors compared μg of T14/mg protein and T14/total protein in both the cell lysate and in the cell media. A significant inverse correlation was seen between WB T14 and ELISA T14 levels measured in the cell media as well as in the cell lysate as can be seen in FIG. 8.

The cell media and cell lysate both demonstrate inverse correlations between levels of T14 as measured by WB and ELISA ($P<0.0001$, $R^2=0.4956$ and $P=0.0315$, $R^2=0.1451$ respectively) after linear regression analysis were conducted, displaying lines of best fit (solid lines) along with the 95% confidence interval (dotted lines).

Summary

1) Within cancer cells, T14, alpha 7 receptors and AChE were all detected albeit with varying amounts. Surprisingly, all three proteins have similar mobility and their levels are positively correlated with each other, suggesting that they are complexed with each other.
2) Outside cancer cells (i.e. within the cell culture media), only the toxic T14 peptide was detected, but AChE and alpha-7 were not released into the external media. Moreover, T14 levels were higher outside the cells than inside for six out of the seven cancer cell lines, suggesting that T14 is produced to be released from the cell. Furthermore, the mobility of T14 outside the cell was different compared to that inside the cells.
3) Interestingly, the levels of T14 outside cancer cells were significantly negatively correlated with alpha-7 receptor levels within cancer cells. The inventors postulate that this could underlie a general disease mechanism as it is also the case within cerebral cortex and locus coeruleus homogenate of Alzheimer's disease patients (but not control patients), where a positive correlation exists instead between T14 and alpha-7. The inventors believe that this may be due to high concentrations of the T14 peptide down-regulating its target receptor in diseased individuals.
4) T14 levels inside and outside cancer cells were also measured by ELISA. The T14 levels in cancer cell media and cell lysate measured by ELISA were significantly inversely correlated with that from the Western Blot. This would suggest that ELISA may be measuring T14 monomers, whereas Western Blot is measuring T14 aggregate levels, and so the levels are complimentary.

Example 2

The objective of this example was to investigate, using Western Blotting, the relationship between the metastatic marker CD44 with the toxic T14 peptide, AChE, and the alpha-7 receptor in membrane and cytosol fractions of six cancer cell lines (JJN3, MDA-MB231, MCF-7, KG1a, MEC-1, H929) and one cancer-derived cell line (PC12).

Western Blotting Results

Qualitative data showed that, in the membrane fraction of all cell lines, CD44, AChE and T14 all have similar mobility (as shown in FIG. 9A, C, E), but that alpha-7 showed different protein mobility (see FIG. 9G). The same relationship between CD44, AChE and T14 was found in the cytosol portion of all cell lines (see FIG. 9B, D, F), with alpha-7 again being the exception (see FIG. 9H).

Subsequently, all four peptide/protein levels (CD44, AChE, alpha-7 and T14) were quantified and normalised against total protein levels (Colins et al 2015). Quantitative data showed that strongly metastatic cancer cell lines (KG1a, MDA-MB231, MEC-1) have more peptide/proteins in their membrane compared to the cytosol, whereas weakly metastatic cancer cell lines/cancer derived cell line (JJN3, H929, MCF-7 and PC12) showed variable relationships between membrane and cytosolic peptide/proteins (see FIG. 10).

Most importantly, the levels of metastatic marker CD44 is significantly and positively correlated with AChE in both the membrane (see FIG. 11A) and cytosol fractions (see FIG. 11B) as well as with T14 in both the membrane (FIG. 11C) and cytosol fractions (FIG. 11D). Moreover, AChE and T14 levels are significantly and positively correlated with each other in both the membrane (FIG. 11E) and cytosol fractions (FIG. 10). This finding strongly suggests that AChE and T14 are both good predictors of the degree of cancer metastasis, and perhaps the pivotal molecular intermediaries. Therefore, blocking the signalling actions of AChE and T14 can be utilized as anti-cancer therapeutics.

Summary

1) In six cancer cell lines and PC12 cells, the metastatic marker (CD44) is significantly and positively correlated with the toxic molecule T14 as well as with AChE.
2) This correlation is true for both within the cancer cell membrane and within the cancer cell cytosol.
3) This finding strongly suggests that T14 and AChE are good predictors of the degree of cancer metastasis, and perhaps the pivotal molecular intermediaries.

Example 3—T14 ELISA—CLL Cohort

Given T14's clear role in cancer metastasis, the inventors explored, using ELISA, the potential of T14 as a cancer biomarker and its link to patient survival rate.

Materials and Methods

T14 antibody: The antibody was synthesised by Genosphere Biotechnologies (Paris, France). Two New Zealand rabbits were used with four immunisations of keyhole limpet hemocyanin (KLH)-peptide (T14-hapten: CAEFHRWSSYMVHWK (SEQ ID No: 7); C was included to link to KLH as the immunogen) over 70 days. The animals were bled four times and the bleeds pooled. The antiserum was then passed through a gravity column with covalently bound peptide-support and, following washing, the antibodies were eluted in acidic buffer and the solution neutralised. Further dialysis against phosphate buffered saline (PBS) buffer and lyophilisation completed the process.

ELISA for T14 peptide antibody: The standard curves and the samples were run in triplicate. The human serum samples were diluted 1:10,000, and the standard curve for determination of relative T14 content in the samples was diluted in PBS buffer. The standard curve ranged from 3.3 to 40 nM of T14. Briefly, 96-well immunoplates (NUNC) were coated with 100 µl/well of sample or standard T14, covered with parafilm and incubated overnight at 4° C. The following day the sample was removed by flicking the plate over a sink with running water, and 200 ml of the blocking solution containing 2% bovine serum albumin (BSA) in Tris-buffered saline and TWEEN-20 detergent (TBS-T) was added and incubated for 4 h at room temperature. Blocking solution was then removed and 100 µl of antibody, diluted in blocking solution to 1 µg/ml, was added and incubated overnight at 4° C. The primary antibody was removed the next day and wells were washed 3 times with 200 µl of TBS-T. After 100 ml of secondary enzyme-conjugated antibody diluted in blocking solution to 0.1 mg/ml was added and incubated for 2 h at room temperature; the plate was covered with parafilm during all incubations. After 2 h, the plate was washed 4 times with TBS-T. The addition of 3,3,5,5-tetramethylbenzidine started the colour reaction. The reaction was stopped 30 min later with stopping solution containing 2M$H_2SO_4$, and the absorbance was measured at 450 nm in a Versamax plate reader (Molecular Devices, Wokingham, UK).

Analysis: The results of the assay are recorded in an arbitrary unit of optical density (OD). The OD of the blank was subtracted from the signal of each sample prior to analysis. The OD of each sample in the assay was compared to a baseline of the lowest known concentration of T14 in the standard curve. The optical density could then be represented in relation to a known signal, and recorded as a proportion of this signal. All samples were compared for their relative level of T14 as a direct reading from the standard curve is not yet possible with the current method in human blood samples. The grouping of the samples into the groups "High", "Med-High", "Med-Low", and "Low" are defined by the distance of the relative value from the mean value of the entire cohort. As the values are normally distributed, all values within 1 standard deviation of the mean are in the medium range, and are either "Med-High" if they are above the mean, and "Med-Low" if they are below the mean. "Low" T14 values are those that are below, and beyond the standard deviation of, the mean. Conversely "High" are those that are above, and also beyond the standard deviation of, the mean.

Results and Discussion

Referring to FIG. 23, there is shown a bar graph of the range of levels of T14 as measured by ELISA relative to a known concentration of exogenous T14. Patients are rank ordered by relative T14 concentrations in the examined CLL patient cohort.

Referring to FIG. 24, there is shown a table of values of T14 as measured by ELISA relative to a known concentration of exogenous T14 in the examined CLL patient cohort and a statistical grouping.

Referring to FIG. 25, there is shown ELISA values in 2 different groups divided by relative T14 concentration analysed statistically by using the Kaplan Meier estimate conducted on 100 CLL serum samples.

Referring to FIG. 26, there is shown ELISA values in 4 different groups divided by relative T14 concentration analysed statistically by using the Kaplan Meier estimate conducted on 100 CLL serum samples.

Example 4—Western Blot Data on the Cancer Samples (CLL Cohort)

Given T14's role in cancer metastasis, the inventors explored, using Western blotting, the potential of T14 as a cancer biomarker and its link to patient survival rate.

Materials and Methods

Samples: A total of 100 patients with CLL had their serum taken before their treatment and subsequently treated and monitored for 16 years.

Western blotting: Protein concentrations were determined in the serum samples above using the Pierce™ 660 nm Protein Assay (Thermo Scientific, 22660). Subsequently, Western blot analysis was conducted on the samples using the previous established method [Garcia Rates et al 2016— Garcia-Ratés, S., Morrill, P., Tu, H., Pottiez, G., Badin, A., Tormo-Garcia, C., Heffner, C., Coen, C. and Greenfield, S. (2016) '(I) pharmacological profiling of a novel modulator of the α7 nicotinic receptor: Blockade of a toxic acetylcholinesterase-derived peptide increased in Alzheimer brains', Neuropharmacology. doi: 10.1016/j.neuropharm.2016.02.006.] The primary antibodies used were anti-T14 antibody (1:1000) [Garcia Rates et al 2016]. The secondary antibody used was goat anti-rabbit antibody conjugated to horseradish peroxidase (Abcam, ab6721, 1:5000). Protein bands derived from the cell lysates were quantified using Image J, measuring total optical intensity, and were subsequently normalized to total protein levels using Blot FastStain to control for loading error.

Data analysis: T14 50 KDa/TP values were ranked from low to high and the median was calculated. Subsequently, the values were divided into two groups with the light grey group containing values below the median and the dark grey group containing values above the median (FIG. 28). Finally, Kaplan Meier estimate was performed on the above two groups. The analysis can assess the effect of a treatment on the number of subjects survived or saved after that treatment over a period of time (TTFT: time to first treatment). The survival curve is calculated by computing of probabilities of occurrence of event at a certain point of time and multiplying these successive probabilities by any earlier computed probabilities to get the final estimate.

Results

Referring to FIG. 27, there is shown a table with raw values of T14 50 KDa normalised to total protein from 100 serum samples from leukaemia patients detected by WB, separated groups below and above the median.

Referring to FIG. 28, Kaplan Meier estimate conducted on the two groups showed high prognostic significance in this cohort. Patients with serum T14 50 KDa/TP values less than the median (light grey group) were 2.37 times more likely to require treatment in unit time than those with serum T14/TP values above the median (dark grey group) as illustrated by the hazard ratio (HR=2.37, P=0.01, FIG. 42). Moreover, this survival analysis showed that T14 50 KDa/TP values are predicative TTFT. The estimated median survival times were not reached for the low risk group and 8.05 years for the high risk group.

Discussion

The inventors have shown previously that T14 is involved in the cancer mechanism and is a good cancer biomarker. Therefore, T14 together with conventional prognostic tools, can predict patient survival and time to first treatment.

Conclusions

In conclusion, western blot is a surprisingly reliable method for detecting status in leukaemia. Although, currently, the ELISA data may not be reliably used currently as a clinical indication, it could nonetheless show the underlying mechanism mediating cell migration.

Example 5—Design and Production of Peptidomimetic T14 Inhibitors

The inventors have designed and synthesised peptidomimetic compounds which inhibit T14 activity, and thereby outcompete T30 for the allosteric active site of the nicotinic receptor.

Compound 1—Tri02 (Score: −10.2)

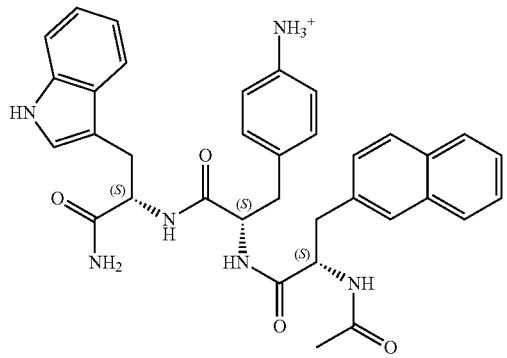

4-((S)-2((S)-2-acetamido-3-(naphthalene-2-yepropanamido)-3-(((S)-1-amino-3-(1H-indol-3-yl)-1-oxopropan-2-yl)amino)-3-oxopropyebenzenaminium Compound 2—Trio4 (Score: −9.4)

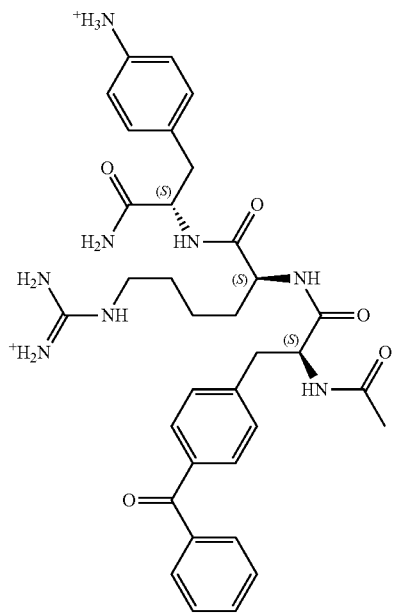

4-((S)-2-((S)-2-((S)-2-acetamido-3-(4-benzoylphenyl) propanamido)-6-((amino(iminio)methyeamino)hexanamido)-3-amino-3-oxopropyl)benzenaminium Example 6—Synthesis of Identified Compounds Materials and Methods The T14 inhibitor compounds 1 and 2 (Tri 02 and Tri 04) from Example 5 were synthesised by Genosphere Biotechnologies and analysed for purity using RP-HPLC (>99% pure), and mass by mass spectroscopy (average MS 604.79 for Tri02 and 628.83 for Tri04).

Brief Stepwise Description of Synthesis of TRI02—Sequence: [acetyl]-[2Nal][4nh2-F]-Trp-[amide]

1) Boc-Trp-OH+ClooEt+$NH_3 \cdot H_2O$ —Boc-Trp-$NH_2$, reaction in THF, extracted by acetic ether.
2) Boc-Trp-$NH_2$,4NHcl, removed Boc-, obtained H-Trp-$NH_2$.Hcl, precipitation reaction by diethyl ether.
3) (2-Naphtyl)-Ala+Acetic Anhydride—Ac-(2-Naphtyl)-Ala-OH, reaction THF/$H_2O$, extracted byacetic ether.
4) Boc-(4-$NH_2$)-Phe-OH+H-Trp-$NH_2$.Hcl—Boc-(4-$NH_2$)-Phe-Trp-$NH_2$, reaction in DMF, extracted by acetic ether.
5) Boc-(4-$NH_2$)-Phe-Trp-$NH_2$,4NHcl, removed Boc-, obtained H-(4-$NH_2$)-Phe-Trp-$NH_2$.Hcl, precipitation reaction by diethyl ether.
6) Ac-(2-Naphtyl)-Ala-OH+H-(4-$NH_2$)-Phe-Trp-$NH_2$.Hcl—Ac-(2-Naphtyl)-Ala-(4-$NH_2$)-Phe-Trp-$NH_2$ reaction in DMF, extracted by acetic ether.
7) Purification Brief Stepwise Description of Synthesis of TRI04—Sequence: [acetyl]-[bpa]R[4NH2-F]-[amide]

1) Rink Amide MBHA.Resin Soak in DCM for 30 mins, pumped dry, washed by DMF for 3 times, pumped dry.
2) Add Fmoc-(4-$NH_2$)Phe-OH,DIEA,HBTU,DMF,$N_2$, reaction for 30 mins, pumped dry, washed by DMF for 6 times, pumped dry.
3) Add piperidine/DMF to remove Fmoc-, reaction for 20 mins, pumped dry, washed by DMF for 3 times, pumped dry.
4) Add Fmoc-Arg(Pbf)-OH,DIEA,HBTU,DMF,$N_2$, reaction for 30 mins, pumped dry, washed by DMF for 6 times, pumped dry.
5) Repeat step 3.
6) Add Fmoc-Bpa-OH,DIEA,HBTU,DMF,$N_2$, reaction for 30 mins, pumped dry, washed by DMF for 6 times, pumped dry.
7) Repeat step 3.
8) Add Acetic Anhydride/DMF,$N_2$, reaction for 30 mins, pumped dry, washed by DMF for 3 times, pumped dry, washed by DCM for 3 times, pumped dry, washed by MeOH for 3 times, pumped dry.
9) Peptide cleaved from resin, pumped dry, precipitation reaction by diethyl ether, obtain the crude peptide, centrifugal drying.
10) Purification Example 7—T30 vs T14

With reference to FIG. 43, the inventors' initial work was performed with the 14mer T14, proving to be trophic-toxic in a range of preparations. Whilst the active sequence of AChE-peptide can be attributed to a specific 14 amino acid sequence originating from the C-terminus tail of AChE (T14) (Greenfield, 2013—Greenfield, S. A. (2013) 'Discovering and targeting the basic mechanism of neurodegeneration: The role of peptides from the c-terminus of acetylcholinesterase: Non-hydrolytic effects of ache: The actions of peptides derived from the c-terminal and their relevance to neurodegeneration', Chemico-biological interactions. 203 (3), pp. 543-6. doi: 10.1016/j.cbi.2013.03.015), exogenous AChE-peptide treatment in investigations has more recently involved a 30 amino acid peptide (T30) which includes the active T14 motif: the larger T30 is less likely to form fibrils when in solution, thereby possessing a higher stability and greater efficacy than T14 (Bond et al., 2009Bond, C., Zimmermann, M. and Greenfield, S. (2009) 'Upregulation of alpha7 Nicotinic receptors by Acetylcholinesterase c-terminal peptides', PloS one., 4(3). doi: 0.1371/journal.pone.0004846).

Hence, the T30 peptide was used throughout this study (Badin, A. S., Morrill, P., Devonshire, I., Greenfield, S. A., 2016 Jan 7. (II) Physiological profiling of an endogenous acetylcholinesterase-derived peptide in the basal forebrain: age-related bioactivity and blockade with a novel modulator. Neuropharmacology. 105, 47e60). The 15 amino acid residues at the C terminal of T30, 'T15', has been used as a control as it proved inert on its own and therefore not contributing to the bioactivity of T14. Moreover, the efficacy of T14 itself has been shown in the need for the antibody to bind to a terminal lysine on the C terminus that would not be exposed within the longer T30 sequence. Hence, T30 is useful in exploring the effects of the exogenous peptide or its endogenous counterpart.

In summary, T30 is a convenient experimental tool for exploring trophic-toxic effects, providing an inert control, and allowing for the antibody to detect endogenous T14 without cross-contamination with the exogenous (T30) peptide probe. Accordingly, any data showing that T30 activity is inhibited is a demonstration that T14 activity is also inhibited.

Example 8—Evaluation of Compound 1(Tri02) and Compound 3 (Tri04) in Cell Cultures The inventors tested T30, NBP-14, and Tri02 in cell culture studies to determine their effects on acetylcholinesterase activity and calcium influx, and the effects of Tri04 on calcium influx.

Materials and Methods

1. AChE Activity Assay

AChE activity was measured using the Ellman reagent that measures the presence of thiol groups as a result of AChE activity. In the case of the G4 experiment, AChE (G4) activity was tested alone and also together with either NBP14 or Tri peptides. PC12 cells were plated the day before the experiment as for the cell viability assay. Cells were treated with T30 (1 µM) alone or combined with NBP14 or Tri peptide (0.5 µM). After treatment, supernatant (perfusate) of each treatment was collected and 25 µL from is each condition were added to a new flat bottomed 96 well plate followed by the addition of 175 µl of Ellman reagent (Solution A: $KH_2PO_4$ 139 mM and $K_2HPO_4$ 79.66 mM, pH 7.0; solution B (substrate): Acetylthiocholine Iodide 11.5 mM; Solution C (Reagent): 5,5'-dithiobis (2-nitrobenzoic acid) 8 mM and $NaHCO_{15}$ mM). The Ellman reagent was prepared as a mixture of the 3 solutions in a ratio 33(A):3 (B):4(C). Absorbance measurements were taken for an interval of 60 minutes across experiments at 405 nm in a Vmax plate reader (Molecular devices, Wokingham, UK).

2. Calcium Fluorometry

PC12 cells were plated in 200 µl of Dulbecco's Modified Eagle's medium (DMEM) plus 2 mM of L-glutamine medium the day before the experiment in 96 well plates. On the day of the experiment, the Fluo-8 solution (Abcam) was prepared as described by the provider by adding 20 µl of Fluo-8 in the assay buffer that contains 9 ml of Hank's Balanced Salt Solution (HBSS) and 1 ml of pluronic F127 Plus. Subsequently, 100 µl of growth medium was removed and 100 µl of Fluo-8 solution were added. Treatments with T30 in conjunction with NBP14 or Tri peptides were added and incubated for 30 minutes in the incubator and 30 minutes room temperature. After 1 h, the plate was placed in the fluorescence plate reader (Fluostar, Optima, BMG Labtech, Ortenberg, Germany). Before reading the fluorescence, PNU282987 1 µM, an alpha7 specific agonist of the nicotinic receptors, was prepared and placed in the Fluostar injector. For each well, the reading was formed by a basal fluorescence reading followed by PNU282987 injection that induced an increase of calcium via nicotinic receptors.

3. Data Analysis

In each of the different cell techniques, the statistics analysis was performed with the average of the percentage values of 3 or more experiments. Comparisons between multiple treatment groups and the same control were performed by one-way analysis of variance (ANOVA) and Tukey's post-hoc tests using GraphPAD Instat (GraphPAD software, San Diego, Calif.). Statistical significance was taken at a p value<0.05.

Results

The results for Trio2 are shown in FIGS. 12 and 13, in which n values shown on the subsequent graphs refer to number of repeated experiments. As can be seen, 1 µM T30 increases calcium influx and AChE activity, and, as shown in previous work (see WO 2005/004430), 1 µM NBP14 protects against these toxic effects.

In addition, as can be seen in the Figures, Tri02 also clearly protects against the toxic effects of T30 by reducing both calcium influx and AChE activity. As such, the inventors are convinced that Tri02 acts as a T14 activity inhibitor and can be used to treat cancer or matastasis.

The results for Tri04 in PC12 cell culture are shown in FIG. 19. The cells were derived from a PC12 cell line, which come from a tumour of the adrenal gland and act as neurons (Bornstein et al., Mol. Psychiatry (2012), 17, 354-358). As can be seen, Tri04 also protects the toxic effects of T30 by reducing calcium influx in these cells indicating that it acts as a T14 inhibitor, and can therefore be used to treat cancer or metastasis.

Example 9—Evaluation of Compound 1 in Brain Slices

The inventors tested NBP-14 and Tri02 in brain slice studies using voltage-sensitive dye imaging (VSDI).

Materials and Methods

1. Brain Slice Preparation

Male Wistar rats (14 days old) were anaesthetised using isoflurane (~15 ml, 100% w/w). Isoflurane was applied to the cotton bed at the bottom of an anaesthetic chamber (glass box 20×15×15 cm) where rats were then placed for approximately 45 s until complete anaesthesia was reached. The hind paw of each anaesthetised rat was pinched to check for the appropriate depth of anaesthesia. Upon confirmation of anaesthesia, rats were quickly decapitated, with the brain being quickly removed and immersed in ice cold oxygenated 'slicing' artificial cerebrospinal fluid (aCSF in mmol: 120 NaCl, 5 KCL, 20 $NaHCO_3$, 2.4 $CaCl_2$ 2 $MgSO_4$, 1.2 $KH_2PO_4$, 10 glucose, 6.7 HEPES salt and 3.3 HEPES acid; pH=7.1). Coronal slices (400 µm thick) were then taken from a block of brain containing the basal forebrain, namely the MS-dBB complex (between +9.20 and +9.48 mm Interaural and +0.48 and +0.2 mm Bregma, FIG. 4A) and the somatosensory barrel field cortex (SiBF, between +8.08 and +7.20 mm Interaural and −0.92 mm and −1.80 mm Bregma) (Paxinos and Watson, 1998) using a Vibratome (Leica VT1000S). Slices were then transferred to a bubbler pot containing oxygenated aCSF at room temperature (recording aCSF in mmol: 124 NaCl, 5 KCL, 20 $NaHCO_3$, 2.4 $CaCl_2$ 2 $MgSO_4$, 1.3 $KH_2PO_4$, 10 glucose; pH=7.4) which was identical to that used in VSDI (voltage sensitive dye imaging) recording. Slices were then left for approximately 1-1.5 hours before preparing them for VSD staining.

2. VSD Setup

Slices were placed in a dark, high humidity chamber filled with aCSF bubbled with 95% $O_2$, 5% $CO_2$. Once there, the dye solution (4% 0.2 mM styryl dye pyridinium 4-[2-[6-(dibutylamino)-2-napthalenyl]-ethenyl]-1-(3-sulfopropyl) hydroxide(Di-4-NEPPS), Invitrogen, Paisley, UK in 48% aCSF, 48% foetal bovine serum, 3.5% DMSO and 0.4% cremophore EL) (Tominaga et al., 2000) was applied to the slices for 20-25 minutes before being transferred back to a bubbler pot containing oxygenated aCSF kept at room temperature for 30 minutes.

When starting the VSDI recordings, slices were placed in the recording bath on a small piece of filter paper to allow the flow of oxygenated aCSF on the underside of the slice and in order to keep it alive. The slice was then weighed down by a home-made plastic grid that was placed on top of the slice. The perfusing bath solution was heated to 30±1° C. by a stage heater. A concentric bipolar stimulating electrode (FHC, Maine, USA) was placed in the ventral diagonal band of the basal forebrain with stimulation being set to 30V. For the acquisition of VSD data, 2 dimensional images, equivalent to 88×60 pixels, were recorded using the MiCamo2 High Resolution camera (Brain Vision, Japan) with BV_Analyze imaging software. Acquisition of images was coupled to Spike2 V4.23 software (CED Ltd, Cambridge, UK) in order to align the image capture with the stimulation protocol (every 28 s with 30 repeats) via the Micro 1401 MkII. (CED Ltd, Cambridge, UK). Light was generated using an Osram halogen xenophot 64634 HLX EFR Display/Optic lamp and was filtered to emit green (530±10 nm) light using a MHF-G150LR (Moritex Corporation) coupled to the MiCamo2 High resolution imaging system and filtered the emitted fluorescence through a >590 nm high pass filter.

3. Drug Preparation and Application

Acetylcholinesterase (AChE) C-terminus 30 amino acid peptide (T30; sequence: 'N'—KAEFHRWSSYMVHW-KNQFDHYSKQDRCSDL—SEQ ID No: 2), the cyclic version of the active 14 amino acid region of T30 (NBP14; sequence: c[AEFHRWSSYMVHWK]—SEQ ID No: 3; c[ ]=cyclic, N-terminal to C-terminal) and the inert 15 amino acid peptide contained within the T30 sequence (Tis; sequence: 'N'—NQFDHYSKQDRCSDL—SEQ ID No: 4) were custom synthesised and purchased from Genosphere Biotechnologies (Paris, France) at >99% purity. The linear peptidomimetic, Tri02 was designed in silico by Iproteos (Barcelona, Spain) and synthesised and purchased from Genosphere Biotechnologies at >99% purity. All drug and peptide stocks were prepared in frozen aliquots prior to experiments. For the production of perfusion solutions, stock solutions were thawed and added to recording aCSF as appropriate and bath applied at a constant rate of 1.5 ml/min perfusion using the Minipulse 3 peristaltic pump (Gilson Scientific Ltd., Bedfordshire, UK). Each experimental trial lasted 52 minutes, with 20 minutes to establish a baseline recording (perfusion with recording aCSF only), 12 minutes to allow the drug solution to perfuse into the bath as well as to let the dye molecules reseat themselves in the cell membranes and finally, a 20 minute recording period measuring the response in the presence of the drug solution.

4. Data Analysis and Statistics

From the 2 dimensional images generated with each drug condition, the critical data such as the time-course of activation, intensity and spread of the overall fluorescent signal were extracted. These data were processed using a custom script to convert them into usable MatLab (Mathworks Inc. Massachusetts, US) files and then analysed using a Matlab toolbox specifically made for VSDI data analysis (Bourgeois et al., 2014). This toolbox allows for the selection of a fixed region of interest (ROI) geometry that can be applied to every slice, in order to extract and collate the data from an identical ROI across all slices used in each experiment. For the basal forebrain slices, the ROI that will be used is the MSdBB complex, chosen as it encompasses the MS (medial septal nuclei), VDB (ventral diagonal band) and HDB (horizontal diagonal band). More crucially, this ROI was chosen in order to include the entirety of the evoked response. This response can be plotted as a single averaged time series or over space and time in a 'space-time map' so as to provide a qualitative description of the data. However, in order to produce quantifiable values, the area underneath the time series was calculated (summed fluorescence fractional change) between the moment of stimulation (t=0) and 156 ms after that. Due to the variability of responses seen between each individual slice, the raw data generated from each experiment was normalised with respect its own baseline to give normalised fluorescence values. This method of quantification was chosen in order to account for the multiple components of the signal generated by VSDI (Chemla and Chavane, 2010) namely the immediate peak and the long latency response (Badin et al., 2016). Statistics were carried out in Prism Graphpad 6.

5. Analysis of Modulatory Peptides

Throughout the experiments in which T30 was used, an increase or a decrease in signal was observed. Thus upon averaging these results together, no change was detected. However, given the past observed modulatory effects of this peptide in various preparations (Bon and Greenfield, 2003, Day and Greenfield, 2004, Greenfield et al., 2004, Badin et al., 2013) and the fact that the changes induced by application of T30 n this type of preparation are moderately negatively correlated (r=−0.4286, p=0.0257, Spearman's rank correlation, n=27, FIG. 13A) with baseline response amplitude, it was decided that these results should be dichotomised by whether an increase or a decrease was seen.

Subsequently, a similar correlation analysis was performed for each experiment in which an exogenous compound was added (FIG. 16). Upon determination of a significant correlation, data was then categorised based on whether and increase or a decrease was seen.

Results

Referring to FIGS. 14 and 15, addition of 4 μM Triol recapitulates results seen with application of 4 μM NBP14.

Referring to FIG. 14, addition of NBP14 (4 uM) to the perfusate induced small, non-significant alterations to the magnitude (summed fluorescence) of evoked responses. Though insignificant, these small induced changes were found to be inversely correlated with magnitude of baseline response; as a result, data were split into trials which caused slight decreases (left histograms) and those which caused increase (right histograms), both in real (top) and normalised (bottom) data format. If considered together, the dataset would show no change from baseline (as increases and decreases would cancel each other out), yet it was crucial to check that no significant effects were induced by NB14 even when the fluorescence changes were considered separately.

As shown in FIG. 15, addition of Tri02 (4 uM) to the perfusate induced small alterations to the magnitude (summed fluorescence) of evoked responses, with induced decreases (n=8 of 11 total) showing a significant deviation from normalised baseline level (bottom left histogram, p<0.05). These changes were also found to be inversely correlated with magnitude of baseline response; as a result, data were split into trials which caused decreases (left histograms) and those which caused increases (right histograms), both in real (top) and normalised (bottom) data format. If considered together, the dataset would show no change from baseline (as increases and decreases would cancel each other out), yet it was crucial to check that no significant effects were induced by NB14 even when the fluorescence changes were considered separately.

Analysis of Modulatory Pep Tidomimetics

Referring to FIG. 16, there is shown correlation analysis for Tri02 (4 uM) and T30 (2 uM) data (n=15) showing that their co-perfusion induces some changes to the magnitude of evoked responses, with some slices featuring slight increases in activity (n=6) whilst most showed slight decreases (n=9). This correlation was found to be significant (p=0.0405; $r^2$=0.534), providing justification to split the data into those that showed increases and decreases in evoked activity as a result of Tri02 and T30 application, just as was done for the addition of NBP14 and Tri02 (FIGS. 14 & 15, respectively).

Referring to FIG. 17, there is shown quantification of effects mediated by the addition of Tri02 and T30: Both in the case of induced increases and decreases, Tri02 was not found to protect against T30-induced deviations from baseline, with significant decreases (left panel, p<0.01, n=9) and increases (right panel, p<0.05, n=6) reported in overall effects.

As shown in FIG. 18, overall line graph of normalised effects respective to baseline for experiments testing the effects of normal aCSF (black line), 2 uM T30 (red lines), T30 (2 uM) and 4 uM NBP14 (blue lines), T30 (2 uM) and 4 uM Tri02, control NBP14 (4 uM) experiments (FIG. 11, orange lines), control Tri02 (4 uM) experiments (FIG. 15, purple lines). This graph shows the normalised decreases relative to baseline and each other, with T30 alone inducing the greatest deviation, and Tri02 showing some efficacy in blocking those T30-induced deviation, yet with significant changes still taking place in their co-perfusion (green lines).

Example 10—Evaluation of Compound 2 in Brain Slices

The inventors tested Tri04 in brain slice studies using voltage-sensitive dye imaging (VSDI).

Materials and Methods

1. Brain Slice Preparation

Brain slices were prepared as in Example 8.

2. VSD Setup

Slices were placed in a dark, high humidity chamber filled with aCSF bubbling with 95% $O_2$ 5% $CO_2$. Once there, the dye solution (4% 0.2 mM styryl dye pyridinium 4-[2-[6-(dibutylamino)-2-aphthalenyl]-ethenyl]-1-(3-sulfopropyl) phydroxide (Di-4-ANEPPS, Invitrogen, Paisley, UK) (Tominaga et al., 2000) in aCSF 48%, fetal bovine serum 48%, DMSO 3.5% and cremophore EL 0.4%) was applied to the slices for 20-25 min before being transferred to an aCSF bubbler pot (room temperature, 22 C+/−1.5 C) for 1 h to wash off excess dye and recover.

When starting VSD recordings, slices were placed in the recording bath on a small piece of filter paper to keep slice alive and was weighed down appropriately using a homemade plastic grid placed atop the slice. The perfusing bath solution was heated to 30+/−1 C by a stage heater. A concentric bipolar stimulating electrode (FHC, Maine, US) was placed in the ventral diagonal band of the basal forebrain with stimulation being set at 30V. For acquiring of VSD data, 16-bit images were recorded with ims resolution with a digital camera (Brain Vision MiCAM Ultima R3-V20 Master) with Ultima 2004/08 imaging software (Brain Vision) coupled to Spike 2 V6.0 (CED Ltd, Cambridge, UK) which was used to trigger stimulations with respect to appropriate ISI. Light was generated using an Osram halogen xenophot 64634 HLX EFR Display/Optic lamp and was filtered to emit green (530+/−10 nm) light using a MHF-G150LR (Moritex Corporation) coupled to MiCAM Ultima ultra-fast imaging system and filtered the emitted fluorescence through a >590 nm high-pass filter.

3. Drug Preparation and Application

The linear peptidomimetic, Tri04, was designed in silico by Iproteos (Barcelona, Spain) and synthesised and purchased from Genosphere Biotechnologies at >99% purity. All drug and peptide stocks were prepared in frozen aliquots prior to experiments. For the production of perfusion solutions, stock solutions were thawed and added to recording aCSF as appropriate and bath applied at a constant rate of 1.5 ml/min perfusion using the Minipulse 3 peristaltic pump (Gilson Scientific Ltd., Bedfordshire, UK). Each experimental trial lasted 52 minutes, with 20 minutes to establish a baseline recording (perfusion with recording aCSF only), 12 minutes to allow the drug solution to perfuse into the bath as well as to let the dye molecules reseat themselves in the cell membranes and finally, a 15 minute recording period measuring the response in the presence of the drug solution.

5. Analysis of Modulatory Peptides

Throughout the majority of experiments in which T30 was used, a decrease in signal was observed. T30 induced a net inhibition (n=21) in recorded VSDI signal in the basal forebrain of p14 rats, this value actually includes a minority of instances where negligible or marginally positive effects were seen during T30 perfusion (Badin et al., 2016).

Results and Discussion

Referring to FIGS. 20, 21 and 22, addition of 4 μM Tri04 recapitulates results previously seen with the application of 4 μM NBP14, while 2 μM Tri04 in the perfusion solution determines a significant effect on basal forebrain population activity.

Analysis of Modulatory Peptidomimetics

Referring to FIG. 20A, there is shown that space-time maps exhibit a recovery in basal forebrain activity due to the presence of 2 uM Tri04 in the perfusate containing 2 μM of T30 (n=29). More specifically, 2 μM Tri04 determines a reversal of the inhibitory effect of T30 over activity measured by direct stimulation of the rat basal forebrain.

Referring to FIG. 20B, bar graphs relative to the 3 recording epochs show changes in the evoked response after Tri04 application, confirming that 2 μM Tri04 co-perfusion induces an increase in network activity (n=29, p=0.06, two-tailed paired t-test) caused by a inhibition of T30-induces effects.

Referring to FIG. 21, there is shown that response time-series across the three recording conditions (baseline, T30 application to the artificial cerebro-spinal fluid (aCSF) and co-application of T30 and Tri04 to the aCSF show a similar activation profile for T30 recordings and T30+Tri04 for the first 100 msec, while a higher activity in recordings made in presence of Tri04 is detectable afterwards, confirming a protective role of Tri04 over T30.

Referring to FIG. 22, there is shown bar graphs relative to three recording conditions. The co-perfusion of 4 μM Tri04 in the artificial cerebro-spinal fluid (aCSF) containing 2 uM T30 determines a significant effect reversing T30 activity. In particular, Tri04 has been found to be protective against T30-induced deviations from the baseline with a significant increase (n=20, p<0.05, two-tailed paired t-test) in basal forebrain activity in comparison to recordings in the presence of T30 alone. Therefore, Tri04 shows some efficacy blocking T30 toxic effects on meso-scale network activity.

Conclusions

Treatment of Cancer

The inventors have demonstrated herein that the antibody, and the two peptidomimetics, Tri02 and Tri04, act as inhibitors of the activity of the T14 peptide, due to the clear inhibitory effects on T30 in the data shown herein. Accordingly, these compounds can be used to treat, ameliorate or prevent cancer, and especially metastatic disease.

Diagnosis/Prognosis of Cancer

The inventors have also shown that T14, or variants thereof, such as its truncations, can be used as a diagnostic or prognostic marker of cancer, and especially metastatic disease. Low T14 levels as measured by western blots in the blood are indicative of poorer survival rates and corresponding longer time to first treatment (i.e. clinical status).

The invention claimed is:

1. A method for diagnosing and treating an individual who suffers from metastatic disease, or a pre-disposition thereto, the method comprising:
   (a) obtaining a sample from the individual;
   (b) detecting, in the sample for the presence of an endogenous peptide of SEQ ID No: 3, or a variant thereof having at least 90% sequence identity to SEQ ID No: 3;
   (c) diagnosing the individual with metastatic disease when the presence of the endogenous peptide of SEQ ID No: 3, or a variant thereof having at least 90% sequence identity to SEQ ID No: 3, is detected in the sample; and
   (d) administering an effective amount of a treatment for metastatic disease to the diagnosed individual.

2. The method of claim 1, wherein the sample is blood, plasma, serum, spinal fluid, urine, sweat, saliva, tears, breast aspirate, prostate fluid, seminal fluid, vaginal fluid, stool, cervical scraping, cytes, amniotic fluid, intraocular fluid, mucous, moisture in breath, animal tissue, cell lysates, tumour tissue, hair, skin, buccal scrapings, lymph, interstitial fluid, nails, bone marrow, cartilage, prions, bone powder, ear wax, or combinations thereof.

3. The method of claim 1, wherein the sample comprises a blood sample.

4. The method of claim 1, wherein the sample comprises venous or arterial blood.

5. The method of claim 3, wherein the blood sample comprises blood serum or blood plasma.

6. The method of claim 1, wherein the method comprises assaying for a labelled compound having affinity with a ligand of the endogenous peptide of SEQ ID No: 3, or a variant thereof having at least 90% sequence identity to SEQ ID No: 3.

7. The method of claim 1, wherein the method comprises immunoassaying the sample to detect the presence of the endogenous peptide of SEQ ID No: 3, or a variant thereof having at least 90% sequence identity to SEQ ID No: 3.

8. The method of claim 1, wherein the endogenous peptide of SEQ ID No: 3, or a variant thereof having at least 90% sequence identity to SEQ ID No: 3 is detected by Western Blot analysis, enzyme-linked immunosorbent assay (ELISA), fluorometric assay, chemiluminescent assay, or radioimmunoassay analyses.

9. The method of claim 1, wherein the variant of SEQ ID No:3 comprises or consists of SEQ ID No:6.

10. The method of claim 1, wherein the method comprises detecting for the absence of SEQ ID No:2.

11. The method of claim 1, wherein the method comprises detecting for the absence of SEQ ID No:4.

12. The method of claim 1, wherein the method comprises detecting the presence of an endogenous peptide of SEQ ID No: 3, or a variant thereof having at least 90% sequence identity to SEQ ID No: 3 with an antibody or antigen-binding fragment thereof that specifically binds to SEQ ID No: 3.

13. The method of claim 1, wherein the treatment comprises administration of a therapeutic agent and/or treatment regime that prevents, reduces or delays the development of metastatic disease.

14. The method of claim 13, wherein the therapeutic agent comprises Herceptin, or wherein the treatment regime comprises radiotherapy or chemotherapy.

15. A method for diagnosing and treating an individual who suffers from metastatic disease, or a pre-disposition thereto, the method comprising:
   (a) obtaining a sample from the individual;
   (b) detecting the presence of an endogenous antigen consisting of SEQ ID No: 3 in the sample;
   (c) diagnosing the individual with metastatic disease when the presence of the endogenous antigen in the sample is detected; and
   (d) administering an effective amount of a treatment for metastatic disease to the diagnosed individual.

* * * * *